US011174486B2

(12) United States Patent
Hasty et al.

(10) Patent No.: US 11,174,486 B2
(45) Date of Patent: Nov. 16, 2021

(54) ENGINEERED BACTERIA FOR PRODUCTION AND RELEASE OF THERAPEUTICS

(71) Applicants:The Regents of the University of California, Oakland, CA (US); Massachusetts Institute of Technology, Cambridge, MA (US)

(72) Inventors: Jeff Hasty, Encinitas, CA (US); Lev Tsimring, San Diego, CA (US); Muhammad Omar Din, San Diego, CA (US); Arthur Prindle, San Diego, CA (US); Sangeeta Bhatia, Lexington, MA (US); Tal Danino, Cambridge, MA (US)

(73) Assignees: The Regents of the University of California, Oakland, CA (US); Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/565,131

(22) PCT Filed: Apr. 7, 2016

(86) PCT No.: PCT/US2016/026518
§ 371 (c)(1),
(2) Date: Oct. 6, 2017

(87) PCT Pub. No.: WO2016/164636
PCT Pub. Date: Oct. 13, 2016

(65) Prior Publication Data
US 2018/0148729 A1 May 31, 2018

Related U.S. Application Data

(60) Provisional application No. 62/145,417, filed on Apr. 9, 2015.

(51) Int. Cl.
| | | |
|---|---|---|
| *C12N 15/74* | (2006.01) | |
| *A61K 35/74* | (2015.01) | |
| *A61K 38/16* | (2006.01) | |
| *C12N 1/06* | (2006.01) | |
| *C12N 1/20* | (2006.01) | |
| *C12N 15/63* | (2006.01) | |
| *C12P 21/02* | (2006.01) | |

(52) U.S. Cl.
CPC .............. *C12N 15/74* (2013.01); *A61K 35/74* (2013.01); *A61K 38/16* (2013.01); *C12N 1/06* (2013.01); *C12N 1/20* (2013.01); *C12N 15/63* (2013.01); *C12P 21/02* (2013.01)

(58) Field of Classification Search
None
See application file for complete search history.

(56) References Cited

U.S. PATENT DOCUMENTS

| 5,196,318 A * | 3/1993 | Baldwin ................ C07K 14/28 |
|---|---|---|
| | | 435/320.1 |
| 2012/0069914 A1 | 3/2012 | Shental et al. |
| 2013/0052164 A1 | 2/2013 | Chang et al. |
| 2013/0209405 A1* | 8/2013 | Curtiss, III ............... C12R 1/42 |
| | | 424/93.2 |
| 2015/0209393 A1 | 7/2015 | Chang et al. |

FOREIGN PATENT DOCUMENTS

| CN | 201362719 | 12/2009 |
|---|---|---|
| CN | 104131018 | 11/2014 |
| EP | 2182068 | 5/2010 |
| JP | 2008519002 | 6/2008 |
| KR | 20160000979 | 1/2016 |
| WO | WO 2014/046593 | 3/2014 |
| WO | WO 2014/098767 | 6/2014 |

OTHER PUBLICATIONS

Chlebina et al. Continous Protein Production and Release via Oscillatory Suicidal Lysis Circuits. Dissertation Thesis. Department of Biomedical Engineering. Duke University. Published 2012.*
Bernades et al. Appl Microbiol Biotechnol (2013) 97:5189-5199.*
Cummins et al. Infectious Agents and Cancer 2013, 8:11, p. 1-8.*
Dai et al., "Construction of an inducible cell-communication system that amplifies *Salmonella* gene expression in tumor tissue", Biotech. And Bioengineering, vol. 110, No. 6, pp. 1769-1781, 2013.
Din et al., "Synchronized cycles of bacterial lysis in vivo delivery", Nature, vol. 536, No. 7614, pp. 81-85, 2016.
Extended European Sear Report in Application No. 16777310, dated Oct. 17, 2018, 13 pages.
Higashikuni et al., "Advancing therapeutic applications of synthetic gene circuits", Current opinion in biotech., vol. 47, pp. 133-141, 2017.
Kaur et al., "Bacteriocins as Potential Anticancer Agents", Frontiers in Pharmacology, vol. 6, p. 272, 2015.
Andersen et al., "New unstable Variants of Green Fluorescent Protein for Studies of Transient Gene Expression in Bacteria." Appl. Environ. Microbiol., vol. 64, No. 6, pp. 2240-2246, Jun. 1998.
Baban et al., "Bacteria as Vectors for Gene Therapy of Cancer." Bioeng. Bugs 1:6, pp. 385-394, 2010.
Begley et al., "Drug development: Raise standards for preclinical cancer research.", Nature, vol. 483, pp. 531-533, Mar. 29, 2012.
Buchler et al., "Molecular titration and ultrnsensitivity in regulatory networks." Mol. Biol. 384, 1106-1119, 2008.
Burger et al., "Abduction and asylum in the lives of transcription factors.", Proc. Natl. Acad. Sci. USA, vol. 107, No. 9, pp. 4016-4021, Mar. 2, 2010.

(Continued)

*Primary Examiner* — Oluwatosin A Ogunbiyi
(74) *Attorney, Agent, or Firm* — Fish & Richardson P.C.

(57) ABSTRACT

Some embodiments described herein relate to cells which have been genetically engineered to release a polypeptide when a population of the cells reaches a desired density. In some embodiments, the released polypeptide may be a therapeutic polypeptide. In some embodiments, the therapeutic polypeptide kills tumor cells or which inhibits the growth of tumor cells.

28 Claims, 58 Drawing Sheets

(56) References Cited

OTHER PUBLICATIONS

Cann et al., "Dr William Coley and Tumour Regression: A Place in History or in the Future." Postgraduate Med. Journal, 79, pp. 672-680, 2003.
Chen, R. et al. "Application of a pro-apoptotic peptide to intratumorally spreading cancer therapy", Cancer Research, 73, pp. 1352-1361, Feb. 15, 2013.
Cheong et al. "A Bacterial Protein Enhances the Release and Efficacy of Liposomal Cancer Drugs." Science 314, 1 308-1311, 2006.
Cho et al.,"The Human Microbiome: At the Interface of health and disease." Nature Reviews Genetics, 13, pp. 260-270, 2010.
Coley, "The Treatment of Inoperable Sarcoma by Bacterial Toxins (the mixed toxins of the *Streptococcus erysipelas* and the *Bacillus prodigiosus*).", Proceedings of the Royal Society of Medicine, 48 pages, Jul. 13, 1910.
Cookson et al.,"Queueing Up for Enzymatic Processing: Correlated SignalingThrough Coupled degradation.", Mol. Syst. Biol. ,7, article No. 561, 9 pages, 2011.
Dang et al., "Combination bacteriolytic therapy for the treatment of experimental tumors.", Proceedings of the National Academy of Sciences, vol. 98, No. 26, pp. 15155-15160, Dec. 18, 2001.
Danino et al., "Measuring Growth and Gene Expression Dynamics of Tumor-Targeted *S. typhimurium* Bacteria.", JoVE (Journal of Visualized Experiments), 7 pages, Jul. 2013.
Danino et al., In vivo gene expression dynamics of tumor targeted bacteria, ACS Synthetic Biology, 1, pp. 465-470, 2012.
Danino et al., "A Synchronized Quorum of Genetic Clocks." Nature 463, 326-330, 2010.
Danino et al., "Programmable probiotics for detection of cancer in urine", Science translational medicine 7, 289ra84-289ra84, 2015.
Davila et al., "Efficacy and Toxicity Management of 1 9-28z CAR T Cell Therapy in B Cell Acute Lymphoblastic Leukemia." Science 'Translational Medicine 6, 224-224ra25, 2014.
De Boer et al., "The Tac Promoter: A Functional Hybrid Derived from the TRP and LAC Promoters.", Proceedings of the National Academy of Sciences, vol. 80, pp. 21-25, Jan. 1983.
Del Vecchio et al., "Modular Cell Biology •Retroactivity and Insulation.", Mol. Syst. Biol. 4, article No. 161, 16 pages, 2008.
Derman, et al., "Phylogenetic Analysis Identifies Many Uncharacterized Actin-Like Proteins (Alps) in Bacteria: Regulated Polymerization, Dynamic Instability and Treadmilling in Alp7a.", Molecular Microbiology, 73, pp. 534-552, 2009.
Ferry et al., "Microfluidics for Synthetic Bioiogy from Design to Execution.", Methods Enzymol, 497, pp. 295-372, 2011.
Fischbach et al.,. "Cell-Based Therapeutics: The Next Pillar of Medicine.", Science Translational Medicine, vol. 5, Issue 179, 7 pages, Apr. 3, 2013.
Folcher et al., "Synthetic Biologly Advancing Clinical Applications." Current Opinion in Chernical Biology, 16, pp. 345-354, 2012.
Forbes et al., "Engineering the Perfect (bacterial) Cancer Therapy.", Nature Reviews Cancer 10, pp. 785-794, Nov. 2010.
Fredriksson et al., "Decline in Ribosomal Fidelity Contributes to the Accumulation and Stabilization of the Master Stress Response Regulator Upon Carbon Starvation.", Genes. Dev. 21, pp. 862-874, 2007.
Gardner et al., "Construction of a Genetic Toggle Switch from *Escherichia coli*." Nature 403, 339-342, 2000.
Garrett et al., "Cancer and the Microbiota.", Science 348, pp. 80-86, Apr. 3, 2015.
Gerdes, K., "The ParB (hok/sok) Locus of Plasmid R 1: A General Purpose Plasmid Stabilization System.", Nature Biotechnology 6, 1402-1405,1988.
Goldbeter et al., An Amplified Sensitivity Arising from Covalent Modification in Biological Systems., Proc. Natl. Acad. Sci. USA, vol. 78, No. 11, pp. 6840-6844, Nov. 1981.
Griffith et al., "Inducible protein degradation in Bacillus subtilis using heterologous peptide tags and adaptor proteins to target substrates to the protease Clpx'P.", Mol. Microbiol. 70, pp. 1012-1025, 2008.
Grunberg et al., "Strategies for protein synthetic biology.", Nucleic Acids Res., vol. 38, No. 8, pp. 2663-2675, 2010.
Hohmann et al., "Evaluation of a Phop/Phoq-Deleted, Aroa-Deleted Live Oral *Salmonella typhi* Vaccine Strain in Human Volunteers." Vaccine 14, 19-24, 1996.
Hooshangi et al., "Ultrasensitivity and Noise Propagation in a Synthetic Transcriptional Cascade.", Proc. Natl. Acad. Sci. USA, vol. 102, No. 10, pp. 3581-3586, Mar. 8, 2005.
International Search Report and Written Opinion in International Application No. PCT/US16/26518, dated Apr. 7, 2016.
Jeong et al., "Anti-Tumoral Effect of the Mitochondrial Target Domain of Noxa Delivered by an Engineered *Salmonella typhimurium*.", PLOS One, vol. 9, Issue 1, 11 pages, Jan. 2014.
Jiang et al., "Inhibition of Tumor Growth and Metastasis by a Combination of *Escherichia coli*-mediated Cytolytic Therapy and Radiotherapy", Molecular Therapeutics, vol. 18, No. 3, pp. 635-642, 2010.
June, CH et al., "Engineered t Cells for Cancer Therapy", Cancer bnmunology, Immunotherapy, 1-7, 2014.
Keiler et al., "Role of a Peptide Tagging System in Degradation of Proteins Synthesized from Damaged Messenger RNA." Science 271, 990-993, 1996.
Kolnik et al., "Vacuum-Assisted Cell Loading Enables Shear-Free Mammalian Microfluidic Culture." Lab On a Chip 12, 4732-4737, 2012.
Leone V. et al., "Effects of diurnal variation of gut microbes and high-fat feeding on host circadian clock function and metabolism.", Cell Host & Microbe 17, pp. 681-689, May 13, 2015.
Lien et al., "Low-Dose Metronomic Chemotherapy: A Systematic Literature Analysis." European Journal of Cancer, pp. 3387-3395, 2013.
Loeffler et al., "*Salmonella typhimurium* engineered to produce CCL21 inhibit tumor growth", Cancer Immunology lmmunotherapy, 58, pp. 769-775, 2009.
Loessner et al., "Remote Control of Tumour-Targeted *Salmonella enterica* Serovar Typhimuriurn by the Use of 1-Arabinose as Inducer of Bacterial Gene Expression in vivo.", Cellular Microbiology 9, pp. 1529-1537, 2007.
Lutz et al., "Independent and Tight Regulation of Transcriptional Units in *Escherichia coli* via the lacr/o, the tetr/o and arac/il-i2 Regulatory Elements.", Nucleic Acids Research, vol. 25, No. 6, pp. 1203-1210, 1997.
Marguet et al.,"Oscillations by Minimal Bacterial Suicide Circuits Reveal Hidden Facets of Host-Circuit Physiology.", PLOS one, vol. 5, Issue. 7, Jul. 2010.
Mather et al., "Delay-induced degrade-and-fire oscillations in small genetic circuits", Physical Rev. Letters, 102, 068105, 2009.
McGinness et al., "Engineering controllable protein degradation.", Mol. Cell 22, pp. 701-707, Jun. 9, 2006.
Meighen, E. A., "Genetics of bacterial bioluminescence", Annual review of genetics, 28, pp. 117-139, 1994.
Merrikh et al., "A DNA Damage Response in *Escherichia coli* Involving the Alternative Sigma Factor, RpoS.", Proc. Natl. Acad Sci. USA, vol. 106, No. 2, pp. 611-616, Jan. 13, 2009.
Miest et al., "New Viruses for Cancer Therapy: Meeting Clinical Needs.", Nature Reviews Microbiology 12, pp. 23-34, 2014.
Mika, et al., "A Two-Component Phosphotransfer Network Involving ArcB, Arc.A, and RssB Coordinates Synthesis and Proteolysis of crS (RpoS) in *E coli*.", Genes & Dev. 19, pp. 2770-2781, 2005.
Mondragon-Palornino et al., "Entrainment of a population of synthetic genetic oscillators", Science Signaling 333, pp. 25 pages, 2011.
Moon et al., "Genetic Programs Constructed From Layered Logic Gates in Single Cells.", Nature 491, pp. 249-253, 2012.
Mukherji et al., "MicroRNAs can generate thresholds in target gene expression.", Nature Genet., 43, pp. 854-859, 2011.
Muller et al., "Cell-cell communication by quorum sensing and dimension-reduction", Journal of Mathematical Biology 53, pp. 672-702, 2005.
Nandagopal et al., "Synthetic Biology: Integrated Gene Circuits.", Science, 333, pp. 1244-1248, 2011.

(56) References Cited

OTHER PUBLICATIONS

Nguyen et al., Genetically Engineered *Salmonella typhirnurium* as an Imageable Therapeutic Probe for Cancer., Cancer Research 70, pp. 18-23, 2010.
O'Shea, CC., "Viruses Seeking and Destroying the Tumor Program.", Oncogene, 24, pp. 7640-7655, 2005.
Parsek et al., "Acyl-homoserine lactone quorum sensing in gram-negative bacteria: a signaling mechanism involved in associations with higher organisms.", PNAS, vol. 97, pp. 8789-8793, 2000.
Paton et al., "Bioengineered microbes in disease therapy", Trends in molecular medicine, 18, 7, pp. 417-425, 2012.
Pawelek et al., "Tumor-Targeted *Salmonella* as a Novel Anticancer Vector.", Cancer Research 57, pp. 4537-4544, Oct. 15, 1997.
Pedelacq, et al., "Engineering and Characterization of a Superfolder Green Fluorescent Protein", Nature Biotechnology, 24, pp. 79-88, 2006.
Press, WH In Numerical Recipes: The Art of Scientific Computing 3rd ed. Cambridge Univ. Press), 1262 pages, 2007.
Prindle et al., "Genetic Circuits in *Salmonella typhimurium*.", ACS SyntheticBiology, 1, pp. 458-464, 2012.
Prindle et al., "A Sensing Array of Radically Coupled Genetic 'biopixels'", Nature, 481, pp. 39-44, 2012.
Prindle et al., "Rapid and Tunable Post-Translational Coupling of Genetic Circuits", Nature, 508, pp. 387-391, 2014.
Pruteanu et al., "The Cellular Level of the Recognition Factor RssB is Transduction in aS Turnover in *Escherichia coli*.", Mol. Microbiol., 45, pp. 1701-1713, 2002.
Purcell et al., "Temperature Dependence of Ssra-Tag Mediated Protein Degradation.", Journal of Biological Engineering, 6, 10, 3 pages, 2012.
Quan et al., "Circular Polymerase Extension Cloning of Complex Gene Libraries and Pathways.", PloS one, vol. 4, issue 7, Jul. 2009.
Riedel et al., "Construction of p16slux, a novel vector for improved bioluminescent labeling of gram-negative bacteria.", Applied and environmental microbiology, vol. 73, No. 21, pp. 7092-7095, 2007.
Roberts et al., "Intratumornl injection of Clostridium novyi-NT spores induces antitumor responses", Science translational medicine, 6, 249, 12 pages, 2014.
Rosenfeld et al., "Response Delays and the Structure of Transcription Networks."J. Mol. Biol., 329, pp. 645-654, 2003.
Ruder et al., "Synthetic Biology Moving into the Clinic", Science 333, pp. 1248-1252, 2011.
Ryan et al., "Bacterial Delivery of a Novel Cytolysin to Hypoxic Areas of Solid Tumors", Gene Therapy 16, pp. 329-339, 2009.
Sausville et al., "Contributions of human tumor xenografts to anticancer drug development.", Cancer Research, 66, pp. 3351-3354, 2006.
Schaefer et al., "A New Class of Homoserine Lactone Quorum-Sensing Signals.", Nature, 454, pp. 595-599, 2008.
Shaked et al., "Low-Dose Metronomic Combined With Intermittent Bolus-Dose Cydophosphamide is an Effective Long-Term Chemotherapy Treatment Strategy.", Cancer research 65, pp. 7045-7051, Aug. 15, 2005.
Siuti et al., "Synthetic Circuits Integrating Logic and Memory in Living Cells", Nature Biotechnol., 3, pp. 448-452, 2013.
Stecher et al., "Flagella and Chemotaxis are Required for Efficient Induction of *Salmonella enterica* Serovar Typhimurium Colitis in Streptomycin-Pretreated Mice.", Infection and Immunity, vol. 72, No. 7, pp. 4138-4150, 2004.
Stricker et al., "A Fast, Robust and Tunable Synthetic Gene oscillator", Nature, 456, pp. 516-519, 2008.
Strogatz S., "Nonlinear Dynamics and Chaos: with Applications to Physics, Biology, Chemisny and Engineering" (Perseus Books), 505 pages, 2001.
Swofford et al., "Quorum-sensing *Salmonella* Selectively Trigger Protein Expression within Tumors.", Proceedings of the National Academy of Sciences, vol. 112, No. 11, pp. 3457-3462, Mar. 17, 2015.
Thaiss et al., "Chronobiomics: The biological clock as a new principle in host-microbial interactions.", PLoS Pathogens, 5 pages, 2015.
Thakur et al., "Modelling Vemurafenib Resistance in Melanoma Reveals a Strategy to Forestall Drug Resistance", Nature, 494, pp. 251-255, 2013.
Tigges et al., "A Tunable Synthetic Mammalian Oscillator", Nature, 457, pp. 309-312, 2009.
Unger et al., "Monolithic Microfabricated Valves and Pumps by Multilayer Soft Lithography", Science, 288, pp. 113-116, 2000.
Waters et al., "Quorum Sensing: Cell-to-Cell Communication in Bacteria", Annu. Rev. Cell Dev. Biol., 21, pp. 319-346, 2005.
Weber et al.,"Emerging Biomedical Applications of Synthetic Biology", Nature Reviews Genetics, 13, pp. 21-35, 2012.
Wood et al., "Enhanced Plasmid Stability Through Post-Segregational Killing of Plasmid-Free cells.", Biotechnology techniques, 4, pp. 39-44, 1990.
Xie et al., "Multi-input RNAi-based Logic Circuit for Identification of Specific Cancer Cells", Science, 333, pp. 1307-1311, 2011.
Xuan et al., "Microbial Dysbiosis is Associated with Human Breast Cancer.", PloS One, vol. 9, issue 1, Jan. 2014.
Young et al., "Lytic Action of Cloned Phi x174 Gene e.", Journal of Virology, vol. 44, No. 3, pp. 993-1002, Dec. 1982.
Hasty et al., "Engineered gene circuits," Nature, 2002, 420:224-230.
Isaacs et al., "Prediction and measurement of an autoregulatory genetic module," PNAS, 2003, 100(13):7714-7719.

\* cited by examiner

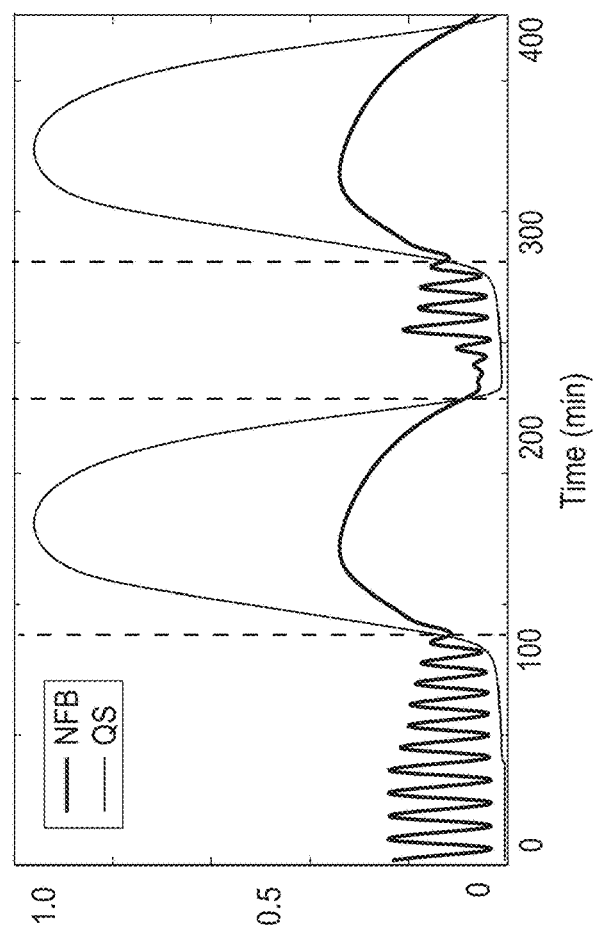
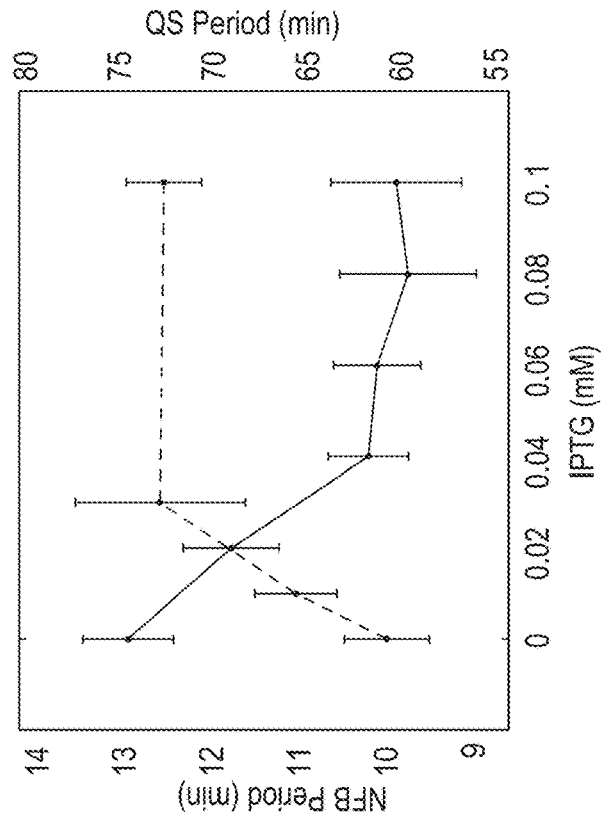
*FIG. 11C*
*FIG. 11D*

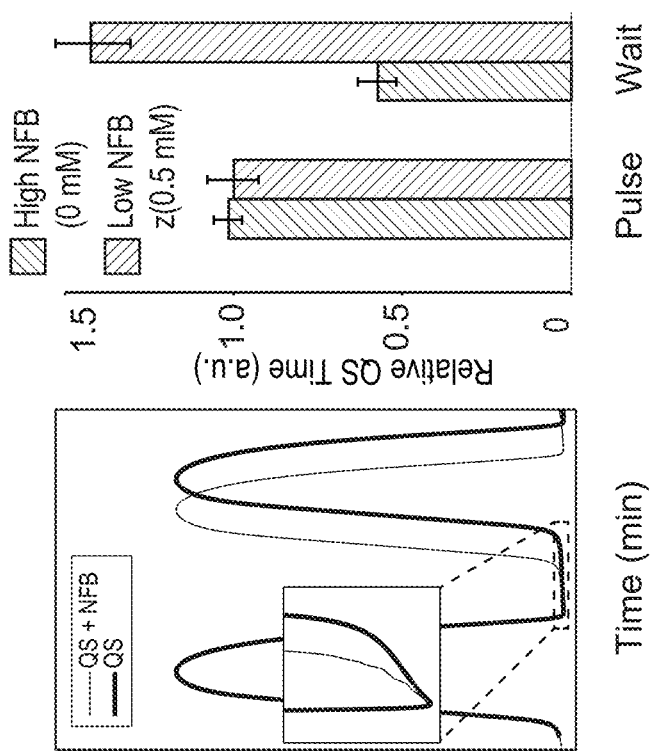
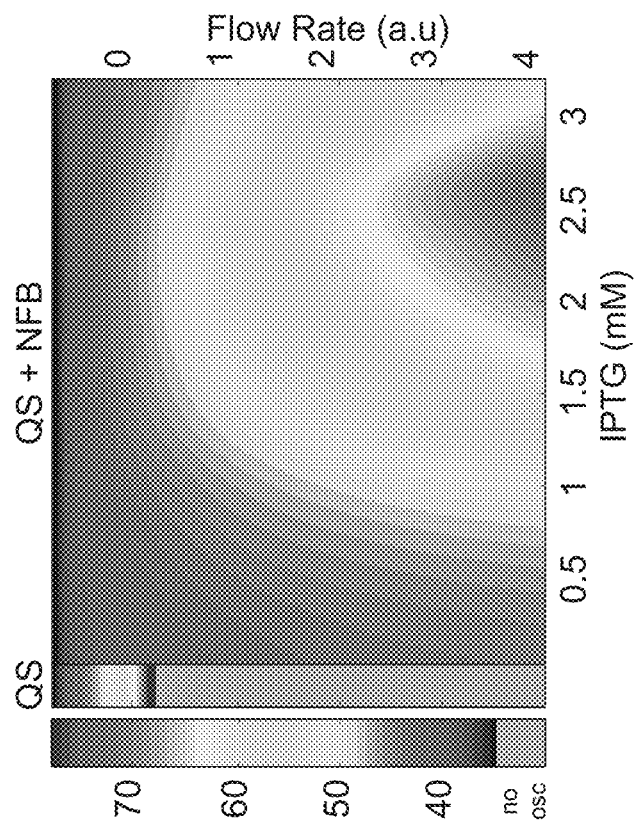
FIG. 11E
FIG. 11F

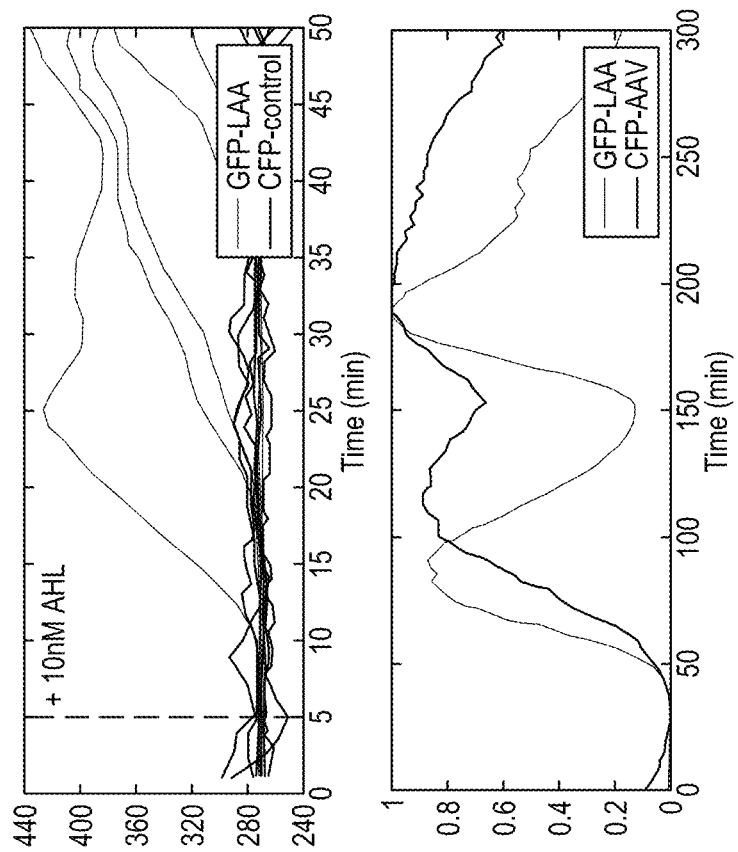
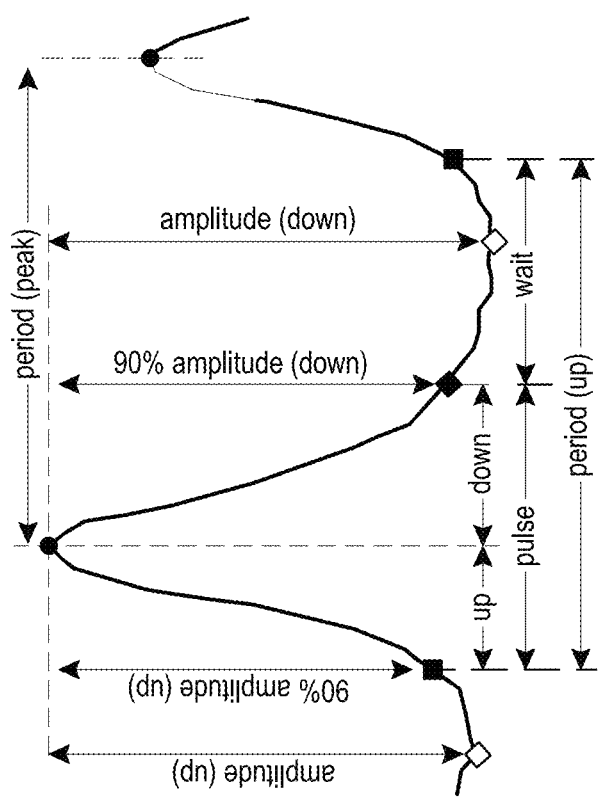
FIG. 14B
FIG. 14A 0 h   14 h   19 h   25 h   39 h   43 h   49 h   55 h   64 h   76 h   80 h

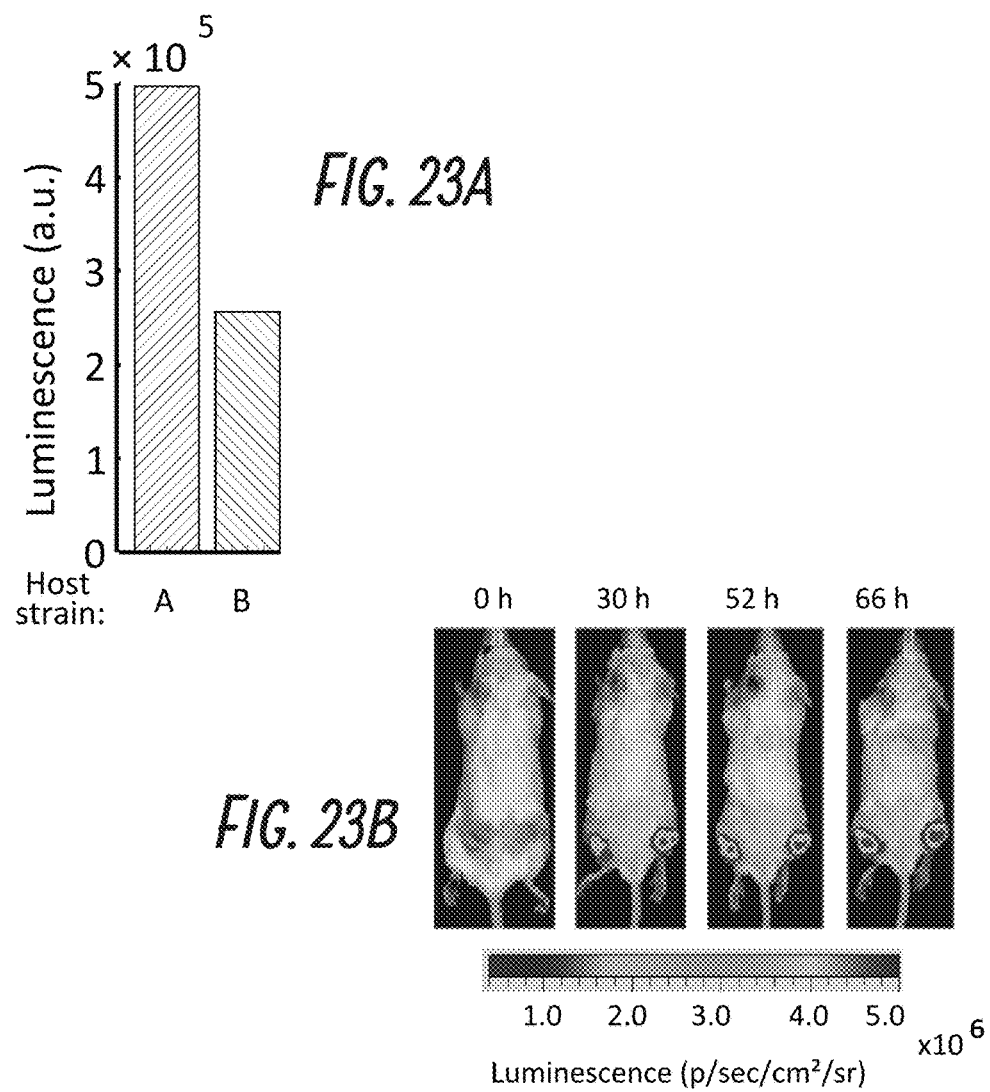
FIG. 23A
FIG. 23B
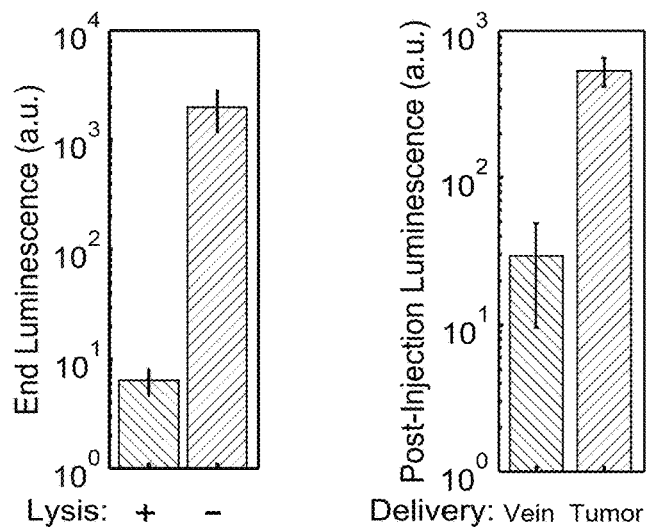
FIG. 23C
FIG. 23D

ENGINEERED BACTERIA FOR PRODUCTION AND RELEASE OF THERAPEUTICS

INCORPORATION BY REFERENCE TO ANY PRIORITY APPLICATIONS

This application is a U.S. National Phase Application of PCT International Application No. PCT/US2016/026518, filed on Apr. 7, 2016, designating the United States of America and published in the English language, which is an International Application of and claims the benefit of priority to U.S. Provisional Patent Application Ser. No. 62/145,417; filed on Apr. 9, 2015, the contents of which are hereby incorporated by reference under 37 CFR 1.57.

STATEMENT REGARDING FEDERALLY SPONSORED R&D

This invention was made with government support under GM069811, CA014051, and ES002109 awarded by the National Institutes of Health. The government has certain rights in the invention.

BACKGROUND

Field

Some embodiments described herein relate to cells which have been genetically engineered to release a polypeptide when a population of the cells reaches a desired density. In some embodiments, the released polypeptide may be a therapeutic polypeptide. In some embodiments, the therapeutic polypeptide kills tumor cells or inhibits the growth of tumor cells.

Description of the Related Art

Living therapies such as oncolytic viruses and engineered immune cells are emerging as alternatives in the treatment of cancer, with ongoing clinical trials for melanoma, carcinoma, and leukemia (O'Shea, C. C. Viruses-seeking and destroying the tumor program. *Oncogene* 24, 7640-7655 (2005); June, C. H. et al. Engineered t cells for cancer therapy. *Cancer Immunology, Immunotherapy* 1-7 (2014); Miest, T. S. & Cattaneo, R. New viruses for cancer therapy: meeting clinical needs. *Nature Reviews Microbiology* 12, 23-34 (2014)). Concurrently, the long-held monolithic view of bacteria as pathogens has given way to an appreciation of the widespread prevalence of functional microbes within the human body (Cho, I. & Blaser, M. J. The human microbiome: at the interface of health and disease. *Nature Reviews Genetics* 13, 260-270 (2012); Xuan, C. et al. Microbial dysbiosis is associated with human breast cancer. *PloS One* 9, e83744 (2014); Fischbach, M. A., Bluestone, J. A. & Lim, W. A. Cell-based therapeutics: the next pillar of medicine. *Science Translational Medicine* 5, 179ps7-179ps7 (2013)). Given this vast milieu, it is perhaps inevitable that certain bacteria would evolve to preferentially grow within tumors and thus provide a natural platform for the development of engineered therapies (Pawelek, J. M., Low, K. B. & Bermudes, D. Tumor-targeted *Salmonella* as a novel anticancer vector. *Cancer research* 57, 4537-4544 (1997); Ruder, W. C., Lu, T. & Collins, J. J. Synthetic biology moving into the clinic. *Science* 333, 1248-1252 (2011); Weber, W. & Fussenegger, M. Emerging biomedical applications of synthetic biology. *Nature Reviews Genetics* 13, 21-35 (2011)). While the localization of microbes within tumors has been exploited to stimulate the host immune system to target cancer cells, such therapies would ideally consist of bacteria that are programmed to safely avoid a systemic inflammatory response while continually producing anti-tumor agents that are locally released (Baban, C. K., Cronin, M., O'Hanlon, D., O'Sullivan, G. C. & Tangney, M. Bacteria as vectors for gene therapy of cancer. *Bioeng Bugs* 1, 385-394, 2010; Cann, S. H., Van Netten, J. & Van Netten, C. Dr William Coley and tumour regression: a place in history or in the future. *Postgraduate Medical Journal* 79, 672-680, 2003) Davila, M. L. et al. Efficacy and toxicity management of 19-28z CAR T cell therapy in B cell acute lymphoblastic leukemia. *Science Translational Medicine* 6, 224-224ra25, 2014). Among the embodiments described herein is the use of an engineered, clinically tested bacterium to lyse at a threshold population density and release a genetically encoded anti-tumor therapeutic. Upon lysis, a small number of surviving bacteria reseed the population, thus leading to pulsatile lysis and delivery cycles with a stealth in vivo footprint.

Recent advances in the forward engineering of genetic circuits have positioned synthetic biology as a novel approach for developing biological therapies (Fischbach, M. A., Bluestone, J. A. & Lim, W. A. Cell-based therapeutics: the next pillar of medicine. *Science Translational Medicine* 5, 179 ps7-179ps7, 2013; Ruder, W. C., Lu, T. & Collins, J. J. Synthetic biology moving into the clinic. *Science* 333, 1248-1252, 2011; Weber, W. & Fussenegger, M. Emerging biomedical applications of synthetic biology. *Nature Reviews Genetics* 13, 21-35, 2011; and Folcher, M. & Fussenegger, M. Synthetic biology advancing clinical applications. *Current Opinion in Chemical Biology*, 2012). Given the widespread prevalence of beneficial microbes and their functional roles within the body, bacteria represent a natural platform for the development of biological therapies in the treatment of metabolic disorders, gastrointestinal disease, and cancer (Cho, I. & Blaser, M. J. The human microbiome: at the interface of health and disease. *Nature Reviews Genetics* 13, 260-270 (2012); Garrett, W. S. Cancer and the microbiota. *Science* 348, 80-86, 2015; Pawelek, J. M., Low, K. B. & Bermudes, D. Tumor-targeted *Salmonella* as a novel anticancer vector. *Cancer Research* 57, 4537-4544, 1997). With continued progress in the development of modules for therapeutic gene expression, an unexplored possibility is the construction of circuits which dynamically control colony growth and therapeutic expression (Jeong, J.-H. et al. Anti-tumoral effect of the mitochondrial target domain of noxa delivered by an engineered *Salmonella typhimurium*. *PloS One* 9, e80050, 2014; Loessner, H. et al. Remote control of tumour-targeted *Salmonella enterica* serovar *typhimurium* by the use of 1-arabinose as inducer of bacterial gene expression in vivo. Cellular Microbiology 9, 1529-1537, 2007; Swofford, C. A., Van Dessel, N. & Forbes, N. S. Quorum-sensing *Salmonella* selectively trigger protein expression within tumors. *Proceedings of the National Academy of Sciences* 112, 3457-3462, 2015). These engineered bacteria would ideally self-maintain their population density while continually producing and releasing therapeutic agents in situ. Among the embodiments described herein is the use of an engineered bacterium with clinically relevant characteristics to lyse synchronously at a threshold population density and to release genetically encoded therapeutics. Upon lysis, a small number of surviving bacteria reseed the growing population, thus leading to pulsatile lysis and release cycles.

SUMMARY

This section provides a general summary of the disclosure, and is not comprehensive of its full scope or all of its features. Some embodiments of the disclosure are described in the following numbered paragraphs:

1. A cell which has been genetically engineered to release a polypeptide when a population of said cells reaches a desired density.

2. The cell of Paragraph 1, wherein said cell is a bacterial cell.

3. The cell of any one of Paragraphs 1 to 2, wherein said polypeptide is a therapeutic polypeptide.

4. The cell of Paragraph 3, wherein said therapeutic polypeptide is a polypeptide which kills tumor cells or which inhibits the growth of tumor cells.

5. The cell of Paragraph 3, wherein said therapeutic polypeptide is a polypeptide which elicits immune responses against tumor cells.

6. The cell of Paragraph 3, wherein said therapeutic polypeptide is a polypeptide which recruits T-cell or dendritic cells.

7. The cell of Paragraph 3, wherein said therapeutic polypeptide is a polypeptide which causes or enhances apoptosis.

8. The cell of Paragraph 3, wherein said therapeutic polypeptide is a polypeptide which enhances the release and/or efficacy of an anti-cancer drug.

9. The cell of Paragraph 8, wherein said anti-cancer drug is a liposomal anti-cancer drug.

10. The cell of any one of Paragraphs 1 to 9, wherein said cell lyses when said population of said cells reaches said desired density.

11. The cell of any one of Paragraphs 1 to 10, wherein said cell is capable of proliferating within a tumor.

12. The cell of any one of Paragraphs 1 to 10, wherein said cell is capable of proliferating in a necrotic region of a tumor.

13. The cell of any one of Paragraphs 1 to 12, wherein said cell is an anaerobic cell.

14 The cell of any one of Paragraphs 1 to 13, wherein said cell has been genetically engineered to produce a polypeptide which lyses said cell when said population of said cells reaches said desired density.

15. The cell of Paragraph 14, wherein said polypeptide which lyses said cell comprises the ϕX174 E lysis polypeptide, the E7 lysis polypeptide from a colicin-producing bacterium, or a lambda phage lysis polypeptide.

16. The cell of Paragraph 15, wherein said polypeptide which lyses said cell comprises the ϕX174 E lysis polypeptide.

17 The cell of any one of Paragraphs 14 to 16, wherein said polypeptide which lyses said cell is under the control of a regulatable promoter.

18. The cell of Paragraph 9, wherein said cell produces a diffusible inducer which increases the strength of said regulatable promoter.

19. The cell of any one of Paragraphs 9 to 10, wherein said regulatable promoter comprises the luxI promoter or a functional fragment thereof.

20. The cell of Paragraph 18, wherein said diffusible inducer comprises acyl homoserine lactone.

21. The cell of Paragraph 20, wherein said acyl homoserine lactone is produced through the action of the luxI protein.

22. The cell of Paragraph 21, wherein the expression of said luxI protein is under the control of the luxI promoter.

23. The cell of any one of Paragraphs 20 to 22, wherein said acyl homoserine lactone binds to a luxR protein and said luxR protein activates transcription from said luxI promoter.

24. The cell of any one of Paragraphs 20 to 23, wherein the level of acyl homoserine lactone in said cell is regulated by the level of the AiiA protein in said cell.

25. The cell of Paragraph 24, wherein the expression of the AiiA protein is under the control of a regulatable promoter.

26. The cell of any one of Paragraphs 3 to 25 wherein said therapeutic polypeptide is encoded by a plasmid in said cell.

27. The cell of any one of Paragraphs 14 to 26 wherein said polypeptide which lyses said cell is encoded by a plasmid in said cell.

28. The cell of any one of Paragraphs 14 to 27 wherein said therapeutic polypeptide is encoded by a first plasmid in said cell and said polypeptide which lyses said cell is encoded by a second plasmid in said cell.

29. The cell of any one of Paragraphs 14 to 27, wherein said therapeutic polypeptide and said polypeptide which lyses said cell are encoded by the same plasmid in said cell.

30. The cell of any one of Paragraphs 10 to 29, wherein not all of the cells in said population are lysed when said population of cells is at said desired density, thereby allowing regrowth of said cells after lysis and facilitating pulsatile release of said therapeutic polypeptide.

31. The cell of any one of Paragraphs 18 to 30, wherein the level of said inducer is regulated by the same regulatable promoter as said polypeptide which lyses said cell.

32. The cell of any one of Paragraphs 3 to 31, wherein said therapeutic polypeptide comprises hemolysin E.

33. The cell of any one of Paragraphs 1 to 32, wherein said cell preferentially localizes within necrotic regions of a tumor.

34. The cell of any one of Paragraphs 1 to 33, wherein the timing of the release of said polypeptide is directly or indirectly coupled to the activity of a genetic circuit.

35. The cell of Paragraph 34, wherein said genetic circuit comprises a genetic circuit which regulates the activity of the ClpXP protease.

36. The cell of Paragraph 35, wherein said released polypeptide comprises a LAA tag.

37. The cell of any one of Paragraphs 35 to 36, wherein the level of activity of said ClpXP protease on said released polypeptide is regulated by the level of hydrogen peroxide.

38. The cell of any one of Paragraphs 10 to 37, wherein the timing of the lysis of said cell is directly or indirectly coupled to the activity of a genetic circuit.

39. The cell of Paragraph 38, wherein said genetic circuit coupled to the timing of the lysis of said cell comprises a genetic circuit which regulates the activity of the ClpXP protease.

40. The cell of Paragraph 39, wherein a polypeptide which lyses said cell comprises a LAA tag.

41. The cell of any one of Paragraphs 39 to 40, wherein the level of activity of said ClpXP protease on said polypeptide which lyses said cell is regulated by the level of hydrogen peroxide.

42. A collection comprising a plurality of strains of the cells of any one of Paragraphs 1 to 41, wherein each strain releases a different polypeptide when said strain reaches said desired density.

43. The collection of Paragraph 42, wherein each strain in said plurality of strains is resistant to a different antibiotic.

44. The collection of Paragraph 42, wherein each strain in said plurality of strains produces a bacteriocin which acts on the other strains in said collection.

45. The collection of Paragraph 42, wherein at least one strain of said plurality of strains releases a polypeptide at a frequency different than the release frequency of at least one of the other strains in said collection.

46. A method of providing a polypeptide to an individual comprising administering a cell of any one of Paragraphs 1-41 to said individual under conditions which facilitate the release of said polypeptide by said cell in said individual.

47. A method of treating a health condition in an individual comprising administering a cell of any one of claims 1 to 41 to said individual wherein said polypeptide is a therapeutic polypeptide.

48. The method of any one of Paragraphs 46 to 47, wherein said polypeptide is a polypeptide which kills or inhibits the growth of a tumor and wherein said cells are administered in a fashion which delivers said cells to said tumor.

49. The method of any one of Paragraphs 46 to 47, wherein said polypeptide is released in said individual in a pulsatile manner.

50. The method of any one of Paragraphs 46 to 49, further comprising administering a second therapeutic agent to said individual.

51. The method of Paragraph 50, wherein said second therapeutic agent is administered to said individual concurrently with administration of said cell of any one of claims 1 to 41 to said individual.

52. The method of Paragraph 50, wherein said second therapeutic agent is administered to said individual at a different time than administration of said cell of any one of claims 1 to 41 to said individual.

53. The method of Paragraph 50, wherein said second therapeutic agent is chemotherapeutic agent or a biological therapeutic agent.

54. The method of Paragraph 53, wherein said second therapeutic agent comprises 5-fluorouracil.

55. A method of providing a plurality of polypeptides to an individual comprising administering a collection comprising a plurality of strains of cells of any one of Paragraphs 42 to 45 to said individual under conditions which facilitate the release of each of said different polypeptides by said plurality of strains in said individual.

56. The method of Paragraph 55, wherein at least one of said different polypeptides is a therapeutic polypeptide which kills or inhibits the growth of a tumor and wherein said collection comprising said plurality of strains of said cells is administered in a fashion which delivers said plurality of strains of said cells to said tumor.

57. The method of Paragraph 56, wherein said therapeutic polypeptide is a polypeptide which elicits immune responses against tumor cells.

58. The method of Paragraph 56, wherein said therapeutic polypeptide is a polypeptide which recruits T-cell or dendritic cells.

59. The method of Paragraph 56, wherein said therapeutic polypeptide is a polypeptide which causes or enhances apoptosis.

60. The method of Paragraph 56, wherein said therapeutic polypeptide is a polypeptide which enhances the release and/or efficacy of an anti-cancer drug.

61. The cell of Paragraph 60, wherein said anti-cancer drug is a liposomal anti-cancer drug.

62. The method of any one of Paragraphs 55 to 61 wherein each of said different polypeptides is released in said individual in a pulsatile manner.

63. The method of any one of Paragraphs 55 to 62, wherein a first strain in said plurality of strains is administered to said individual and allowed to proliferate for a desired period of time and a second strain in said plurality of strains is subsequently administered to said individual and allowed to proliferate for a desired period of time, wherein the proliferation of said first strain is prevented or inhibited as a result of the administration of said second strain.

64. The method of Paragraph 631, wherein said first strain is resistant to a first antibiotic and sensitive to a second antibiotic and said second strain is resistant to said second antibiotic and sensitive to said first antibiotic and wherein said first antibiotic is administered to said individual when proliferation of said first strain is desired and said second antibiotic is administered to said individual when proliferation of said second strain is desired.

65. The method of Paragraph 63, wherein said first strain produces a first bacteriocin which kills or inhibits the growth of a second strain and said second strain produces a bacteriocin which kills or inhibits the growth of said first strain.

66. The method of any one of Paragraphs 55 to 65, wherein each of said strains in said plurality of strains is administered to said individual in a cyclic manner.

67. The method of any one of Paragraphs 55 to 66, wherein the proliferation of only one of said plurality of strains in said individual is facilitated at a time while the proliferation of the other strains in said plurality of strains is prevented or inhibited.

68. Use of a cell of any one of Paragraphs 1 to 41 to provide a polypeptide released from said cell to an individual.

69. Use of a cell according to any one of Paragraphs 1 to 41 for treating a health condition in an individual treating a health condition in an individual.

70. Use a collection comprising a plurality of strains of the cells of any one of claims 1 to 41 to provide a plurality of polypeptides to an individual.

71. The use of any one of Paragraphs 68 to 70, wherein said polypeptide is a therapeutic polypeptide.

72. The use of Paragraph 71, wherein said therapeutic polypeptide is a polypeptide which kills tumor cells or which inhibits the growth of tumor cells.

73. The use of Paragraph 71, wherein said therapeutic polypeptide is a polypeptide which elicits immune responses against tumor cells.

74. The use of Paragraph 71, wherein said therapeutic polypeptide is a polypeptide which recruits T-cell or dendritic cells.

75. The use of Paragraph 71, wherein said therapeutic polypeptide is a polypeptide which causes or enhances apoptosis.

76. The use of Paragraph 71, wherein said therapeutic polypeptide is a polypeptide which enhances the release and/or efficacy of an anti-cancer drug.

77. The use of Paragraph 76, wherein said anti-cancer drug is a liposomal anti-cancer drug.

78. The use of any one of Paragraphs 68 to 77, wherein said polypeptide is released in said individual in a pulsatile manner.

79. The use of any one of Paragraphs 68 to 78, further comprising administering a second therapeutic agent to said individual.

80. The use of Paragraph 79, wherein said second therapeutic agent is administered to said individual concurrently with administration of said cell of any one of claims 1 to 41 to said individual.

81. The use of Paragraph 79, wherein said second therapeutic agent is administered to said individual at a different time than administration of said cell of any one of claims 1 to 41 to said individual.

82. The use of Paragraph 79, wherein said second therapeutic agent is a chemotherapeutic agent or a biological therapeutic agent.

83. The use of Paragraph 81, wherein said second therapeutic agent comprises 5-fluorouracil.

84. The use of Paragraph 70, wherein a first strain in said plurality of strains is administered to said individual and allowed to proliferate for a desired period of time and a second strain in said plurality of strains is subsequently administered to said individual and allowed to proliferate for a desired period of time, wherein the proliferation of said first strain is prevented or inhibited as a result of the administration of said second strain.

85. The use of Paragraph 84, wherein said first strain is resistant to a first antibiotic and sensitive to a second antibiotic and said second strain is resistant to said second antibiotic and sensitive to said first antibiotic and wherein said first antibiotic is administered to said individual when proliferation of said first strain is desired and said second antibiotic is administered to said individual when proliferation of said second strain is desired.

86. The use of Paragraph 84, wherein said first strain produces a first bacteriocin which kills or inhibits the growth of a second strain and said second strain produces a bacteriocin which kills or inhibits the growth of said first strain.

87. The use of any one of Paragraphs 70 to 86, wherein each of said strains in said plurality of strains is administered to said individual in a cyclic manner.

88. The use of any one of Paragraphs 70 to 87, wherein the proliferation of only one of said plurality of strains in said individual is facilitated at a time while the proliferation of the other strains in said plurality of strains is prevented or inhibited.

89. A method of making a cell of any one of Paragraphs 1 to 41 comprising introducing a nucleic acid encoding said released polypeptide into said cell via bacterial conjugation.

90. A method of making a cell of any one of Paragraphs 14 to 41 comprising introducing a nucleic acid encoding said polypeptide which lyses said cell into said cell.

91. The method of any one of Paragraphs 89 to 90, wherein the introduction of said nucleic acid is carried out via bacterial conjugation.

The foregoing summary is illustrative only and is not intended to be in any way limiting. In addition to the illustrative aspects, embodiments, and features described above, further aspects, embodiments, objects and features of the disclosure will become fully apparent from the drawings and the following detailed description and the claims.

BRIEF DESCRIPTION OF THE DRAWINGS

FIG. 14. Increasing the length of the TS linker sequence results in increasing downstream module degradation delay. (A) Detailed breakdown of single fluorescent trajectory analysis. Peaks are identified in closed circles, troughs in open diamonds, upslope 10% points in closed squares and downslope 10% points in closed diamonds. The two period measurements are peak to peak and the time between two successive 10% upslope points. (B) Top: sfGFP does not show bleed-over into the CFP fluorescence channel. Induction of sfGFP with 10 nM acyl-homoserine lactone (AHL, dashed line) showed increase in fluorescence of sfGFP, which was not detected in the CFP channel. Bottom: the use of the published AAV degradation tag (Andersen, J. B. et al. New unstable variants of green fluorescent protein for studies of transient gene expression in bacteria. *Appl. Environ. Microbiol.* 64, 2240-2246 (1998)) shows delay in the downstream module degradation of 15 min. (C) Without the TS linker sequence, there is very little delay in downstream module degradation. (D) Single TS linker sequence results in 10 min delay. (E) Double TS linker sequence results in 16 min delay, similar to that of AAV degradation sequence. (F) 5-TS linker sequence results in 25 min delay (data shown in C-F were used to generate FIG. 10C).

Figure 1A:
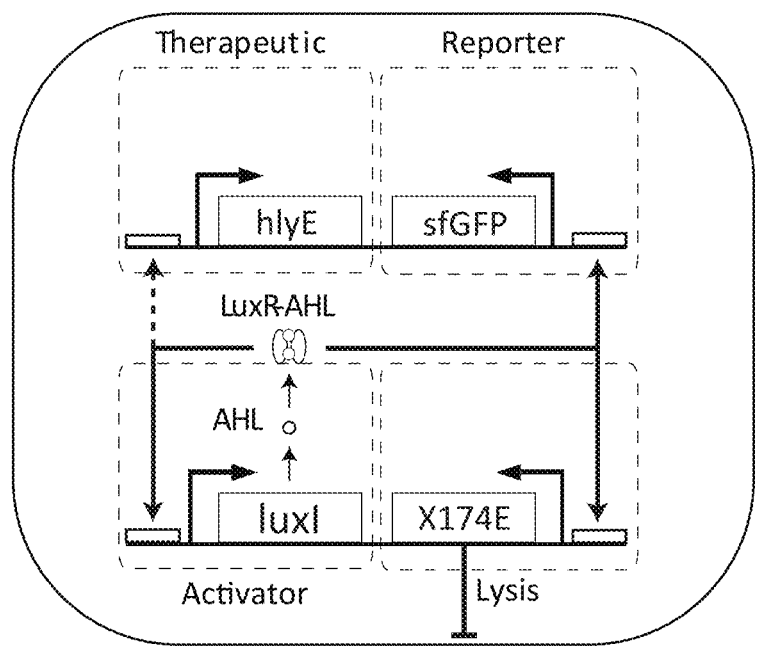
FIG. 1. Construction and characterization of one embodiment of the SLC. (A) The circuit contains an activator (Prindle, A. et al. A sensing array of radically coupled genetic 'biopixels'. Nature 481, 39-44, 2012) and lysis plasmid. When the population reaches the quorum threshold at a critical AHL concentration, the luxI promoter drives the transcription of gene E for lysis, LuxI, and sfGFP or luxCDABE as the reporter module. The luxI or the ptac promoter also drives the transcription of the therapeutic gene for the in vivo circuit. LuxR in this system is driven by the native pLuxR promoter. (B) A schematic that illustrates the main stages of each lysis cycle from seeding to quorum 'firing'. Shown at the bottom panels of the figure are typical time series images of the circuit-harboring cells undergoing the three main stages of quorum firing in a microfluidic growth chamber (Danino, T., Mondragón-Palomino, O., Tsimring, L. & Hasty, J. A synchronized quorum of genetic clocks. Nature 463, 326-330, 2010). (C) Fluorescence profile of a typical microfluidic experiment. The estimated cell population trajectory reveals that lysis events correspond to peaks of sfGFP fluorescence. (D) Period as a function of estimated flow velocity in the media channel of the microfluidic device and environmental temperature. Error bars indicate ±1 standard deviation for 13-50 peaks. The above experiments were performed with Strain 1 as described in Stecher, B. et al. Flagella and chemotaxis are required for efficient induction of Salmonella enterica serovar typhimurium colitis in streptomycin-pretreated mice. Infection and Immunity 72, 4138-4150 (2004), see Supplementary Information for complete strain information.

The foregoing and other features of the present disclosure will become more fully apparent from the following description and appended claims, taken in conjunction with the accompanying drawings. Understanding that these drawings depict only several embodiments in accordance with the disclosure and are not to be considered limiting of its scope; the disclosure will be described with additional specificity and detail through use of the accompanying drawings.

DETAILED DESCRIPTION OF THE DISCLOSURE

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and make part of this disclosure.

Some embodiments described herein relate to a genetic circuit which programs bacteria to exhibit dynamic lysis at high cell densities. This prunes the population and allows it to release genetically encoded therapeutic proteins. The bacteria that we use are genetically attenuated 'tumor-targeting' bacteria (which may have gene deletions for virulence genes such as PhoP, PhoQ, aroA, and msbB) which internalize inside tumors upon injection or feeding, and grow within the necrotic tissue. Since the engineered bacteria can only grow within the necrotic regions of the tumor, our circuit acts as a population sensor, specifically allowing payload release within the tumor.

In some embodiments, the strains can be engineered to produce an anti-tumor agent that can be genetically encoded. Non-limiting examples of genetically encoded anti-tumor agents include toxins such as hemolysin E, melittin, anti-microbial peptides, diphtheria toxins, gelonin toxins, and anthrax toxins. Other examples of genetically encoded anti-tumor agents include proteins and small molecules derived from non-bacterial sources, such as pro-apoptotic peptides and tumor homing peptides (such as cdd-iRGD), and proteins that elicit immune responses against cancer such as cytokines and chemokines (such as IL-2, CCL21, and the like). Described herein are three therapeutic strains, which are being tested combinatorially as combination therapies.

In some embodiments, methods for bacterial maintenance may be incorporated into the strains which produce therapeutic polypeptides. In some embodiments, at least one of the therapeutic polypeptides is a genetically encoded anti-tumor therapeutic polypeptide. For example, some embodiments utilize two or more strains each of produces a different therapeutic polypeptide and each of which is sensitive and resistant to different antibiotics than the other strains. For example, strain A may be resistant to antibiotic a and strain B may be resistant to antibiotic b. In some embodiments, therapy may be cyclically administered, such as every other day. For example, strain A and antibiotic a may be administered on Day 1, then strain B and antibiotic b on Day 2. This cycle may be repeated.

In some embodiments, bacteriocins may be employed. Such bacteriocins can be produced by the bacteria and then released at lysis to kill other bacteria (you can add resistance to a specific bacteriocin). For example, one embodiment is a three species system in which strain A produces a bacteriocin which kills strain B, strain B produces a bacteriocin which kills strains C, and strain C produces a bacteriocin which kills strain A. In one embodiment, strain C may be administered on day 1 then strain B on day 2 (clearing C), then strain A on day 3 (clearing B), then strain C, etc. This system has the further advantage of eliminating existing bacteria in the tumor environment, which can compete with the therapeutic bacteria.

Some embodiments employ multi-phasic delivery of the therapeutic polypeptides. For example, two orthogonal quorum sensing/lysis systems may be engineered in two strains of the same therapeutic bacteria or in two distinct therapeutic bacterial strains. The quorum sensing systems are orthogonal in that each system can function independently of the autoinducer from the others. In some embodiments, the quorum sensing systems described herein can include a variety of known systems in bacteria such as the Lux, Las, Rhl, or Rpa systems. These alternative systems can be configured on plasmids which then can subsequently be transformed into the bacteria. In some embodiments, the two strains with orthogonal quorum sensing systems can be used to deliver distinct therapeutic agents. In some embodiments, co-culture leads to one population delivering a therapeutic at one rate and another at a second rate, which can be achieved if the growth or circuit properties differ between the two orthogonal quorum sensing systems. Systems are not coupled since lysis occurs from the inside out. Further embodiments may include the following:

1. Use of a strain to deliver a therapy that is not as potent but which is a fast acting/transporting therapeutic which will serve to "weaken" the cancer cells by using a variation of our circuit that causes rapid or high frequency lysis. This can be combined with a strain that generates less frequent delivery or lysis of a potent but potentially slow-acting therapeutic. Timescales of different drug action are important—weaken defenses with one and then lower the hammer with the other. The frequency of lysis can be tuned by various approaches discussed in greater detail below. The high frequency and low frequency lysis strains can be strains transformed with the lysis circuit (SDC or SLC) with appropriate modifications for achieving the desired lysis frequency.

2. Use one strain to induce evolution of the cancerous cells such that they are more susceptible to therapy delivered by the second strain.

3. Co-existence of two strains. Two co-lysing systems lead to long term stability for two species of bacteria in the same culture. That is, two strains with orthogonal quorum sensing systems of differing periods driving lysis will result in a population where both strains co-exist in the co-culture. Neither population can take control because of the lysing. This can be visualized as the growth and lysis of the first strain to reach a quorum threshold within the co-culture. Once this first strain encounters a lysis event, its population is reduced allowing the second strain to grow and reach its lysis threshold. The second strain encounters lysis, thereby perpetuating the dynamics and co-existence of both strains.

In some embodiments, bacteria which already exist in the tumor may be adapted to release therapeutic proteins at a desired cell density. For example, in some embodiments, bacterial conjugation may be used to transform bacteria that are already in the tumor environment with the lysis circuit plus therapeutic(s). The native bacteria may then be enabled to kill the delivery bacteria (the messenger), such that you have transfected the lysis system into the bacteria that already reside in the tumor environment. We are exploring use of a promiscuous conjugation system for this purpose Some embodiments may utilize synchronized lysis across a large tumor environment to coordinate attack of multiple necrotic cores. For example, in some embodiment, the compositions and methods described in PCT Application No. PCT/US2012/069914, filed Dec. 14, 2012 and entitled "Multiscale platform for coordinating cellular activity using synthetic biology", the disclosure of which is incorporated herein by reference in its entirety, or the compositions and methods described in U.S. Provisional Patent Application Ser. No. 61/576,976, filed Dec. 16, 2011, the disclosure of which is incorporated herein by reference in its entirety, may be used. In particular, in some embodiments, synched oscillators over centimeter length scales may be used. In some embodiments, $H_2O_2$ long-range signaling is used to synchronize lysis bursts across tumor length scales. In such a context, there is no need for microfluidic "pixels" to house the colonies, since lysis defines the colony size without need for restrictive geometries. In addition to synchronized delivery across centimeter scales, there is potential for radicals to interact with cancer.

Some embodiments take advantage of the ability to construct sophisticated behavior in bacteria by the use of genetic circuits by engineering bacteria to exhibit oscillatory lysis. We use a genetic circuit motif for a genetic oscillator previously described by the Hasty group, where we utilize coupled negative and positive feedback loops. Population lysis allows us to keep the bacterial population low, helping us avoid a systemic inflammatory response. Since population lysis occurs periodically, the payload release also occurs in a pulsatile fashion. Additionally, the system only releases the internal payload in environments that allow the bacteria to reach a threshold size. Thus, some embodiments may be thought of as a tumor-targeting device capable of self-triggering in dense populations inside the tumor, releasing an internal payload, and maintaining the bacterial population at a low level to avoid deleterious immune responses.

The present compositions and methods provide advantages relative to other methods using simple expression of a therapeutic protein from an inducible promoter (either via chemical or environmental signal). As used herein, the terms "regulatable promoter", "inducible promoter" are used interchangeably and refer to any promoter the activity of which is affected by a cis or trans acting factor. In some embodiments, "regulatable promoter" refers to a promoter which is activated or repressed for transcription in response to external conditions such as the presence or absence of molecular control elements (e.g., acyl homoserine lactone—AHL) or pH or temperature. Regulatable promoters generally and specific examples are widely known and readily available Such other approaches do not rely on dynamic delivery, but more simply the constitutive production of a certain gene product. Also, such other approaches do not employ strategies for self-triggered population control (via lysis, for example) of the tumor-targeting bacteria.

Some embodiments involve recombinant plasmids which form the genetic circuit and consist of coupled positive and negative feedback genetic elements. For example, in some embodiments, the positive feedback genetic elements may utilize the Lux quorum sensing system (comprising of the LuxI and LuxR genes) driving gene expression from the LuxI promoter. This promoter allows transcription of the LuxI, lysis, and reporter genes. Therefore, once activated, this promoter then drives transcription of the negative feedback element, the lysis gene E from the bacteriophage ΦX174, and a fluorescent or luminescent reporter gene. A bacterial population harboring these circuit plasmids (engineered bacteria) will produce the LuxI protein which enzymatically produces AHL (acyl homoserine lactone), a small molecule that can diffuse between neighboring cells in the colony and synchronize the colony for pLuxI transcription (LuxI promoter). AHL subsequently binds to the LuxR protein which activates transcription from the LuxI promoter when the AHL concentration reaches a threshold level. Thus, the engineered bacterial population will grow to a threshold population size, at which point sufficient AHL has accumulated within the colony to activate transcription from the LuxI promoter, and produce the lysis protein. A fraction of the population will lyse, leaving behind a small colony size and thus reduced AHL concentrations. These surviving bacteria then re-grow to the threshold population size and exhibit another lysis event. This process continues in a periodic fashion. Upon lysis, the cells will release intracellular contents, including products of therapeutic genes, to the extracellular space. Therefore the population is dynamically attenuated while releasing an intracellular payload. See FIG. 1 for a diagram of the circuit and a schematic of the different stages described above.

In some embodiments, engineered tumor-targeting bacteria may be used to dynamically deliver therapeutic proteins to tumors and maintain a small in vivo footprint.

Some embodiments relate to methods, materials and devices/systems that pertain to bacteria programmed by a genetic circuit to exhibit dynamic lysis at high cell densities. This attenuates the population and allows it to release genetically encoded therapeutic proteins. The bacteria used may be attenuated 'tumor-targeting' bacteria which internalize inside tumors upon injection or feeding, and grow within the necrotic tissue. Since the engineered bacteria can only grow within the necrotic regions of the tumor, the circuit acts as a population sensor, specifically allowing payload release within the tumor.

In some embodiments, recombinant plasmids form the genetic circuit and comprise coupled positive and negative feedback genetic elements. Examples of suitable positive feedback genetic elements include, but are not limited to, the Lux quorum sensing system, and other quorum sensing systems such as the Las, Rhl, and Rpa systems (Waters, Christopher M., and Bonnie L. Bassler. "Quorum sensing: cell-to-cell communication in bacteria." *Annu. Rev. Cell Dev. Biol.* 21: 319-346, 2005, Schaefer, Amy L., et al. "A new class of homoserine lactone quorum-sensing signals." *Nature* 454: 595-599, 2008. Examples of suitable negative feedback genetic elements include, but are not limited to, any one of the lysis systems which can be used in bacteria, such as the lysis gene E from the bacteriophage ΦX174, the lambda phage lysis genes, the E7 lysis gene from colicin producing bacteria, and the like. In some embodiments described herein, the positive feedback genetic elements may comprise the Lux quorum sensing system (comprising the LuxI activator and LuxR genes) driving gene expression from the LuxI promoter. This promoter allows transcription of the LuxI, lysis, and reporter genes. Therefore, once activated, this promoter then drives transcription of the negative feedback element, which is for instance the lysis gene E from the bacteriophage ΦX174, and a fluorescent or luminescent reporter gene. A bacterial population harboring these circuit plasmids (engineered bacteria) will produce the LuxI protein which enzymatically produces AHL (acyl homoserine lactone) for the Lux system, a small molecule that can diffuse between neighboring cells in the colony and synchronize the colony for pLuxI transcription (LuxI promoter). Different AHL's act as autoinducers for the different quorum sensing systems such as the Las, Rhl, and Rpa systems. AHL subsequently binds to the LuxR protein (or respective R protein, such as LasR, RhlR, or RpaR) which activates transcription from the LuxI promoter when the AHL concentration reaches a threshold level. Thus, the engineered bacterial population will grow to a threshold population size, at which point sufficient AHL has accumulated within the colony to activate transcription from the LuxI promoter, and produce the lysis protein. A fraction of the population will lyse, leaving behind a small colony size and thus reduced AHL concentrations. These surviving bacteria then re-grow to the threshold population size and exhibit another lysis event. This process continues in a periodic fashion. Upon lysis, the cells will release intracellular contents, including products of therapeutic genes, to the extracellular space. Therefore the population is dynamically attenuated while releasing an intracellular payload.

The present compositions and methods provide advantages relative to methods using simple expression of a therapeutic protein from an inducible promoter (either via chemical or environmental signal). These other approaches do not rely on dynamic delivery, but more simply the constitutive production of a certain gene product. Also, such other approaches do not employ strategies for self-triggered population control (via lysis, for example) of the tumor-targeting bacteria.

Some embodiments utilize the genetic circuits described in "Rapid and tunable post-translational coupling of genetic circuits" Nature 508, 387-391 (17 Apr. 2014), by Arthur Prindle, Jangir Selimkhanov, Howard Li, Ivan Razinkov, Lev S. Tsimring & Jeff Hasty; Published online 9 Apr. 2014, the disclosure of which is incorporated herein by reference in its entirety. In some embodiments, the techniques and genetic circuits described in the foregoing publication can be used for the delivery of two different drugs and different frequencies in the methods and compositions described herein.

Living therapies such as oncolytic viruses and engineered immune cells are emerging as alternatives in the treatment of cancer, with ongoing clinical trials for melanoma, carcinoma, and leukemia (O'Shea, C. C. Viruses-seeking and destroying the tumor program. *Oncogene* 24, 7640-7655 (2005); June, C. H. et al. Engineered t cells for cancer therapy. *Cancer Immunology, Immunotherapy* 1-7 (2014); Miest, T. S. & Cattaneo, R. New viruses for cancer therapy: meeting clinical needs. *Nature Reviews Microbiology* 12, 23-34 (2014)). Concurrently, the long-held monolithic view of bacteria as pathogens has given way to an appreciation of the widespread prevalence of functional microbes within the human body (Cho, I. & Blaser, M. J. The human microbiome: at the interface of health and disease. *Nature Reviews Genetics* 13, 260-270 (2012); Xuan, C. et al. Microbial dysbiosis is associated with human breast cancer. *PloS one* 9, e83744 (2014); Fischbach, M. A., Bluestone, J. A. & Lim, W. A. Cell-based therapeutics: the next pillar of medicine. *Science translational medicine* 5, 179ps7-179ps7 (2013)). Given this vast milieu, it is perhaps inevitable that certain bacteria would evolve to preferentially grow within tumors and thus provide a natural platform for the development of engineered therapies (Pawelek, J. M., Low, K. B. & Bermudes, D. Tumor-targeted *salmonella* as a novel anticancer vector. *Cancer research* 57, 4537-4544 (1997); Ruder, W. C., Lu, T. & Collins, J. J. Synthetic biology moving into the clinic. *Science* 333, 1248-1252 (2011); Weber, W. & Fussenegger, M. Emerging biomedical applications of synthetic biology. *Nature Reviews Genetics* 13, 21-35 (2011)). While the localization of microbes within tumors has been exploited to stimulate the host immune system to target cancer cells, such therapies would ideally consist of bacteria that are programmed to safely avoid a systemic inflammatory response while continually producing anti-tumor agents that are locally released (Baban, C. K., Cronin, M., OŠHanlon, D., OŠSullivan, G. C. & Tangney, M. Bacteria as vectors for gene therapy of cancer. *Bioeng Bugs* 1, 385-394 (2010); Cann, S. H., Van Netten, J. & Van Netten, C. Dr William Coley and tumour regression: a place in history or in the future. *Postgraduate medical journal* 79, 672-680 (2003); Davila, M. L. et al. Efficacy and toxicity management of 19-28z car t cell therapy in b cell acute lymphoblastic leukemia. *Science translational medicine* 6, 224ra25-224ra25 (2014)). Here, we engineer a clinically tested bacterium to lyse at a threshold population density and release a genetically encoded anti-tumor therapeutic. Upon lysis, a small number of surviving bacteria reseed the population, thus leading to pulsatile lysis and delivery cycles with a stealth in vivo footprint. We use microfluidic devices to characterize the robust and tunable properties of the engineered bacteria, and we demonstrate their therapeutic potential when co-cultured with human cancer cells in microchemostats and batch culture, respectively. We test the stealth nature of the lysis program in a syngeneic colorectal mouse model of cancer using luciferase to monitor in vivo delivery dynamics. Punctuated luminescence peaks correlate with a 32-fold reduction in average colony luminescence compared to non-programmed strains, along with a 2-fold decrease in final tumor volume. Our platform may enable implementation of novel delivery strategies in conjunction with other therapeutic agents such as viruses and nanoparticles (Cheong, I. et al. A bacterial protein enhances the release and efficacy of liposomal cancer drugs. *Science* 314, 1308-1311 (2006)).

In order to engineer bacteria to maintain safe population levels within a tumor environment, we designed a stealth delivery circuit (SDC) using coupled positive and negative feedback loops that have previously been shown capable of generating robust oscillatory dynamics (Danino, T., Mondragón-Palomino, O., Tsimring, L. & Hasty, J. A synchronized quorum of genetic clocks. *Nature* 463, 326-330 (2010); Prindle, A. et al. A sensing array of radically coupled genetic 'biopixels'. *Nature* 481, 39-44 (2012)). The terms "synchronized lysis circuit" (SLC) and "stealth delivery circuit" (SDC) are used interchangeably in the present disclosure. In our circuit (FIG. 1A), a common promoter drives expression of both its own activator (positive feedback) and a lysis gene (negative feedback), respectively. For example, the luxI promoter regulates production of autoinducer (AHL), which binds LuxR and enables it to transcriptionally activate the promoter. This would also be the case for other quorum sensing systems from bacteria with their respective AHL, R protein, and activator protein. Examples of such components include, RhlR, LasR, LasI, or RhlI.

Negative feedback arises from cell death that is triggered by a cellular lysis gene (which can be, for example, φX174E, E7 lysis gene, or other lysis genes from phage lambda) that is also under control of the LuxI promoter (Prindle, A. et al. A sensing array of radically coupled genetic 'biopixels'. *Nature* 481, 39-44 (2012); Young, K. D. & Young, R. Lytic action of cloned phi x174 gene e. *Journal of virology* 44, 993-1002 (1982); Marguet, P., Tanouchi, Y., Spitz, E., Smith, C. & You, L. Oscillations by minimal bacterial suicide circuits reveal hidden facets of host-circuit physiology. *PloS one* 5, e11909 (2010)). Importantly, the AHL can diffuse to neighboring cells and thus provides a intercellular synchronization mechanism.

Figure 1B:
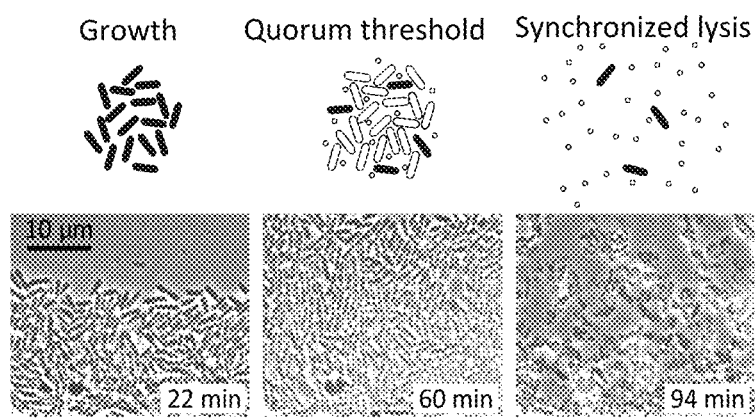
Figure 1C:
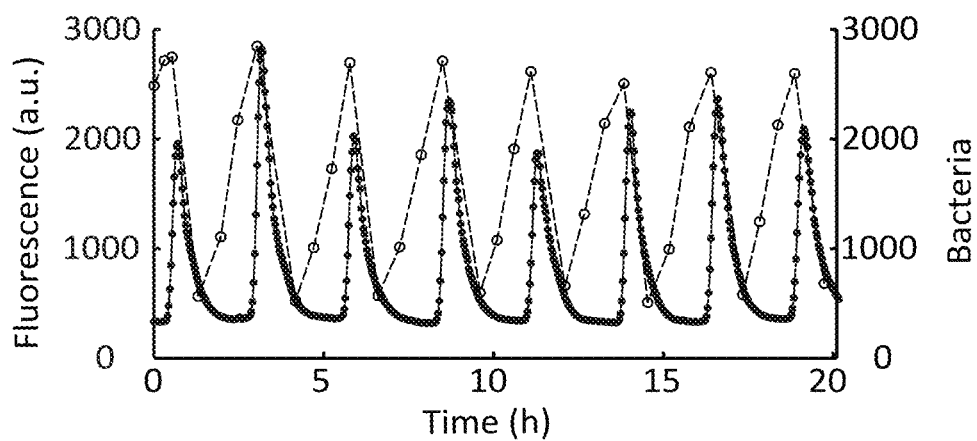
Figure 1D:
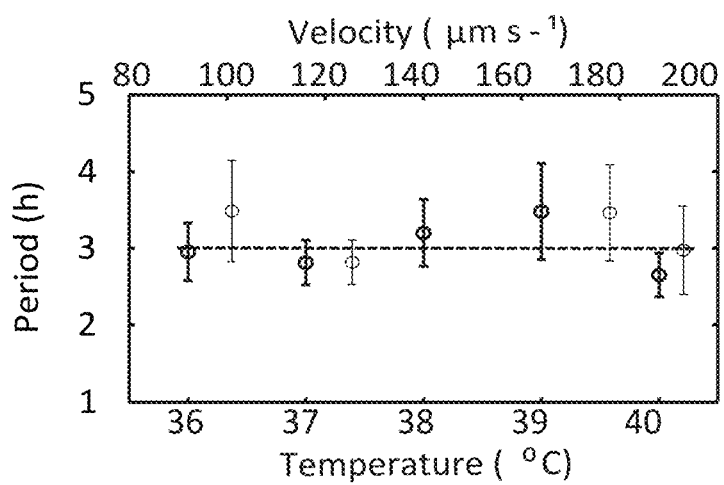
Figure 5A:
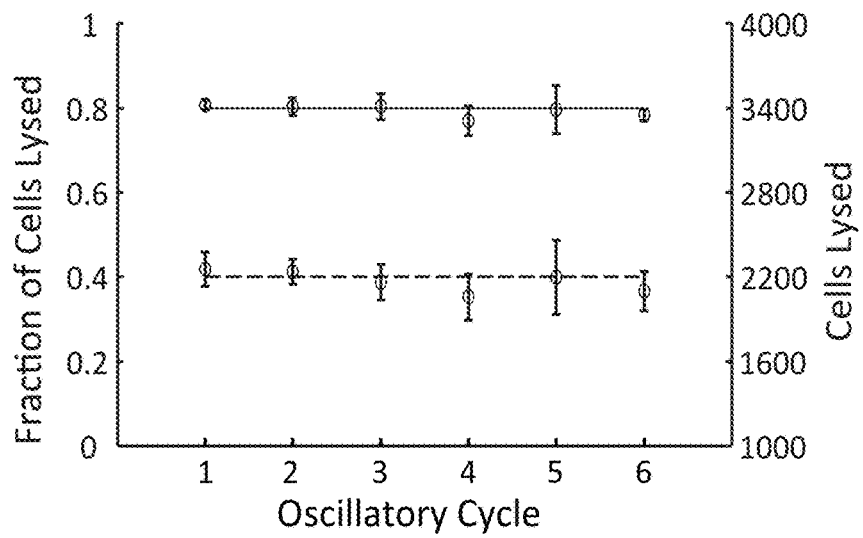
FIG. 5. Circuit robustness in different bacterial hosts. (A) The fraction and number of bacterial cells lysed per consecutive oscillatory cycle in the growth chamber for a typical microfluidic experiment for *S. typhimurium* (Strain 1). Solid line: Fraction of cells lysed. Dashed line: Cells lysed. (B) Period as a function of estimated flow velocity in the media channel of the microfluidic device for *E. coli*. Error bars indicate ±1 standard deviation for 12-19 peaks. (C) Period as a function of the environmental temperature for *E. coli*. The circuit does not oscillate for temperatures above 37° C. in *E. coli*. Error bars indicate ±1 standard deviation for 12-19 peaks. Experiments in (b) and (c) were performed with Strain 13. (D) Fluorescent profile showing circuit behavior for ssrA (solid line and closed circles, Strain 13), TS-ssrA (dashed line and open circles, Strain 15), and non-ssrA (dashed line and closed circles, Strain 14) tagged LuxI versions of the circuit in *E. coli*. The period is not tunable using the variable degradation tag strategy in *E. coli* as the circuit loses oscillatory behavior with reduced degradation efficiency. (E) The region in the flow and temperature parameter space in which the circuit exhibits oscillatory behavior. The strain parameters for *S. typhimurium* give a wider region which allows for robust oscillations (see additional information herein). Heatmap colors correspond to the period of the oscillations.
Figure 5B:
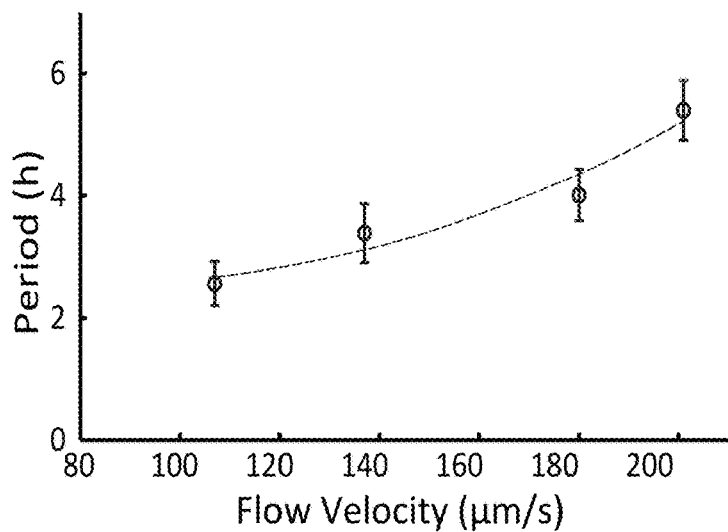
Figure 5C:
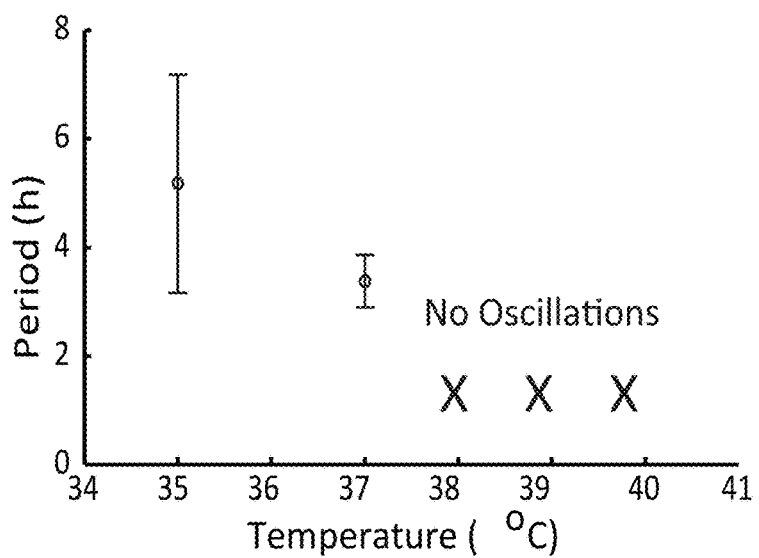
Figure 5D:
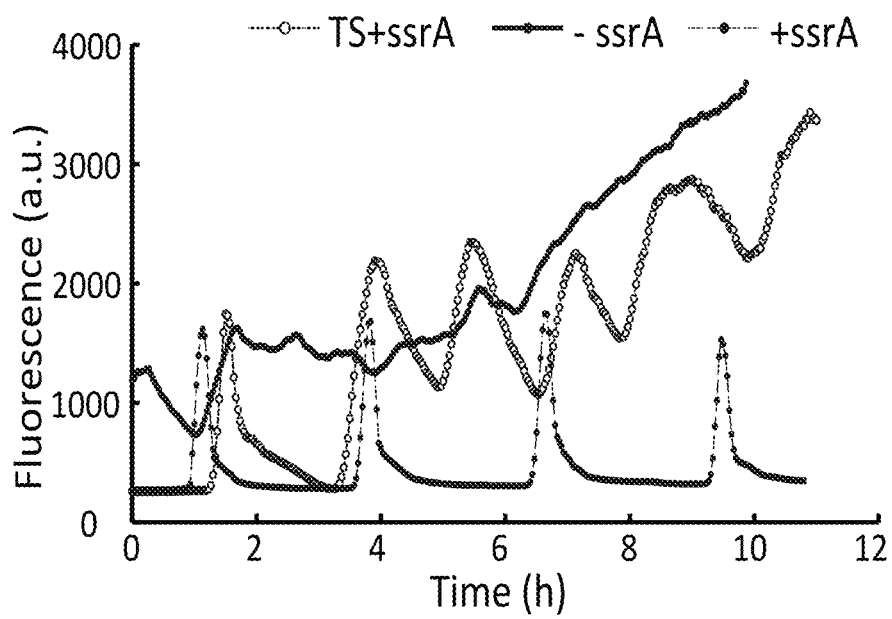

The dynamics arising from the stealth delivery circuit can be conceptualized as the slow buildup of AHL to a threshold level, followed by a lysis event that rapidly prunes the population and enables the release of bacterial contents (FIG. 1B). After lysis, a small number of remaining bacteria begin to produce AHL anew and the process is repeated in a cyclical fashion. We used microfluidic devices to observe growth, lysis, and protein release with sfGFP as a proxy for therapeutic expression. Testing our circuit in attenuated *S. typhimurium*, we observed periodic lysis events in a microfluidic chamber, where peaks in the fluorescent reporter profile correspond to population lysis (FIG. 1C). The oscillations were robust and did not decay with time, producing consistent population sizes that varied by less than 5% in total cell number over 18 hours of growth (FIG. 5A). In addition, since the in vivo microenvironment is characterized by fluctuating environmental conditions, we tested variable incubation temperatures (36° C. to 40° C.) and perfusion rates (100 μm/s to 200 μm/s), measuring an average period of 3 hours across all conditions (FIG. 1D). The results of these experiments are further summarized in the discussion of Supplementary Videos 1, 2, and 3 provided herein. We therefore expected the SDC to generate robust cycles of lysis and release in the face of environmental perturbations likely to be encountered in the in vivo context.

Figure 2A:
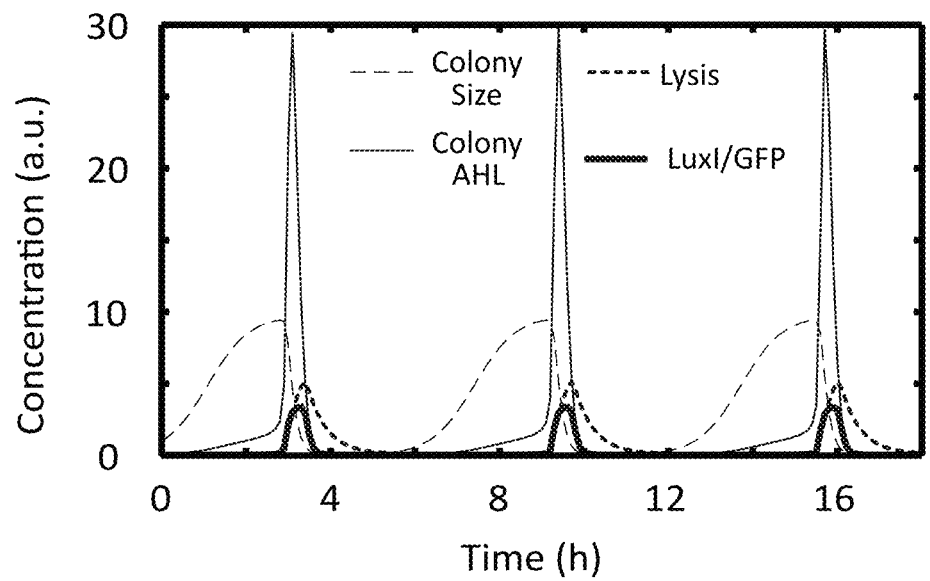
FIG. 2. Computational modeling and tunability. (A) A time series of colony size, colony AHL, intracellular concentration of single cell sfGFP or LuxI, and intracellular concentration of single-cell lysis protein for a bacterial colony from the computational model. (B) Results from the computational model showing the ability to tune the oscillatory period by varying ClpXP mediated degradation of LuxI. Solid line: colony size; Dashed line: intracellular concentration of single-cell lysis protein. (C) Fluorescence profiles showing lysis oscillations for LuxI ssrA (line connecting solid circles, Strain 2) and non-ssrA (line connecting open circles, Strain 1) tagged versions of the circuit. (D) The behavior of the circuit under saturating and non-saturating AHL conditions and model prediction (inset). Steady-state lysis behavior under 200 nM AHL is characterized by a steady fluorescence output, while the removal of AHL returns the system to oscillatory behavior (Strain 1). Dashed line: AHL concentration. Solid line: Fluorescence.

We developed a computational model to explore the parameters affecting the robustness of the SDC (FIG. 2A and Supplementary Information). We found that high production and degradation rates resulted in a wider domain of oscillatory dynamics in the parameter space. This explained our observations that oscillations in *S. typhimurium* were more robust than in *E. coli*, where rates of protein production and degradation were found to be lower (Prindle, A. et al. Genetic circuits in *Salmonella typhimurium*. *ACS synthetic biology* 1, 458-464 (2012)) (FIG. 5B-E). Thus, the robust behavior of the circuit ultimately relies on the inherent parameters of the host bacterium.

Figure 2B:
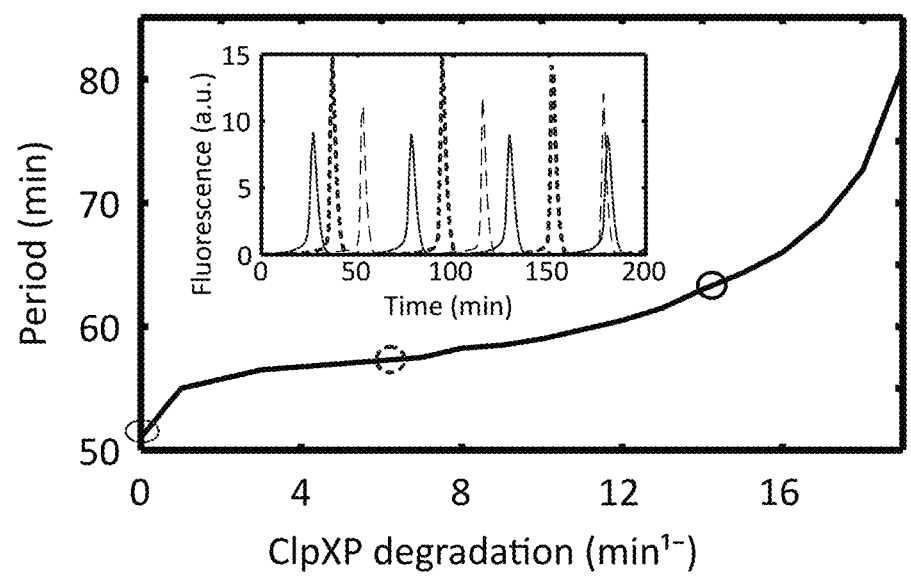
Figure 2C:
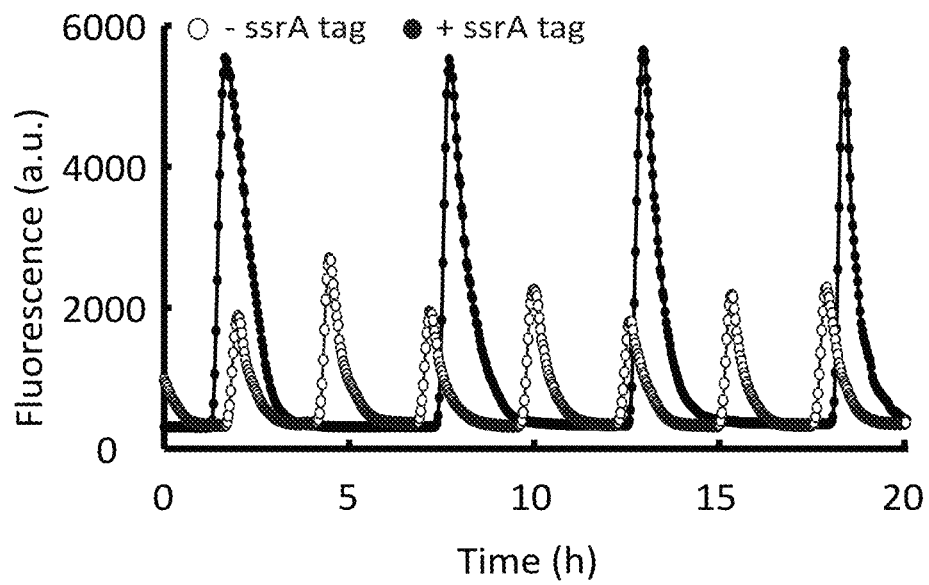
Figure 2D:
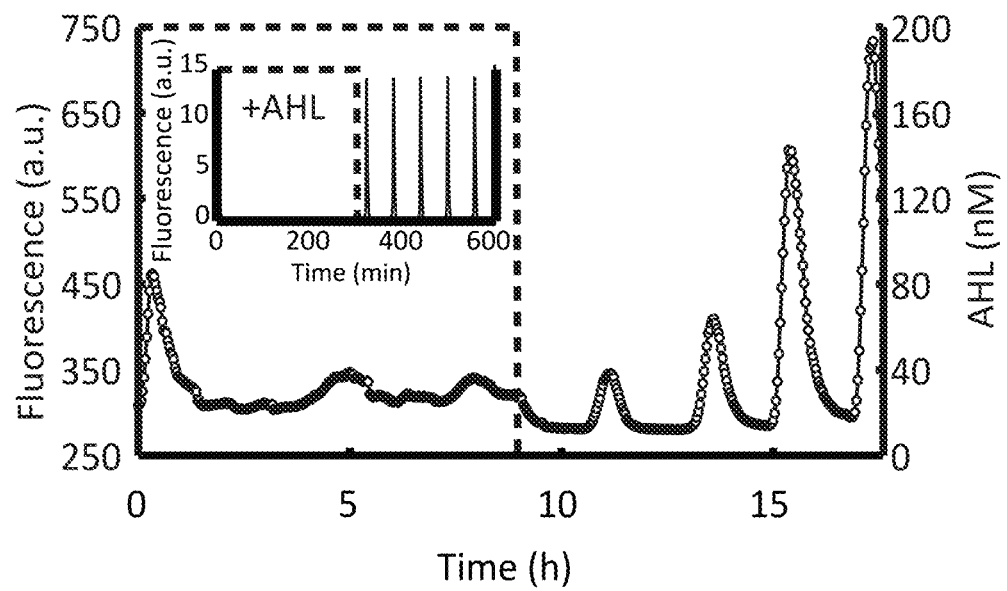

Since the ability to manipulate circuit behavior greatly enhances the versatility to apply our system in different contexts, we explored the tunability of the lysis period by adding an ssrA degradation tagging sequence on the LuxI protein. We observed a ~3-fold increase in the expression amplitude and a ~2-fold increase in the period, consistent with model predictions (FIG. 2B-C). We also explored the tunability of the circuit behavior via chemical induction by extracellular AHL. Our computational model predicted 'steady' population lysis at saturating concentrations (FIG. 2D, inset). In addition or alternatively, a number of suitable approaches and techniques can also be used to modify the period of the cycle, including modifying the growth rate of the bacteria, the promoter strengths, the ribosome binding site (RBS) strengths, and/or using different quorum sensing systems.

Testing the circuit under high concentrations of AHL, we observed that cell growth and lysis appeared to be balanced, reverting back to oscillatory behavior upon the removal of extracellular AHL (FIG. 2D. The results of these experiments were further documented in a video (Supplementary Video 4), which depicts timelapse fluorescence microscopy of the SDC in Strain 1 (*S. typhimurium*) at 60× magnification. This video shows that, in the first part of the experiment, media with 200 nM AHL was used and the bacteria could be seen entering a constant lysis state. In the device, indicated by fluorescent dye (red channel). The media was then switched to another source without AHL, in which the fluorescent dye was absent, and the bacteria reverted back to an oscillatory state, where the colony continued for 4 lysis cycles before the end of imaging. The chamber size was 100×100 μm and images were taken every 2 min. The SDC thus represents a versatile system capable of exhibiting oscillatory and constitutive modes of population lysis.

Figure 3A:
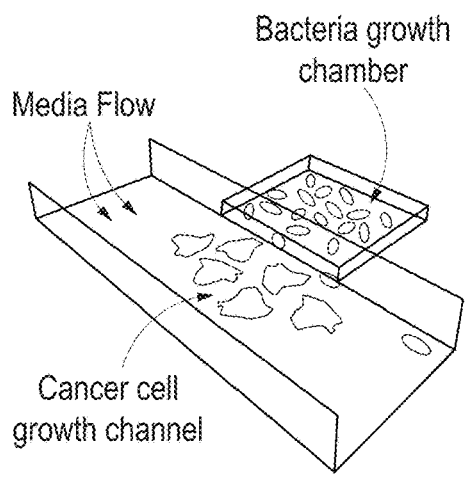
FIG. 3. In vitro therapeutic characterization. (A) Schematic of the microfluidic co-culture with cancer cells and bacteria. Fluidic resistance was modified in this chip to achieve stable near-stagnant flow reduction to allow for cancer cell adherence and for diffusion of released therapeutic from the trap to the channel (see methods in Supplementary Information). (B) Frames from the co-culture time series sequentially visualizing S. typhimurium (Strain 3) 'firing', lysis, and HeLa cell death. (C) Fluorescent profile (open circle) of the bacteria and HeLa cell viability (closed circle) fraction (number of live cells/number of dead cells in image frames) from (B) with time. (D) % viability of HeLa cells co-cultured with supernatant from S. typhimurium culture harboring the SLC+HlyE circuit (Strain 4), the SLC only circuit (Strain 5), constitutive hlyE only (Strain 6), or no plasmid (Strain 7). Error bars indicate ±1 standard error averaged over three measurements. (E) Fluorescence profile of the SLC+HlyE circuit (Strain 4) co-cultured with HeLa cells at various initial seeding densities. The black 'x' marks the point of complete HeLa cell death. (F) The toxin exposure time, measured from the initial presence of fluorescence to HeLa cell death, as a function of the sfGFP production rate (see example in (E)). Although the time to death depends on seeding, the total magnitude of exposure remains conserved (inset). Error bars indicate ±1 standard error for three measurements. See Supplementary Information for ELH1301 host strain information (Hohmann, E. L., Oletta, C. A. & Miller, S. I. Evaluation of a phop/phoq-deleted, aroa-deleted live oral *Salmonella typhi* vaccine strain in human volunteers. *Vaccine* 14, 19-24, 1996).
Figure 3B:
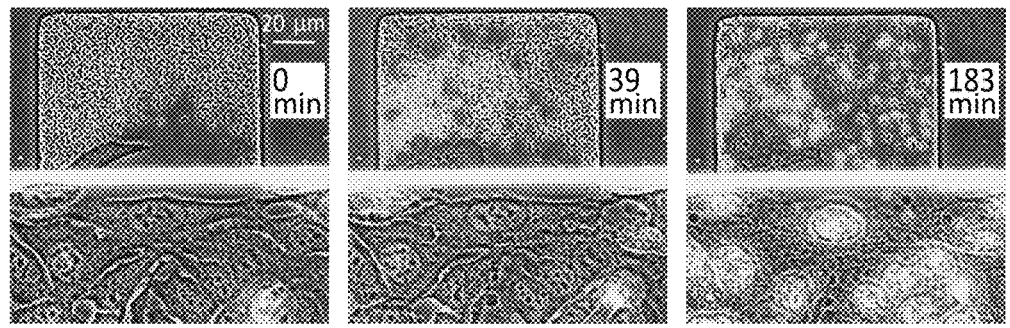
Figure 3C:
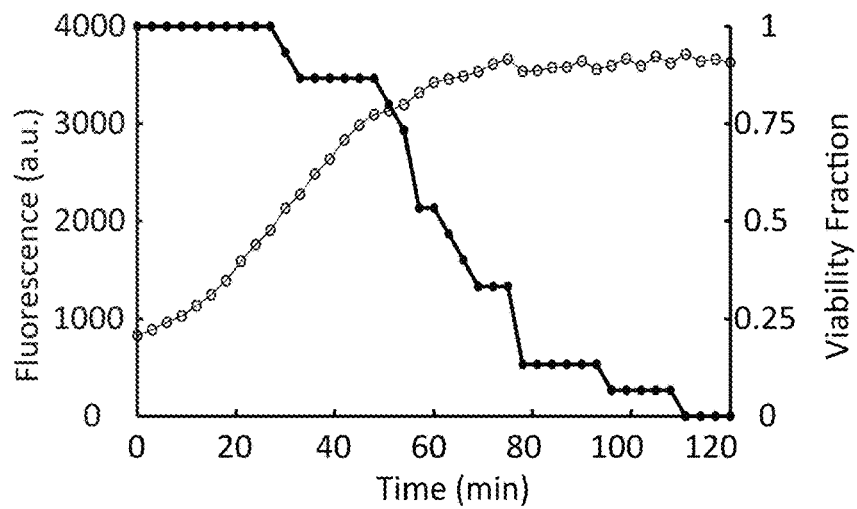
Figure 6A:
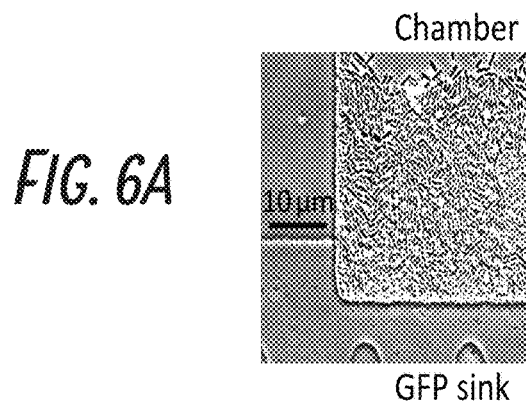
FIG. 6. Investigating lysis mediated intracellular release. (A) A bacterial growth chamber with a 0.4 μm sink for sfGFP visualization after release. (B) Number of bacteria (dashed line and open circles), bacterial fluorescence (solid line and closed circles), sink fluorescence (solid line and open circles) for a typical oscillatory cycle (Strain 1). (C) Fluorescence time series images of the microfluidic sink from (B). (D) General procedure for performing bacterial and cancer cell co-culture experiments in a microfluidic device (also see Supplementary Information) (Kolnik, M., Tsimring, L. S. & Hasty, J. Vacuum-assisted cell loading enables shear-free mammalian microfluidic culture. *Lab On a Chip* 12, 4732-4737 (2012)).
Figure 6B:
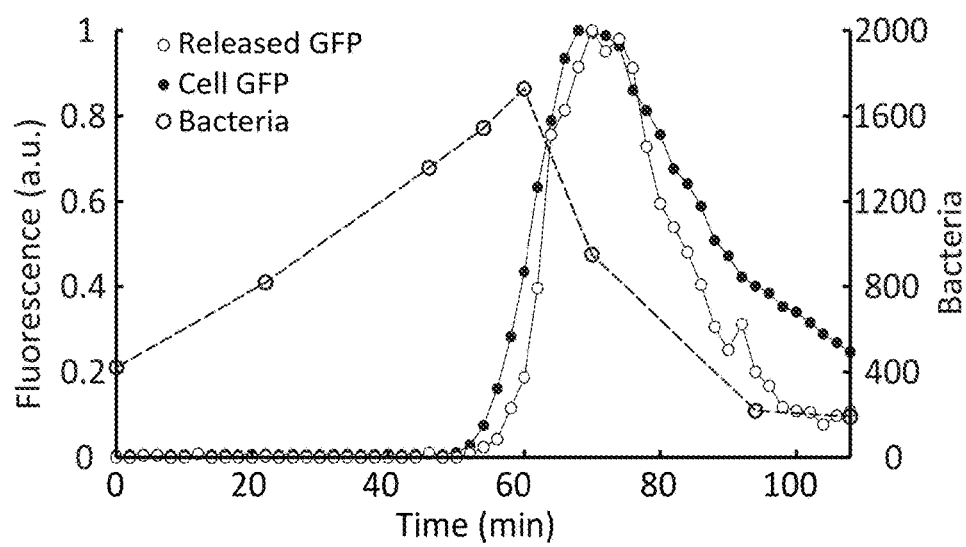
Figure 6C:
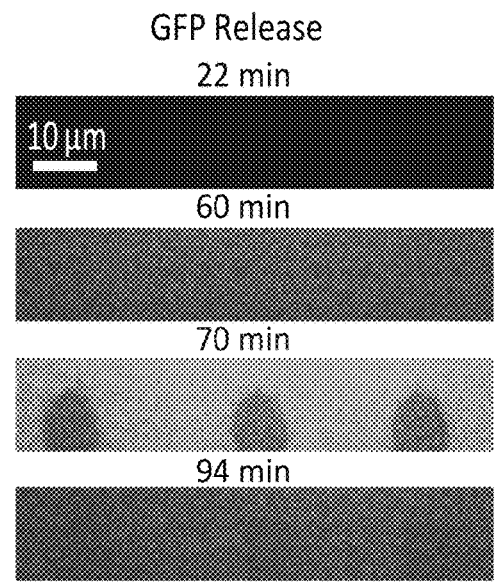
Figure 6D:
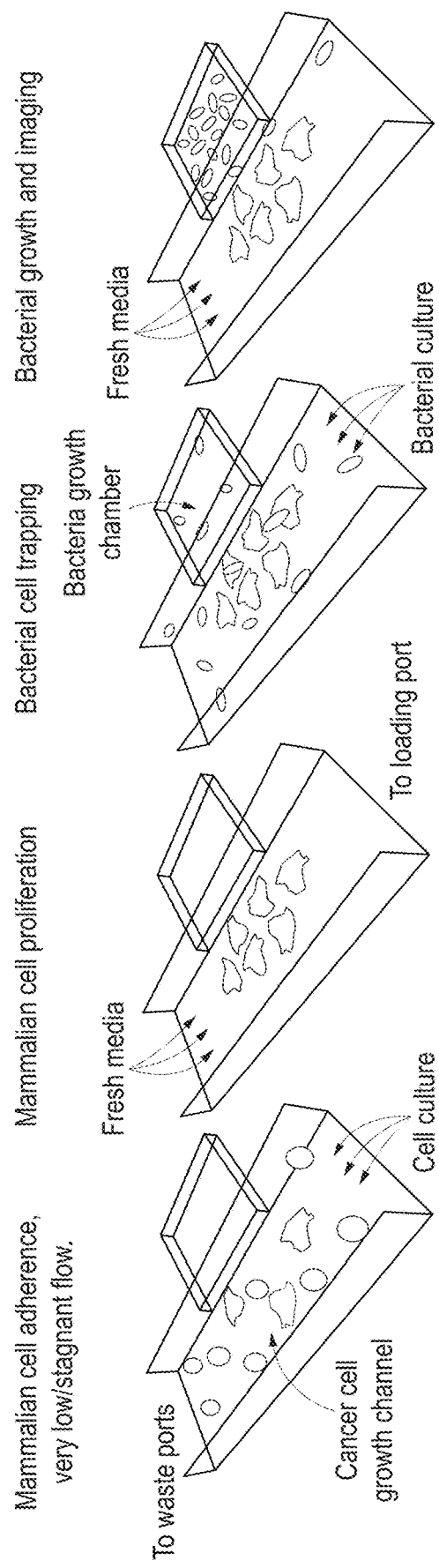

To incorporate therapeutic functionality into the SDC, we added another module to include a copy of Hemolysin E, or hlyE of *E. coli*, which has been used as an anti-tumor therapeutic toxin (Ryan, R. et al. Bacterial delivery of a novel cytolysin to hypoxic areas of solid tumors. *Gene therapy* 16, 329-339 (2009); Nguyen, V. H. et al. Genetically engineered *Salmonella typhimurium* as an imageable therapeutic probe for cancer. *Cancer research* 70, 18-23 (2010)). We confirmed the capability of the circuit to release intracellular contents by visualizing released sfGFP with a small microfluidic sink located beneath the growth chamber (FIG. 6A-C). In order to visualize bacterial lysis and killing of cancer cells in vitro, we employed a novel microfluidic technique whereby cancer cells adhere inside a growth channel flanked by smaller bacterial growth chambers, allowing single-cell visualization of bacterial lysis and cancer cell death (FIG. 6D). Co-culturing HeLa cells with *S. typhimurium* harboring the circuit, we observed HeLa cell death upon the onset of bacterial lysis, indicating efficient toxin release (FIG. 3A-B). The results of these experiments are further summarized in the discussion of Supplementary Videos 5 and 6 provided herein. Complete cell death outside the trap was realized within ~111 min of initial sfGFP fluorescence (FIG. 3C). Thus, the SDC was capable of releasing HlyE at levels necessary to kill cancer cells in vitro.

Figure 3D:
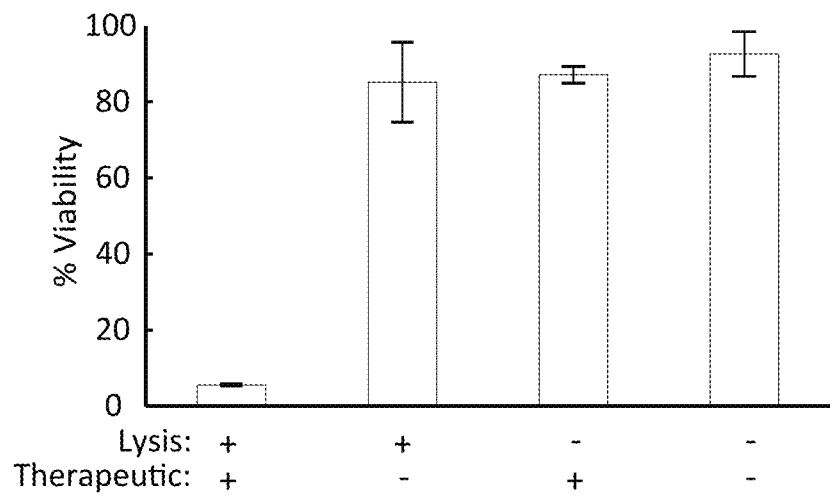
Figure 3E:
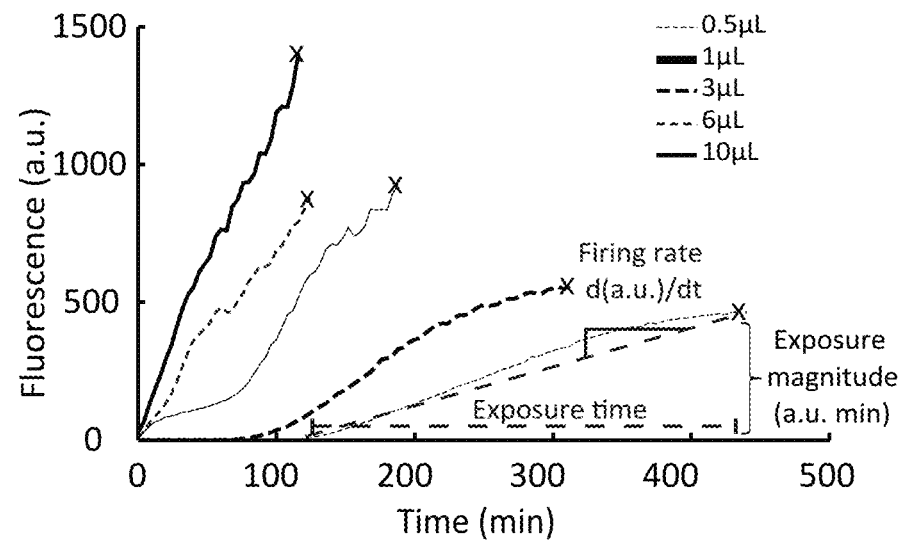
Figure 3F:
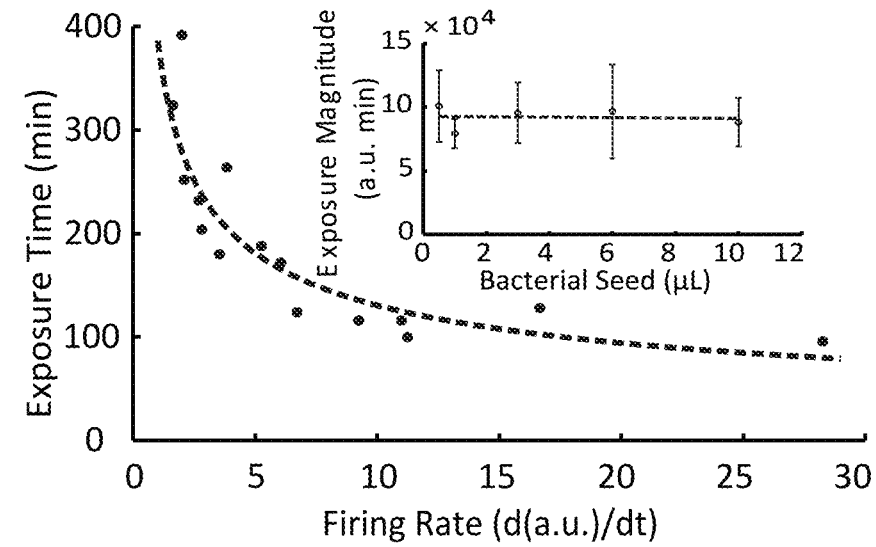

To verify the mechanism of therapeutic activity, we assessed the toxicity of released bacterial contents, as well as basal toxin release from constitutive hlyE expression without lysis. As anticipated, we found that HeLa cells exposed to supernatant from a culture of the SDC with the hlyE module exhibited almost complete loss of viability (FIG. 3D). HeLa cells exposed to supernatant of the SDC without the hlyE module, or a constitutive hlyE strain with no lysis, exhibited a slight loss of ~15% viability. We concluded that lysis allowed for efficient HlyE release in vitro and that natural intracellular bacterial contents do not significantly affect HeLa cell viability. We further investigated the drug delivery characteristics of the SDC with hlyE by seeding variable amounts of circuit-harboring bacteria with HeLa cultures in well plates. We observed that the timing to HeLa cell death from initial seeding increased with lower bacterial seeding volumes, resulting from the extended time needed for bacteria to reach the quorum threshold (FIG. 3E). The results of these experiments were also documented in a video (Supplementary Video 7), which depicts bacteria and cancer cell co-cultured in a tissue culture well-plate at 20× magnification. This video shows that Strain 4 (motile *S. typhimurium*, SDC with HlyE) was loaded in the well with a monolayer HeLa cells. After the bacteria grew, the quorum event was visualized by the expression of green fluorescence protein (GFP). Shortly thereafter, HeLa cells could be seen exhibiting cell death. Timelapse fluorescence microscopy images were taken every 1 min. We also observed that the rate of firing, or the rate of production for the quorum dependent genes such as sfGFP and the lysis gene E, increased with higher seeding densities. This was confirmed by the dependence of the critical release time, or the time from firing to HeLa cell death, on the firing rate. Increased rates corresponded to shorter release times, indicating increased lysis and therapeutic release, although the exposure magnitude needed in all cases appears to be similar (FIG. 3F). In this way, the amount of seeded bacteria determines the initial timing and release characteristics of the circuit.

Figure 4A:
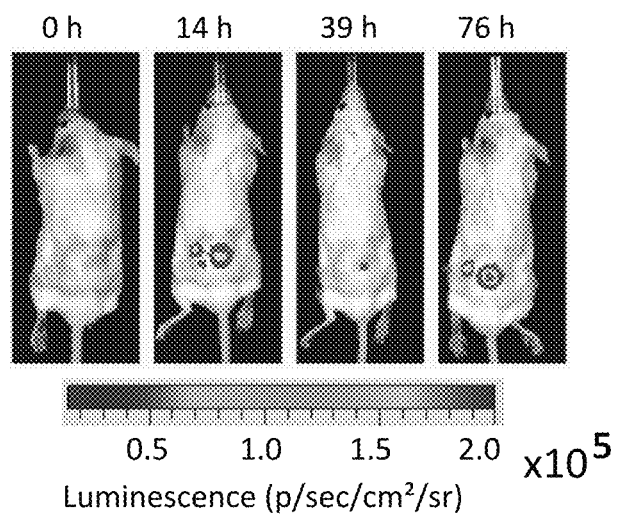
FIG. 4. In vivo therapy and dynamics. (A) IVIS imaging over time of a tumor-bearing mouse with the stabilized therapeutic tSDC strain (Strain 8, quorum therapy and quorum lysis). (B) Relative luminescence profiles from individual tumors following *S. typhimurium* injection with this strain. (C) Relative luminescence profiles from a genomically integrated constitutively luminescent strain (Strain 9). The endpoint luminescence is on average 32-fold higher with the constitutively luminescent strain (right). Experiments in (A)-(C) were performed via intratumoral injection for higher luminescent signal (See also FIG. 7A). (D) Average relative tumor volume over time for tumor-bearing mice injected with the tSDC circuit (solid line, Strain 10) and the no-plasmid control (dashed line, Strain 7). Individual relative tumor volume trajectories are shown (center) where the solid line or dashed line represents the averaged trajectory. The end relative tumor volume for both cases is shown (right). Error bars indicate ±1 standard error for 17 and 22 individual tumors for both the control and tSDC cases, respectively. Each case consisted of >9 mice. *P<0.01, one-way ANOVA. Experiments in (D) were performed via intravenous injection (See also FIG. 7B). (E) Shown are the relative recovery weights from experiments of three strains tested (Bacteria only, Strain 7; the tSDC, Strain 10; a constitutive therapy strain, Strain 12). Error bars indicate ±1 standard error for 5-11 individual mice. **P<0.0001, one-way ANOVA.
Figure 4B:
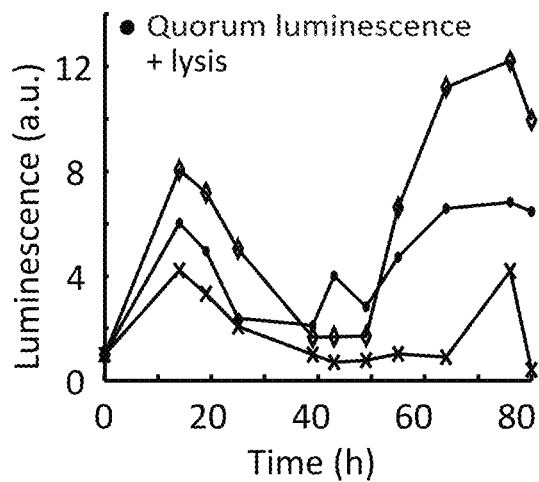
Figure 4C:
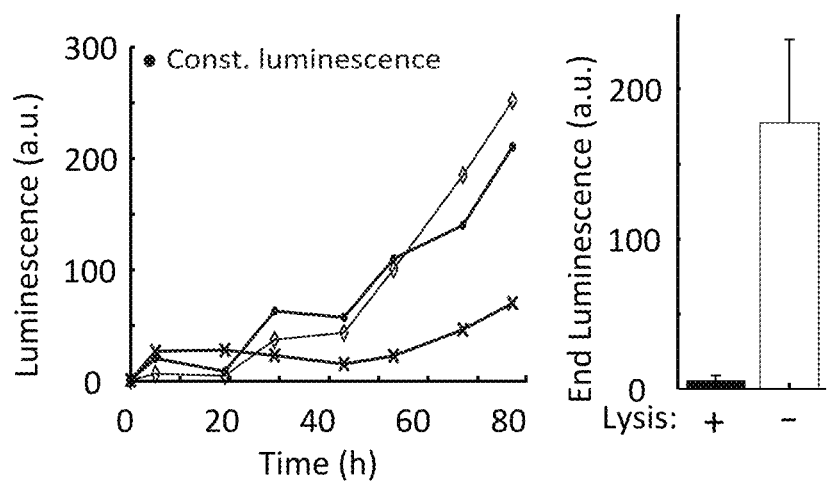
Figures 7A, 7B:
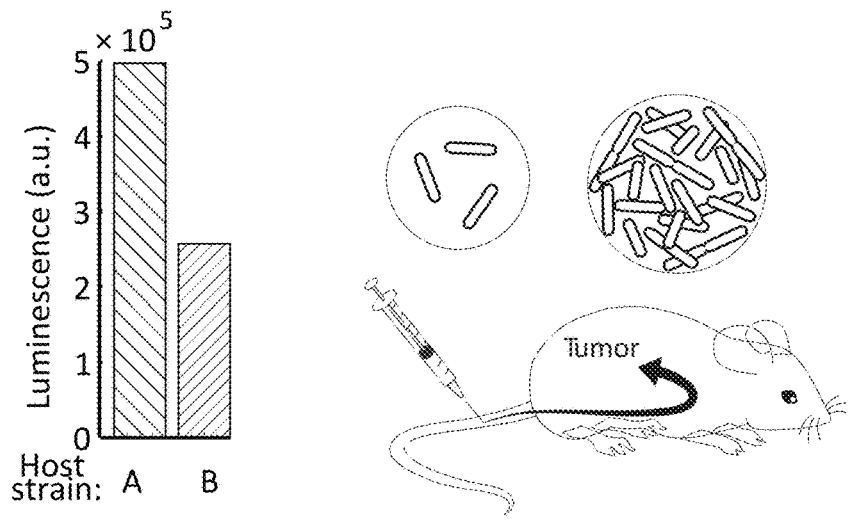
FIG. 7. Investigating therapeutic circuits in vivo. (A) End-point in vitro luminescence intensity for the therapeutic strains used in FIG. 4 after ~20 h of growth. Host strains A and B are Strains 8 and 10. Host A exhibits ~2-fold higher luminescence than Host B. (B) *S. typhimurium* harboring therapeutic circuits are injected via the tail vein and thereafter localize in the tumor. (C) Relative body weight over time for tumor-bearing mice with the tSDC (thick solid line), the constitutive therapy/basal lysis strain (thin dashed line), and bacteria-only control (thick dashed line). Error bars indicate ±1 standard error for 5 and 11 mice for the control and therapy cases, respectively. Experiments were performed intravenously. (D) In vitro growth curves of the various circuits used in vivo (Strains 7, 10, and 12) measured on a plate reader.

With a robust circuit capable of efficient therapeutic delivery, we sought to characterize the dynamics of our system in vivo. The use of bacteria for tumor therapy has been recognized for over a century (Coley, W. B. The treatment of inoperable sarcoma by bacterial toxins (the mixed toxins of the *Streptococcus erysipelas* and the *Bacillus prodigiosus*). *Proceedings of the Royal Society of Medicine* 3, 1 (1910)), and certain facultative anaerobic bacteria, such as *S. typhimurium*, possess the ability to preferentially localize and form colonies within the necrotic regions of the tumor (Forbes, N. S. Engineering the perfect (bacterial) cancer therapy. *Nature Reviews Cancer* 10, 785-794 (2010)). In order to ensure long term stability of the circuit in the absence of antibiotic selection, we integrated stabilizing elements for plasmid retention and segregation (Gerdes, K. The parB (hok/sok) locus of plasmid R1: a general purpose plasmid stabilization system. *Nature Biotechnology* 6, 1402-1405 (1988); Wood, T., Kuhn, R. & Peretti, S. Enhanced plasmid stability through post-segregational killing of plasmid-free cells. *Biotechnology techniques* 4, 39-44 (1990); Derman, A. I. et al. Phylogenetic analysis identifies many uncharacterized actin-like proteins (alps) in bacteria: regulated polymerization, dynamic instability and treadmilling in alp7a. *Molecular microbiology* 73, 534-552 (2009)). Additionally, we placed both hlyE and the luxCDABE genes (the in vivo reporter module) under the luxI promoter as an indicator for hlyE production and quorum firing via bacterial luminescence (FIG. 1A). Using a subcutaneous model of colorectal cancer (MC26 cell line) in immunocompetent mice, we intravenously and intratumorally injected the therapeutic stealth delivery circuit (tSDC) (FIG. 7B). Bacteria localized to the tumor microenvironment as previously observed, and IVIS measurements were regularly obtained (Danino, T., Prindle, A., Hasty, J. & Bhatia, S. Measuring growth and gene expression dynamics of tumor-targeted *S. typhimurium* bacteria. *JoVE* (*Journal of Visualized Experiments*) e50540-e50540 (2013)). We observed the circuit behavior from punctuated 14 and 76 hr peaks in bacterial luminescence localized at the tumor region (FIG. 4A-B). We then tested a control strain that contained an integrated constitutive luminescence cassette and observed a steady increase in bacterial luminescence that did not display punctuated peaks (FIG. 4C). We also observed that the luminescence intensity from the tumor with the tSDC was on average ~32-fold lower than with the constitutive strain, indicating reduction of colony size (FIG. 4C, right). These results show that the tSDC retained dynamic behavior in vivo and was capable of attenuating the bacterial population in the tumor.

Figure 4D:
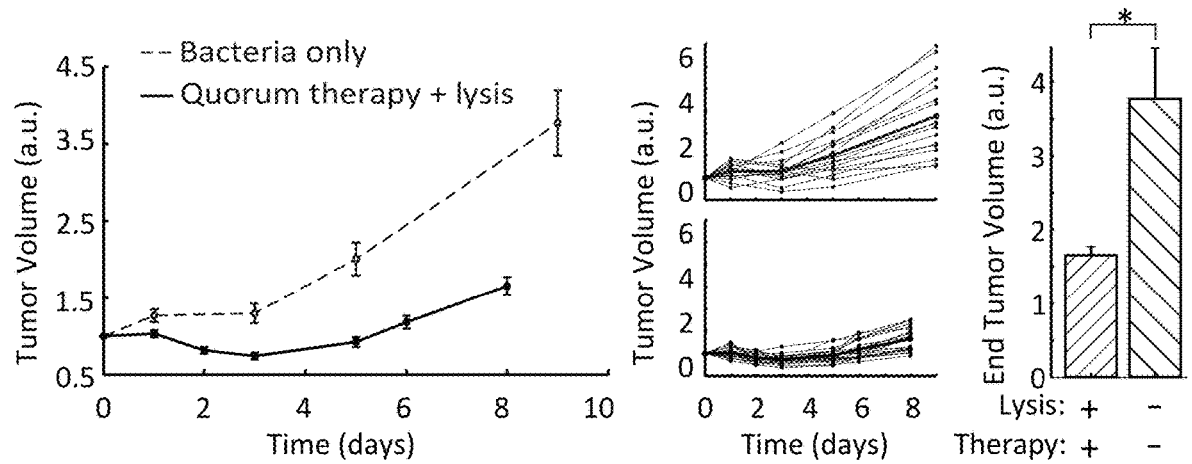
Figure 4E:
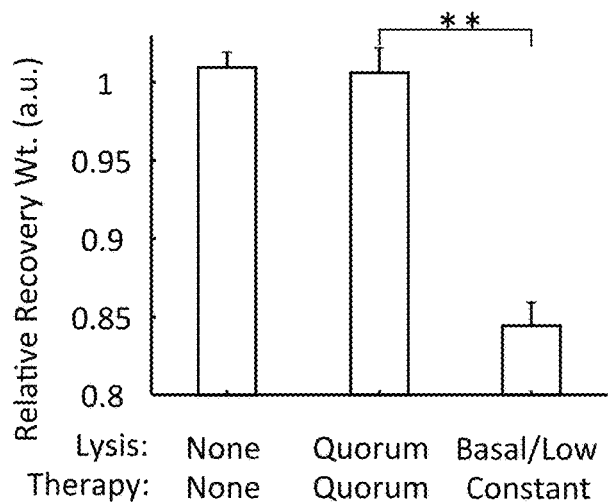
Figure 7C:
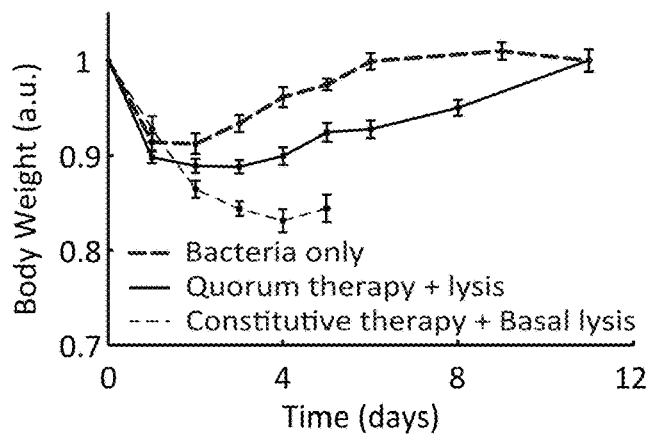
Figure 7D:
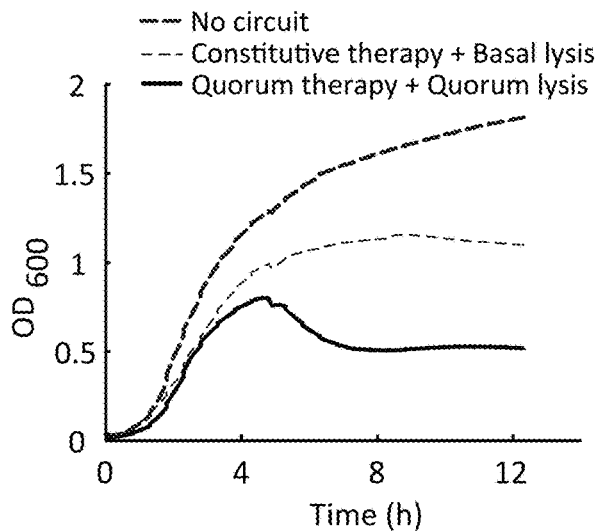
Figure 8A:
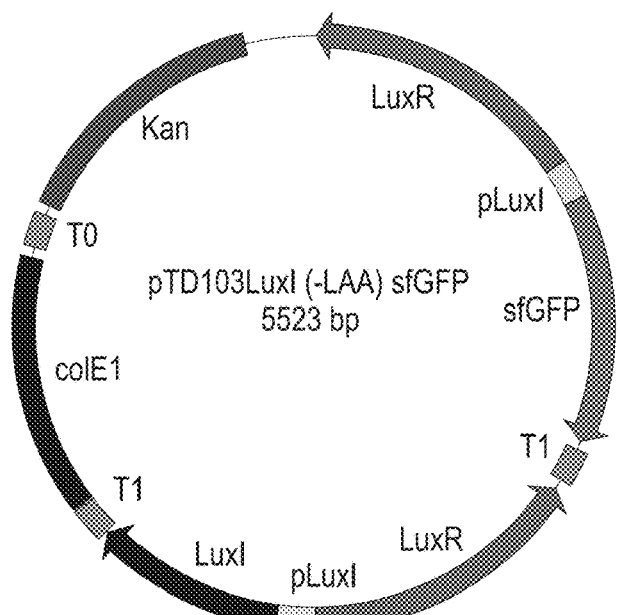
FIG. 8A-I. Graphical representations of some of the plasmids used in this study (see additional information herein).
Figure 8B:
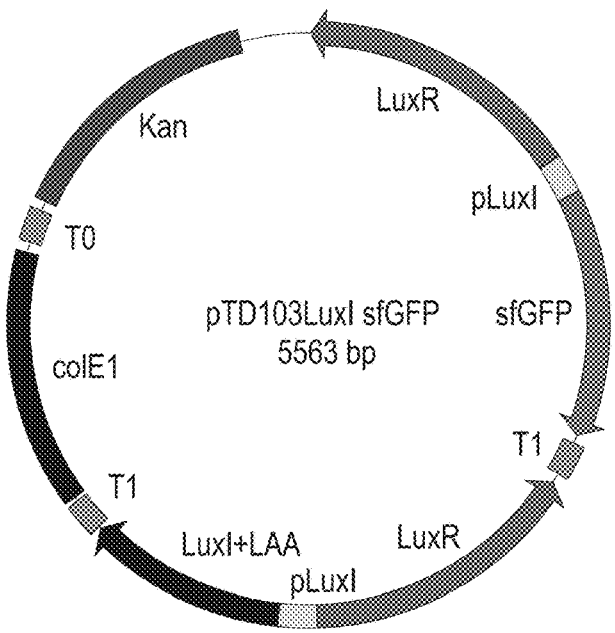
Figure 8C:
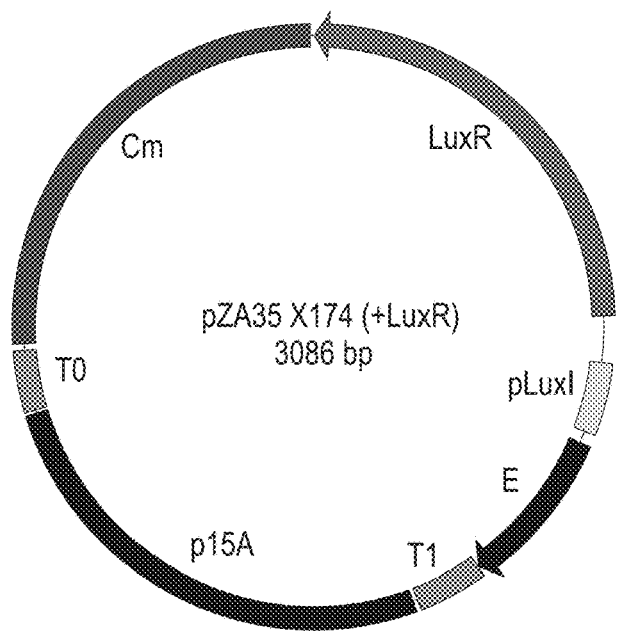
Figure 8D:
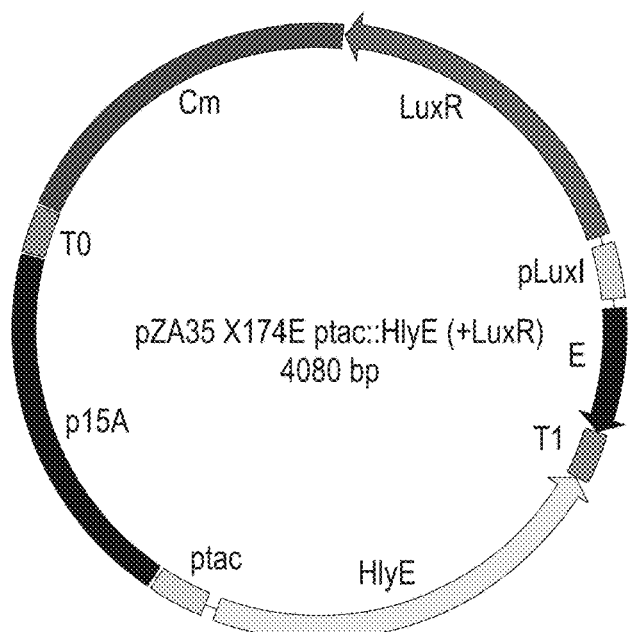
Figure 8E:
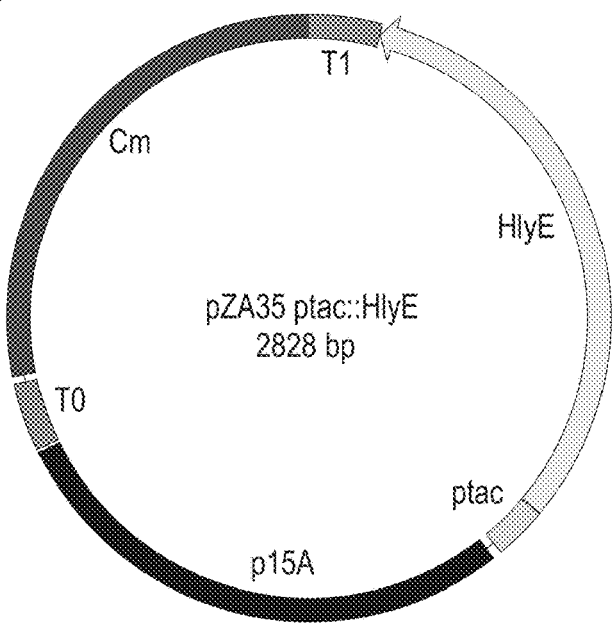
Figure 8F:
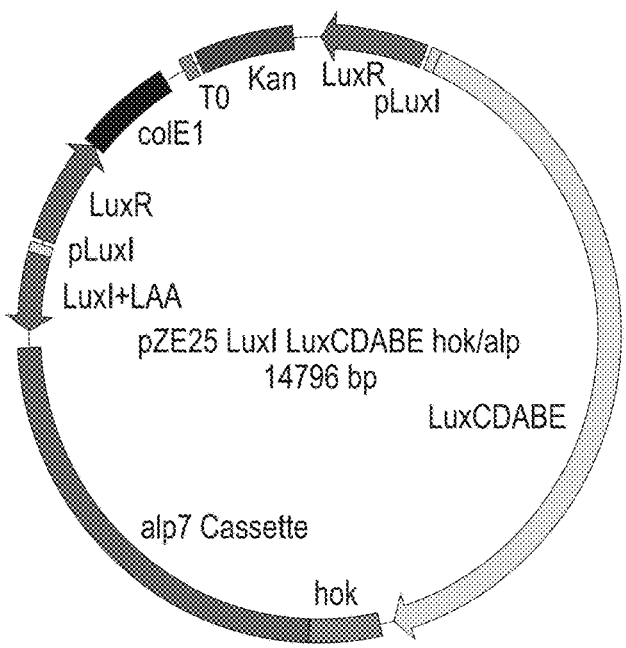
Figure 8G:
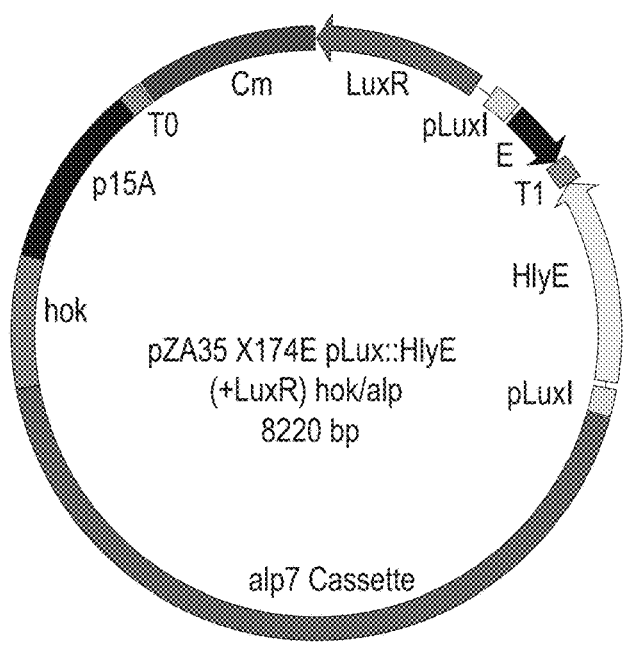
Figure 8H:
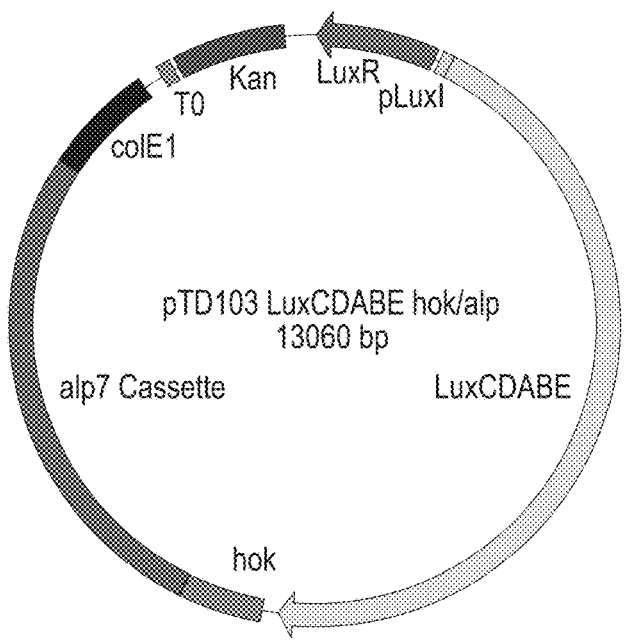
Figure 8I:
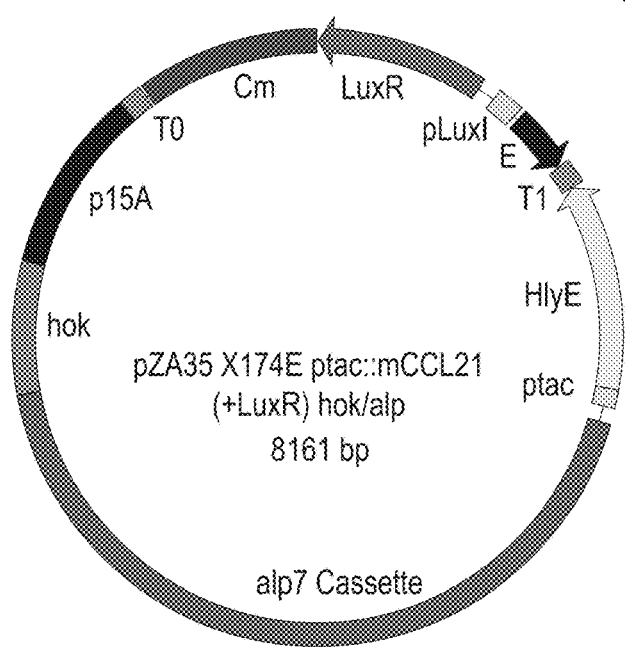
Figure 9A:
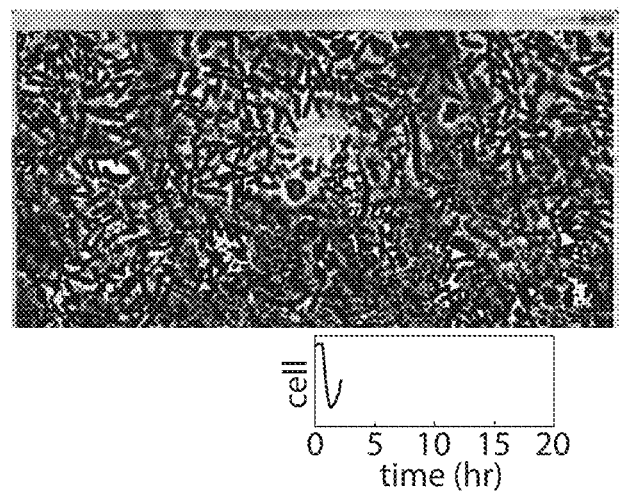
FIGS. 9A-C. Fast and asynchronous intracellular clock oscillations without quorum clock contribution, as the quorum clock requires a critical colony size to function observed using small microfluidic devices (100 cells).
Figure 9B:
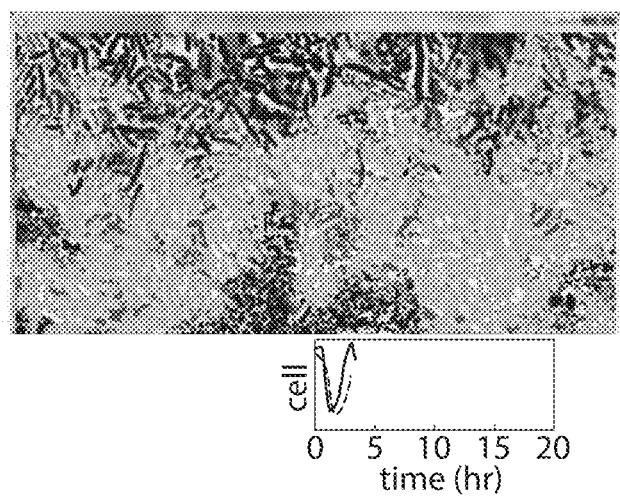
Figure 9C:
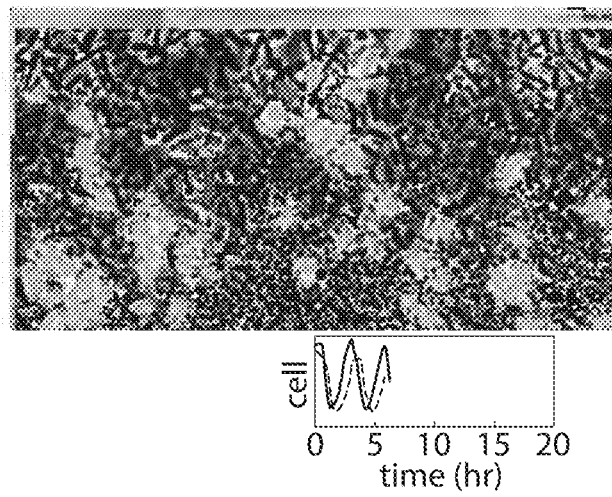

We then investigated the effects of our circuit on tumor volume and mouse body weight. In mice intravenously injected with the tSDC, the tumor volume decreased slightly within the first three days and exhibited stunted growth thereafter (FIG. 4D, left). Tumors treated with no-plasmid bacteria reached over a 3-fold increase in size from Day 1 with an end tumor volume ~2-fold higher than the therapy case (FIG. 4D, right). The tumor volume trajectories for the therapy case also exhibited a reduced variance compared with the control (FIG. 4D, center). After an initial drop in body weight post-injection, both the therapeutic circuit and no-plasmid control mice recovered full body weight within 6-11 days (FIG. 4E and FIG. 7C). We also tested a circuit where the therapeutic was constitutively produced and where the luxI activator for lysis was removed, resulting in basal expression of the lysis gene (FIG. 7D). We observed a significant 16% drop in body weight within the first 5 days with this strain compared to the no-plasmid control and the tSDC (FIG. 4E). Our results indicate that implementing quorum lysis and therapy results in a marked therapeutic effect with a safe health profile in mice.

Advancing applications of engineered cells to the clinic will require robust and dynamic genetic circuits which can execute complex functions in various contexts. Utilizing these types of circuits may enable novel therapeutic strategies by modulating the frequency and amplitude of drug delivery. Future advances may allow for the release of multiple therapeutics, the construction of bacterial sensors allowing for a genetic readout of the local tumor environment, or encoding dynamic and low-dose drug delivery profiles (Lien, K., Georgsdottir, S., Sivanathan, L., Chan, K. & Emmenegger, U. Low-dose metronomic chemotherapy: A systematic literature analysis. *European Journal of Cancer* (2013); Shaked, Y. et al. Low-dose metronomic combined with intermittent bolus-dose cyclophosphamide is an effective long-term chemotherapy treatment strategy. *Cancer research* 65, 7045-7051 (2005); Thakur, M. D. et al. Modelling vemurafenib resistance in melanoma reveals a strategy to forestall drug resistance. *Nature* 494, 251-255 (2013)). Additionally, such engineering strategies may allow for the construction of therapeutic communities in the tumor environment consisting of engineered viruses, bacteria, and host cells (such as T-cells). An environment where multiple members work synergistically can result in the implementation of various therapeutic functions in different regions of the tumor.

Methods

Strains and Plasmids

Our circuit strains were cultured in LB media with 50 µg ml$^{-1}$ and 34 µg ml$^{-1}$ of Kanamycin and Chloramphenicol respectively, along with 0.2% glucose, in a 37° C. incubator. Mammalian cells were cultured in DMEM media supplemented with 10% fetal bovine serum and 1% penicillin/streptomycin (CellGro 30-002-CI), placed inside a tissue culture incubator at 37° C. maintained at 5% $CO_2$. Plasmids were constructed using the CPEC method of cloning or using standard restriction digest/ligation cloning (Quan, J. & Tian, J. Circular polymerase extension cloning of complex gene libraries and pathways. *PloS one* 4, e6441 (2009)). The activator plasmid (Kan, ColE1) was used in previous work from our group, while the lysis plasmid was constructed by taking the lysis gene, E, from the ePop plasmid via PCR and cloning it into a vector (Chlor, p15A) under the control of the LuxI promoter (Prindle, A. et al. A sensing array of radically coupled genetic 'biopixels'. *Nature* 481, 39-44 (2012); Marguet, P., Tanouchi, Y., Spitz, E., Smith, C. & You, L. Oscillations by minimal bacterial suicide circuits reveal hidden facets of host-circuit physiology. *PloS one* 5, e11909 (2010)). The hlyE gene was taken via PCR from the genomic DNA of MG1655 and cloned into the lysis plasmid, under the control of either the ptac or pLuxI promoters (De Boer, H. A., Comstock, L. J. & Vasser, M. The tac promoter: a functional hybrid derived from the trp and lac promoters. *Proceedings of the National Academy of Sciences* 80, 21-25 (1983)). Co-culturing was performed with HeLa cells and either motile or non-motile *S. typhimurium*, SL1344. For full strain and plasmid information, please refer to the Supplementary Information.

Microfluidics and Microscopy

The microfluidic devices and experiment preparation protocols used in this study are similar to those previously reported from our group (Prindle, A. et al. A sensing array of radically coupled genetic 'biopixels'. *Nature* 481, 39-44 (2012)). The bacteria growth chambers were 100×100 µm in area and approximately 1.4 µm in height. For co-culture experiments on the chip, we first loaded a suspended culture of HeLa cells in the device media channels at very low flow rates, to allow for adherence, and then incubated the device in a tissue culture incubator for 0.5-2 days to allow for proliferation (Kolnik, M., Tsimring, L. S. & Hasty, J. Vacuum-assisted cell loading enables shear-free mammalian microfluidic culture. *Lab on a chip* 12, 4732-4737 (2012)). On the day of the experiment, the device was transferred to the microscope and circuit-containing bacteria were loaded in the growth chambers before imaging. Acquisition of images was performed with a Nikon TI2 using a Photometrics CoolSnap cooled CCD camera. The scope and accessories were programmed using the Nikon Elements software. Additional details on microfluidics and microscopy can be found in the Supplementary Information.

In Vivo Experiments

Tumor Models:

Animal experiments were performed on 6 week old female BALB/c mice (Taconic) with bilateral subcutaneous hind flank tumors from an implanted mouse colon cancer cell line (MC26, Tanabe lab, Massachusetts General Hospital). Tumor cells were prepared for implantation at a concentration of 1e8 cell ml$^{-1}$ in DMEM (no phenol red). Cells were then implanted subcutaneously at a volume of 100 µL per flank, with each implant consisting of 1e7 cells. Tumors grew for approximately 2 weeks until reaching 4-10 mm in diameter.

Bacterial Growth and Administration:

Bacterial strains were grown overnight in LB media containing appropriate antibiotics and 0.2% glucose as for the in vitro experiments. A 1/100× dilution in fresh media with antibiotics was started the day of injection and grown until an OD<0.1 to prevent bacteria from reaching the quorum threshold (for SDC specifically). Bacteria were spun down and washed 2-3× with sterile PBS before injection into mice. Bacterial strains were delivered via either intratumoral injections for luminescence trajectory experiments, or intravenous injections for tumor therapy experiments. Intratumoral injections were performed at a concentration of 5e7 cells ml$^{-1}$ in PBS with a total volume of 30-40 µL injected per tumor. Intravenous injections were performed at a concentration of 5e7 cell ml$^{-1}$ in PBS with a total volume of 100 µL injected via the tail vein.

Post-Administration Monitoring:

Luminescent signal was measured with the IVIS Spectrum in vivo imaging system following bacterial injection. Measurements were compared relative to pre-injection values to follow bacterial growth and lysis cycles. Tumor volume was quantified using calipers to measure the length, width, and height of each tumor throughout the imaging course. Volumes were compared to pre-injection values to follow physical tumor growth. Mice were weighed prior to the start of the experiment and typically once daily following the start point to monitor body weight and overall health. Animal experiments were performed in duplicate with similar results.

Host Strains and Culturing

Strains with our lysis circuit were grown in LB media with 50 µg ml$^{-1}$ and 34 µg ml$^{-1}$ of the respective antibiotics (kanamycin and chloramphenicol) along with 0.2% glucose in a 37° C. shaking incubator. The glucose was added in order to decrease expression from the luxR promoter, as this promoter has a binding site for the CAP-cAMP activating complex (Meighen, E. A. Genetics of bacterial bioluminescence. *Annual review of genetics* 28, 117-139 (1994)). When glucose levels in the cell are high, levels of cAMP are low, decreasing the transcriptional activation from CAP-cAMP.

For the microfluidics experiments we selected a non-motile *S. typhimurium* host for our circuit, SL1344 (M913: fliGHI mutant) (Stecher, B. et al. Flagella and chemotaxis are required for efficient induction of *Salmonella enterica* serovar *typhimurium* colitis in streptomycin-pretreated mice. *Infection and Immunity* 72, 4138-4150 (2004)). For well-plate co-culture experiments and in vivo experiments for therapy and body weight, we utilized an attenuated *S. typhimurium* host, SL1344 (ELH1301: ΔphoPQ ΔaroA), that was shown in previous work to have good efficiency in plasmid retention (Danino, T., Lo, J., Prindle, A., Hasty, J. & Bhatia, S. N. In vivo gene expression dynamics of tumor-targeted bacteria. *ACS Synthetic Biology* 1, 465-470 (2012)). For in vivo experiments where the luminescence expression of the circuit was measured, we utilized another attenuated strain of *S. typhimurium* SL1344 as the circuit host (ELH430: ΔphoPQ) where luminescence expression was higher (see FIG. 7A and FIG. 23A). For the constitutive luminescence case we used a well characterized bacterium with a constitutive luminescence cassette, *E. coli* Nissle 1917 integrated with p16Slux (Riedel, C. U. et al. Construction of p16slux, a novel vector for improved bioluminescent labeling of gram-negative bacteria. *Applied and Environmental Microbiology* 73, 7092-7095 (2007)). A list of strains and plasmids are shown in Tables 1 and 2 below.

inside a tissue culture incubator at 37° C. with 5% $CO_2$ before the experiment. For loading on a microfluidic chip or well-plate, HeLa cells were initially washed with dPBS and dis-adhered with 0.05% or 0.25% trypsin EDTA. Cells were then pelleted and resuspended in DMEM+FBS and the appropriate antibiotics.

Plasmids

Our circuit is composed of two plasmids, an activator plasmid and a lysis/therapeutic plasmid. The main activator plasmid is pTD103LuxI sfGFP which was used in previous work from our group (Prindle, A. et al. A sensing array of

TABLE 1

| Strain # | Strain Name | Host Bacterium | Plasmid(s) |
|---|---|---|---|
| 1 | MOD47 | SL1344, M913 | pTD103 luxI (−LAA) sfGFP + pZA35 X714E (+LuxR) |
| 2 | MOD46a | SL1344, M913 | pTD103 luxI sfGFP + pZA35 X714E (+LuxR) |
| 3 | MOD67 | SL1344, M913 | pTD103 luxI (−LAA) sfGFP + pZA35 X714E (+LuxR) ptac::HlyE |
| 4 | MOD61 | SL1344, ELH1301 | pTD103 luxI sfGFP + pZA35 X714E (+LuxR) ptac::HlyE |
| 5 | MOD64 | SL1344, ELH1301 | pTD103 luxI sfGFP + pZA35 X714E (+LuxR) |
| 6 | MOD65 | SL1344, ELH1301 | pZA35 ptac::HlyE |
| 7 | ELH1301 | SL1344, ELH1301 | N/A |
| 8 | MOD105 | SL1344, ELH430 | pZE25 luxI luxCDABE hok/alp + pZA35 X714E (+LuxR) pLux::HlyE hok/alp |
| 9 | EcN-luxCDABE | Nissle 1917 | N/A |
| 10 | MOD101 | SL1344, ELH1301 | pZE25 luxI luxCDABE hok/alp + pZA35 X714E (+LuxR) pLux::HlyE hok/alp |
| 11 | MOD102 | SL1344, ELH1301 | pZE25 luxI luxCDABE hok/alp + pZA35 X714E (+LuxR) ptac::HlyE hok/alp |
| 12 | MOD69 | SL1344, ELH1301 | pTD103 LuxCDABE hok/alp + pZA35 X714E (+LuxR) ptac::HlyE hok/alp |
| 13 | MOD29 | JS006, BW25113 | pTD103 luxI sfGFP + pZA35 X714E (+LuxR) |
| 14 | MOD41 | JS006, BW25113 | pTD103 luxI (−LAA) sfGFP + pZA35 X714E (+LuxR) |
| 15 | MOD42 | JS006, BW25113 | pTD103 luxI (TS) sfGFP + pZA35 X714E (+LuxR) |

TABLE 2

| Strain # | Strain Name | Host Bacterium | Plasmid(s) |
|---|---|---|---|
| 1 | MOD47 | SL1344, M913 | pTD103 luxI (−LAA) sfGFP + pZA35 X714E (+LuxR) |
| 2 | MOD46a | SL1344, M913 | pTD103 luxI sfGFP + pZA35 X714E (+LuxR) |
| 3 | MOD67 | SL1344, M913 | pTD103 luxI (−LAA) sfGFP + pZA35 X714E (+LuxR) ptac::HlyE |
| 4 | MOD61 | SL1344, ELH1301 | pTD103 luxI sfGFP + pZA35 X714E (+LuxR) ptac::HlyE |
| 5 | MOD64 | SL1344, ELH1301 | pTD103 luxI sfGFP + pZA35 X714E (+LuxR) |
| 6 | MOD65 | SL1344, ELH1301 | pZA35 ptac::HlyE |
| 7 | ELH1301 | SL1344, ELH1301 | N/A |
| 8 | MOD105 | SL1344, ELH430 | pZE25 luxI luxCDABE hok/alp + pZA35 X714E (+LuxR) pLux::HlyE hok/alp |
| 9 | EcN-luxCDABE | Nissle 1917 | N/A |
| 10 | MOD101 | SL1344, ELH1301 | pZE25 luxI luxCDABE hok/alp + pZA35 X714E (+LuxR) pLux::HlyE hok/alp |
| 11 | MOD102 | SL1344, ELH1301 | pZE25 luxI luxCDABE hok/alp + pZA35 X714E (+LuxR) ptac::HlyE hok/alp |
| 12 | MOD69 | SL1344, ELH1301 | pTD103 LuxCDABE hok/alp + pZA35 X714E (+LuxR) ptac::HlyE hok/alp |
| 13 | MOD29 | JS006, BW25113 | pTD103 luxI sfGFP + pZA35 X714E (+LuxR) |
| 14 | MOD110 | SL1344, ELH1301 | pZE25 luxI luxCDABE hok/alp + pZA35 X714E (+LuxR) pLux::CDD-IRGD hok/alp |
| 15 | MOD112 | SL1344, ELH1301 | pZE25 luxI luxCDABE hok/alp + pZA35 X714E (+LuxR) ptac::mCCL21 hok/alp |

For co-culture experiments, we used the HeLa cell line in DMEM (complete medium) supplemented with 10% fetal bovine serum and appropriate antibiotics for the circuit. HeLa cells were initially grown with penicillin/streptomycin (CellGro 30-002-CI) in the growth medium and placed radically coupled genetic 'biopixels'. *Nature* 481, 39-44 (2012)). This plasmid contains the ssrA-LAA degradation tag (amino-acid sequence of AANDENYALAA) on LuxI and sfGFP, a superfolding green fluorescent protein variant (Pédelacq, J.-D., Cabantous, S., Tran, T., Terwilliger, T. C. &

Waldo, G. S. Engineering and characterization of a superfolder green fluorescent protein. *Nature Biotechnology* 24, 79-88 (2005)). pTD103LuxI (-LAA) and pTD103LuxI (TS) was constructed by removing the ssrA-LAA tag from LuxI. Most of the construction was done using the CPEC method of cloning (Quan, J. & Tian, J. Circular polymerase extension cloning of complex gene libraries and pathways. PloS One 4, e6441 (2009)).

The lysis plasmids were constructed using the modular pZ plasmid set-up with a p15a origin of replication and a chloramphenicol resistance marker (Lutz, R. & Bujard, H. Independent and tight regulation of transcriptional units in *Escherichia coli* via the lacr/o, the tetr/o and arac/i1-i2 regulatory elements. Nucleic acids research 25, 1203-1210 (1997)). The lysis gene, E from the bacteriophage φX174, was kindly provided by Lingchong You and was taken from the previously reported ePop plasmid via PCR (Marguet, P., Tanouchi, Y., Spitz, E., Smith, C. & You, L. Oscillations by minimal bacterial suicide circuits reveal hidden facets of host-circuit physiology. PloS One 5, e11909 (2010)). The E gene was placed under the expression of the LuxR-AHL activatable luxI promoter. In order to construct the therapeutic versions of the lysis plasmids, we extracted the hlyE gene from the genomic DNA of *E. coli* strain MG1655 via PCR and inserted it into the lysis plasmid. The promoter used to drive expression of the toxin was the tac promoter for in vitro characterization, and the luxI promoter for in vivo testing. Along with a transcriptional terminator at the end of the gene, this formed the therapeutic toxin cassette. The CDD-iRGD and mCCL21 genes were synthesized as fragments before inserting into the appropriate plasmids.

For the plasmids used in the circuit strains tested in vivo, we inserted two stabilizing elements, the hok/sok system and alp7 partitioning system, into the activator and lysis/therapeutic plasmids. Recent work has shown that addition of the hok/sok toxin-antitoxin system and the alp7AR cassette from the *B. subtilis* plasmid pLS20 enables almost complete plasmid retention in vivo (Gerdes, K. The parB (hok/sok) locus of plasmid R1: a general purpose plasmid stabilization system. *Nature Biotechnology* 6, 1402-1405 (1988); Wood, T., Kuhn, R. & Peretti, S. Enhanced plasmid stability through post-segregational killing of plasmid-free cells. *Biotechnology Techniques* 4, 39-44 (1990)).

See FIG. 8 and FIG. 25 for maps of the plasmids used in this study.

Microscopy and Microfluidics

The microscopy and microfluidics techniques described here are similar to those reported previously from our group (Danino, T., Mondragón-Palomino, O., Tsimring, L. & Hasty, J. A synchronized quorum of genetic clocks. *Nature* 463, 326-330 (2010)). Briefly, our microfluidic devices were constructed from PDMS (polydimethylsiloxane) which was molded and baked on a silicon wafer with micron-scale features formed by cross-linked photoresist. Individual devices (formed by a set of features transferred from the wafer to the PDMS) were then cut out of the baked PDMS and holes were punctured in the devices to allow for the connection of fluid lines. The devices were then bonded onto coverslips and placed on a microscope stage for cell loading and imaging. Fluid lines were connected to the devices from various syringes supplying media, cells, or acting as waste reservoirs. The flow direction in the device was controlled by changing the relative heights between the relevant syringes resulting in hydrostatic pressure driven flow.

Figure 22A:
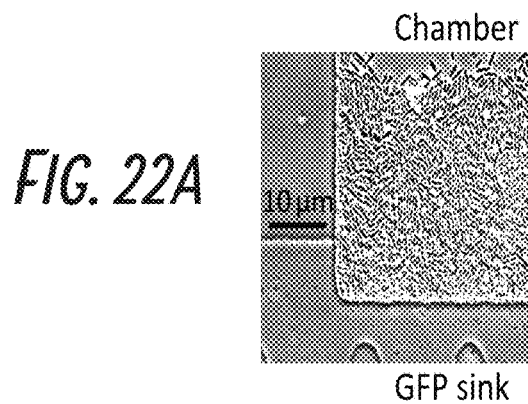
FIG. 22. Investigating lysis mediated intracellular release. (A) A bacterial growth chamber with a 0.4µ m sink for sfGFP visualization after release. (B) Number of bacteria (dashed line, open circles), bacterial fluorescence (solid line, closed circles), sink fluorescence (solid line, open circles) for a typical oscillatory cycle (Strain 1). (C) Fluorescence time series images of the microfluidic sink from (B). (D) General procedure for performing bacterial and cancer cell co-culture experiments in a microfluidic device (also see Supplementary Information) (Kolnik, M., Tsimring, L. S. & Hasty, J. Vacuum-assisted cell loading enables shear-free mammalian microfluidic culture. *Lab On a Chip* 12, 4732-4737, 2012).
Figure 22B:
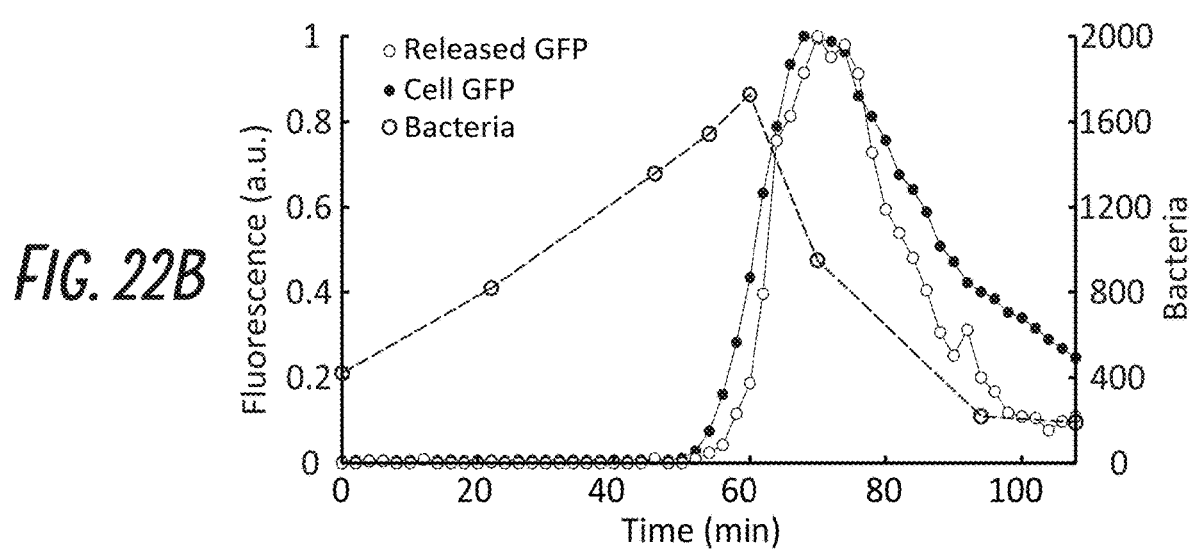
Figure 22C:
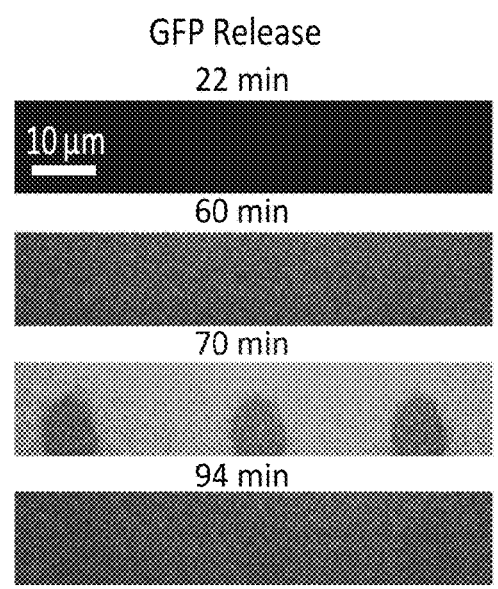

We cultured cells to an optical density ($A600_{nm}$) of approximately 0.1 (using 1.5 ml cuvettes from Plastibrand) before loading a device. Before loading, devices were 'wetted' with the media syringes to remove bubbles in the channels (Ferry, M., Razinkov, I. & Hasty, J. Microfluidics for synthetic biology from design to execution. *Methods Enzymol* 497, 295 (2011)). Devices were loaded from the cell port by lowering the designated waste port such that the relative changes in height of the cell loading syringe and waste syringe resulted in flow of cells from the cell port to a waste port. Once cells were loaded in the traps, the flow direction was reversed allowing media to flow into all ports, thus supplying the trapped cells with a continuous perfusion of nutrients. In these microfluidic experiments we added 0.075% Tween20 to the media and cell suspension fluid to prevent cells from adhering to channels and ports within the device. Experiments for characterizing circuit behavior in FIG. 1-2 were done in a side-trap array device, as described previously (Danino, T., Mondragón-Palomino, O., Tsimring, L. & Hasty, J. A synchronized quorum of genetic clocks. *Nature* 463, 326-330 (2010)). The device used with the GFP sink is also arranged as a side-trap array. See FIG. 6A and FIG. 22A for a schematic of the trap and sink.

For the co-culture experiments on the chip, we utilized the side-trap array device and added fluidic resistance on all of the inlet/outlet ports with sinuous channels to increase the dynamic range of achievable flow rates. For mammalian cell loading, cells were trypsinized, pelleted, and resuspended in 0.5-1.0 mL DMEM+FBS+antibiotics (Kanamycin and Chloramphenicol) before loading. Cells were loaded under a light microscope such that un-adhered cells were localized in the media channels under near-stagnant flow conditions. The microfluidic chip and syringe apparatus was then carefully placed in the $CO_2$ incubator while avoiding any changes in the relative heights of the syringes to maintain near-stagnant flow. The cells were allowed to adhere within 2-4 hours before slightly raising the media syringe to supply fresh media to the channels, and then left to proliferate overnight. On the next day, the chip and syringe apparatus was transferred to the microscope under a temperature and $CO_2$ environmental chamber as described previously (Kolnik, M., Tsimring, L. S. & Hasty, J. Vacuum-assisted cell loading enables shear-free mammalian microfluidic culture. *Lab On a Chip* 12, 4732-4737, 2012). The bacterial culture was then prepared and loaded as described above before imaging. If flow rate was too high, it was lowered when the bacterial population reached the quorum threshold (indicated by the appearance of sfGFP) to allow for better diffusion of the released therapeutic into the mammalian growth channel. For a schematic of the main steps involved, refer to FIG. 6D and FIG. 22D.

For microscopy we used the same system as described in our previous work (Prindle, A. et al. A sensing array of radically coupled genetic 'biopixels'. *Nature* 481, 39-44, 2012). Briefly, we used a Nikon Eclipse TI epifluorescent microscope with phase-contrast based imaging. For the acquisition of images, we used a CoolSNAP HQ2 CCD camera from Photometrics. The microscope and acquisition was controlled by the Nikon Elements software. A plexiglass incubation chamber connected to a heating unit, which encompassed a wide area around the stage, was used in order to maintain the temperature of the microfluidic device. Phase-contrast images were taken at 60× magnification at 50-200 ms exposure times. Fluorescent imaging at 60× was performed at 150 ms for GFP, 30% setting on the Lumencor SOLA light source. Images were taken every 2-3 minutes for the course of a typical experiment. In order to estimate the flow rate in the device channel, we measured the length of traces of fluorescent beads (1.0 µm) upon 200 ms exposure of fluorescent light to estimate the average fluid velocity.

Further information on the analysis of these images is presented in the Data Analysis section below.

Well-Plate Experiments

For the viability experiments, we seeded a monolayer of HeLa cells on standard tissue culture 96-well flat bottom plates (Fisher Scientific) with penicillin and streptomycin antibiotics. We grew the four bacterial strains from FIG. 3D in 50 mL cultures to an optical density of 0.08 before pelleting and re-suspending in 1.2 mL media with the appropriate antibiotics. The bacterial cultures were then grown for one hour and then pelleted in a 1.5 mL microcentrifuge tube. 100 µL of each resulting supernatant was then added to three HeLa culture wells. Thereafter we implemented the protocol for the Vybrant MTT Cell Proliferation Assay Kit (V-13154, Molecular Probes) to measure HeLa cell viability.

For the variable seeding experiments (FIG. 3E-F), we also utilized the same well-plates. We grew the SDC+HlyE strain to an optical density of ~0.07 before pelleting the cells and re-suspending in 1 mL of fresh media and antibiotics. Variable volumes of this dense culture were then seeded to three wells for each respective case, and imaging was performed at 20× magnification.

Data Analysis

Fluorescence intensity profiles were obtained by analyzing frames from the fluorescent channel and plotting the mean pixel intensity over time. The period measured is the peak-to-peak period of the fluorescence profile. The number of cells in the trap was found by analyzing the phase-contrast images in ImageJ. Since bacteria formed a monolayer in the growth chamber, we first estimated the average area of an individual bacterial cell and the average void fraction (open space between bacteria in the trap). Taking into account the µm/pixels of the image, we measured the area of the trap taken up by cells using ImageJ and divided by the average area of a bacterial cell. This value was then multiplied by (1-void fraction) to yield the total estimated number of cells in the trap. Bacteria that were not close to the main group of cells were counted individually and added to the final number. The fraction of cells lysed per period was found by dividing the number of lysed bacteria by the maximum number of bacteria before lysis. Plots were generated by using MATLAB.

In order to estimate the flow rate in the media channel, we imaged fluorescent 1 µm beads at 20× and analyzed the images using MATLAB. The length of the fluorescent bead traces was measured in pixels and converted to microns. The length of the trace was then divided by the exposure time (200 ms) to yield the flow velocity. In this study we report the median flow velocity because it is less sensitive to outliers in the bead traces.

Modeling

To describe the dynamic behavior of the SDC we developed an ordinary differential equation model with equations for cell population size (N), AHL (H), inter-cellular LuxI (I), and inter-cellular lysis protein E (L). The population variables are cell population number (N) and extracellular AHL (H) (we assume LuxR-AHL binding is fast). This model can be thought of as a system where we follow a surviving lineage (via a single cell) throughout the experiment which responds to extracellular AHL, which in turn increases with cell number. Once the extracellular AHL threshold is reached, the intracellular production of the Lux driven genes, LuxI and E, are brought to the ON state (second stable state), due to the positive feedback provided by the activation term Plux. Increase in the lysis protein leads to a rapid reduction of cell number via the killing term, γN, modeled as a hill function to switch killing ON/OFF based on the concentration of lysis protein. Once AHL and lysis protein levels decay, Plux and γN turn back to their OFF stable states, allowing cell number to rise and repeat the process. Since firing is dependent on a threshold value of AHL, the SLC can be thought of as a circuit displaying integrate-and-fire behavior.

Maximum cell population ($N_0$) is defined by the maximum number of cells that could fit inside a single cell trap. Cells leave the trap as the consequence of cell growth ($\mu_G$). The rate of cell degradation through lysis is described by hill function $\gamma_N$. We assumed AHL diffusion through the cell membrane to be fast, allowing for dynamic description of total AHL (H) in the trap. Production of AHL (H) is proportional to the product of cell population (N) and per cell concentration of LuxI (I). AHL dilution is inversely proportional to N due to the increased blockage of AHL clearance from the trap as the result of cell accumulation. Internal production of LuxI and lysis proteins is described by $P_{lux}$. Degradation of both proteins is due to cell growth ($\mu_G$) as well as some basal degradation ($\gamma_I$ and $\gamma_L$). In addition, LuxI is further degraded by ClpXP machinery ($\gamma_C$).

$$\frac{dN}{dt} = \mu_G N(N_0 - N) - \gamma_N N \quad (1)$$

$$\frac{dH}{dt} = bNI - \frac{\mu H}{1 + N/N_0} \quad (2)$$

$$\frac{dL}{dt} = C_L P_{lux} - \gamma_L L - \mu_G L \quad (3)$$

$$\frac{dI}{dt} = C_I P_{lux} - \gamma_I I - \mu_G I - \mu_C I \quad (4)$$

$$P_{lux} = \alpha_0 + \frac{\alpha_H (H/H_0)^4}{1 + (H/H_0)^4}$$

$$\gamma_N = \frac{kL^n}{L_0^n + L^n}$$

Figure 5E:
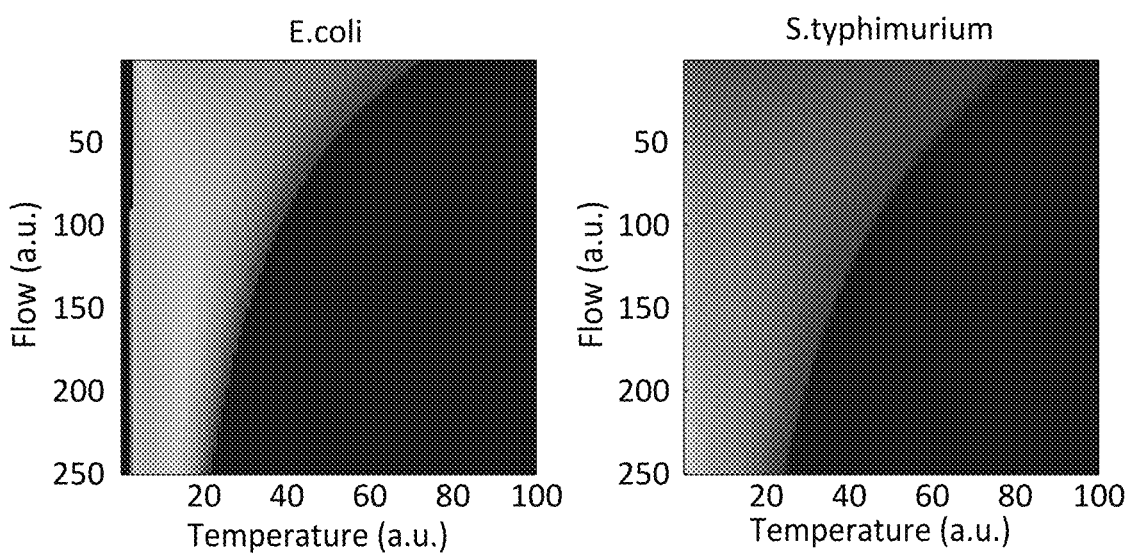

Parameters:

We chose model parameters to qualitatively fit the experimental population and GFP (proxy for LuxI) trajectories (FIG. 2A). Increased protein production and degradation in *S. typhimurium* as compared to *E. coli* was reported in previous work (Prindle, A. et al. Genetic circuits in *Salmonella typhimurium*. ACS Synthetic Biology 1, 458-464 (2012)). We find that the three parameters (AHL, LuxI production rates and basal LuxI degradation rate: $C_L$, $C_I$, $\gamma_L$, $\gamma_I$) account for the major qualitative differences in behavior between *E. coli* and *S. typhimurium* (FIG. 2B). We scanned all three parameters to find that increase in all three expands the region of circuit oscillations (FIG. 5E).

Model Parameter Values:

In some experiments described herein, the following model parameter values were used: $\mu_G$ (Dilution due to cell growth) 0.2; $N_0$ (Maximum cell population size) 10; k (Maximum rate of cell lysis) 10; $L_0$ (Conc. of lysis gene resulting in half maximum lysis) 2; n (Hill coefficient of lysis function) 4; b (AHL production rate) 50; µ(Maximum AHL clearance rate due to flow) 15; $C_L$, (Lysis gene copy number) 0.5; $C_I$ (LuxI copy number) 1; $\alpha_0$ (Lux promoter basal production) 0.5; $\alpha_H$ (Lux promoter AHL induced production) 30; $H_0$ (AHL binding affinity to Lux promoter) 5; $\gamma_L$ (Basal degradation of lysis protein) 2; $\gamma_I$ (Basal degradation of LuxI) 2; $\gamma_C$ (ClpXP degradation of LuxI) 8.

In some experiments, the following model parameter values were used: µG (Dilution due to cell growth) 0.2; NO (Maximum cell population size) 10; k (Maximum rate of cell lysis) 10; L0 (Conc. of lysis gene resulting in half maximum lysis) 2; n (Hill coefficient of lysis function) 2; b (AHL production rate) 25; μ (Maximum AHL clearance rate due to flow) 12; CL (Lysis gene copy number) 0.5; CI (LuxI copy number) 1; α0 (Lux promoter basal production) 0.5; αH (Lux promoter AHL induced production) 35; H0 (AHL binding affinity to Lux promoter) 5; γL (Basal degradation of lysis protein) 2; γI (Basal degradation of LuxI) 2; γC (ClpXP degradation of LuxI) 12.

Supplementary Videos

Supplementary Video 1.

A video showing timelapse fluorescence microscopy of the Stealth Delivery Circuit (SDC) in Strain 1 (*S. typhimurium*, no ssrA tag on LuxI) at 60× magnification was taken. This video shows that bacterial colony grew in a microfluidic chamber until it reached a quorum threshold at which the cells fluoresced (indicating the quorum activation of the circuit genes) and a fraction of the population lysed. The survivors re-populated and grew until the threshold was reached again, repeating the process. The video tracked the colony for 8 lysis cycles and the lysis period of this strain was 3 hours. Images were taken every 2 min at the bottom portion of a 100×100 μm chamber.

Supplementary Video 2.

A video showing timelapse fluorescence microscopy of the SDC in Strain 2 (*S. typhimurium*, ssrA tag on LuxI) at 60× magnification was taken. This video shows that a longer lysis period with a higher degradation efficiency on LuxI. The bacterial colony grew in a microfluidic chamber until it reached a quorum threshold at which the cells fluoresced (indicating the quorum activation of the circuit genes) and a fraction of the population lysed. The survivors re-populated and grew until the threshold was reached again, repeating the process. The video tracked the colony for 6 lysis cycles and the lysis period of this strain was ~6 hours. The chamber size was 100×100 μm and images were taken every 2 min.

Supplementary Video 3.

A video showing timelapse fluorescence microscopy of the SDC in Strain 13 (*E. coli*) at 60× magnification was taken. This video shows that the circuit was not as robust in *E. coli*, although regular lysis oscillations were still observed at 37° C. The bacterial colony grew in a microfluidic chamber until it reached a quorum threshold at which the cells fluoresced (indicating the quorum activation of the circuit genes) and a fraction of the population lysed. The survivors re-populated and grew until the threshold was reached again, repeating the process. The video tracked the colony for 6 lysis cycles and the lysis period of this strain was ~3 hours. The chamber size is 100×100 μm and images were taken every 2 min.

Supplementary Video 4.

A video showing timelapse fluorescence microscopy of the SDC in Strain 1 (*S. typhimurium*) at 60× magnification was taken. This video shows that, in the first part of the experiment, media with 200 nM AHL was used and the bacteria could be seen entering a constant lysis state. In the device, indicated by fluorescent dye (red channel). The media was then switched to another source without AHL, in which the fluorescent dye was absent, and the bacteria reverted back to an oscillatory state, where the colony continued for 4 lysis cycles before the end of imaging. The chamber size was 100×100 μm and images were taken every 2 min.

Supplementary Video 5.

A video showing bacteria and cancer cell co-culture on a microfluidic device at 60× magnification was taken. This video shows that Strain 3 (non-motile *S. typhimurium*, SDC with HlyE) was loaded in the growth chambers while HeLa cells grew in the main channel of the device. Bacteria could be seen growing in their chamber until they reached a quorum threshold and lyse. Upon lysis, the HeLa cells in the channel could be seen undergoing cell death. Timelapse fluorescence microscopy images were taken every 3 min.

Supplementary Video 6.

A second video of bacteria and cancer cell co-culture on a microfluidic device at 60× magnification. This video shows that Strain 3 (non-motile *S. typhimurium*, SDC with HlyE) was loaded in the growth chambers while HeLa cells grew in the main channel of the device. Bacteria could be seen growing in their chamber until they reached a quorum threshold and lysed. Upon lysis, the HeLa cells in the channel could be seen undergoing cell death. Timelapse fluorescence microscopy images were taken every 3 min.

Supplementary Video 7.

A video of bacteria and cancer cell co-culture in a tissue culture well-plate at 20× magnification was taken. This video shows that Strain 4 (motile *S. typhimurium*, SDC with HlyE) was loaded in the well with a monolayer HeLa cells. After the bacteria grew, the quorum event was visualized by the expression of green fluorescence protein (GFP). Shortly thereafter, HeLa cells could be seen exhibiting cell death. Timelapse fluorescence microscopy images were taken every 1 min.

One promise of synthetic biology is the creation of genetic circuitry that enables the execution of logical programming in living cells. Such 'wet programming' is positioned to transform a wide and diverse swathe of biotechnology ranging from therapeutics and diagnostics to water treatment strategies. Although progress in the development of a library of genetic modules continues apace (Gardner, T. S., Cantor, C. R. & Collins, J. J. Construction of a genetic toggle switch from *Escherichia coli*. *Nature* 403, 339-342; Siuti, P., Yazbek, J. & Lu, T. K. Synthetic circuits integrating logic and memory in living cells. *Nature Biotechnol*. 31, 448-452 (2013); Tigges, M., Marquez-Lago, T., Stelling, J. & Fussenegger, M. A tunable synthetic mammalian oscillator. *Nature* 457, 309-312 (2009); Xie, Z., Wroblewska, L., Prochazka, L., Weiss, R. & Benenson, Y. Multi-input RNAi-based logic circuit for identification of specific cancer cells. *Science* 333, 1307-1311 (2011)), a major challenge for their integration into larger circuits is the generation of sufficiently fast and precise communication between modules (Moon, T. S., Tamsir, A., Stanton, B. C. & Voigt, C. A. Genetic programs constructed from layered logic gates in single cells. *Nature* 491, 249-253, 2012; Del Vecchio, D., Ninfa, A. J. & Sontag, E. D. Modular cell biology: retroactivity and insulation. *Mol. Syst. Biol*. 4, 161, 2008). An attractive approach is to integrate engineered circuits with host processes that facilitate robust cellular signalling (Nandagopal, N. & Elowitz, M. B. Synthetic biology: integrated gene circuits. *Science* 333, 1244-1248 (2011)). In this context, recent studies have demonstrated that bacterial protein degradation can trigger a precise response to stress by overloading a limited supply of intracellular proteases (Fredriksson, A. et al. Decline in ribosomal fidelity contributes to the accumulation and stabilization of the master stress response regulator GS upon carbon starvation. *Genes Dev*. 21, 862-874 (2007); Merrikh, H., Ferrazzoli, A. E., Bougdour, A., Olivier-Mason, A. & Lovett, S. T. A DNA damage response in *Escherichia coli* involving the alternative sigma factor, RpoS. *Proc. Natl Acad. Sci. USA* 106, 611-616 (2009); Cookson, N. A. et al. Queueing up for enzymatic processing: correlated signaling through coupled degradation. *Mol. Syst. Biol.* 7, 561 (2011)). Here we use protease competition to engineer rapid and tunable coupling of genetic circuits across multiple spatial and temporal scales. We characterize coupling delay times that are more than an order of magnitude faster than standard transcription factor-based coupling methods (less than 1 min compared with ~20-40 min) and demonstrate tunability through manipulation of the linker between the protein and its degradation tag. We use this mechanism as a platform to couple genetic clocks at the intracellular and colony level, and then synchronize the multi-colony dynamics to reduce variability in both clocks. We show how the coupled clock network can be used to encode independent environmental inputs into a single time series output, thus enabling frequency multiplexing (information transmitted on a common channel by distinct frequencies) in a genetic circuit context. Our results establish a general framework for the rapid and tunable coupling of genetic circuits through the use of native 'queueing' processes such as competitive protein degradation.

Figure 10A:
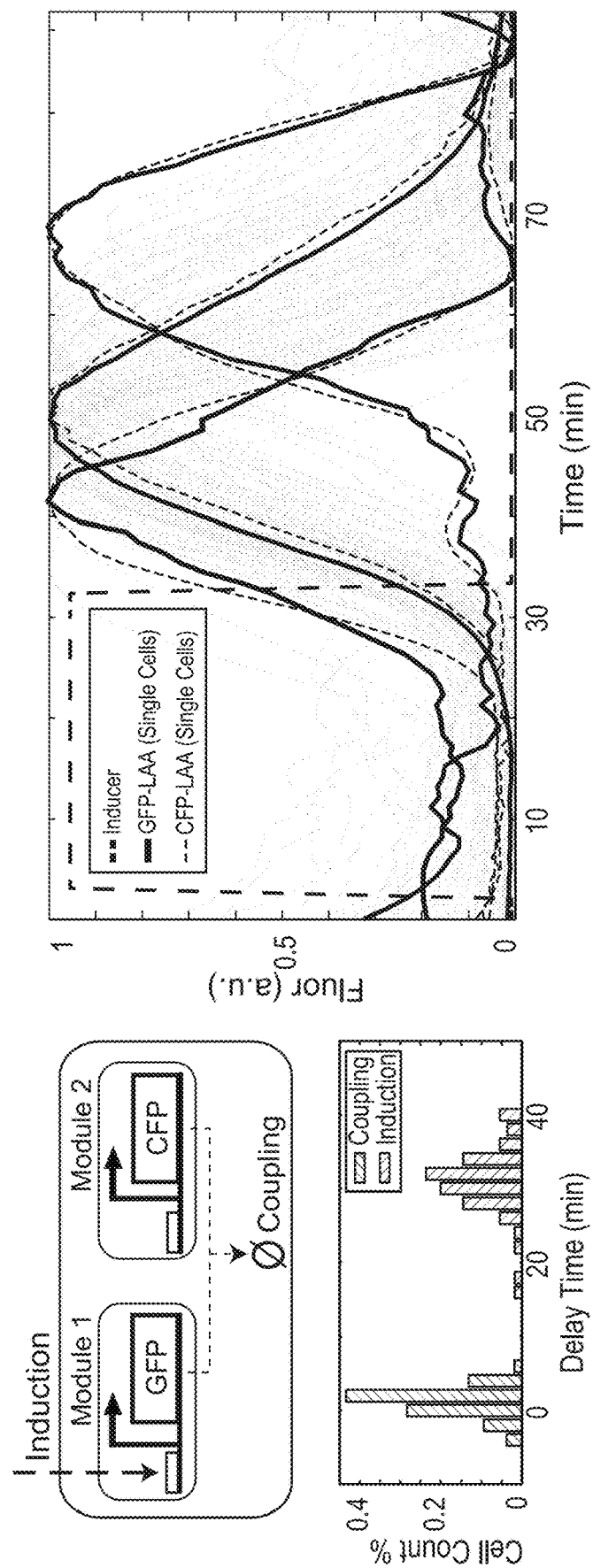
FIG. 10. A rapid post-translational coupling platform based on shared degradation. (A) We measured the delays associated with module-module coordination by ClpXP degradation (1±1 min (±s.e.m.), represented by dotted line arrow) and input-output response through transcription and translation (31±5 min) in a single experiment by inducing (dashed line arrow) the lux promoter and tracking the response of superfolder GFP (sfGFP)-LAA (lux promoter, arrowed solid line) and CFP-LAA ($P_{lac/ara-1}$ promoter, arrowed solid line) in single cells (right panel, 55 gray cell trajectory pairs with 3 representative pairs highlighted). (B) Rapid (<2 min, our experimental time-step) induction of protein degradation by externally provided $H_2O_2$ produces reversible changes in ClpXP load in response to obstruction of RssB (C) To use post-translational coupling to drive downstream modules, we linked a quorum clock to a constitutively expressed fluorescent protein via the addition of identical LAA tags. With identical degradation tags, the constitutive module couples tightly to the quorum pacemaker. The addition of a variable-length linker (Thr-Ser (TS) repeats) before the degradation tag phase-shifts the degradation dynamics, where longer linkers produced longer delays. Error bars indicate standard deviation (s.d.) of offset time, centred at the mean (50-200 cells for each TS-linker length). a.u., arbitrary units.
Figure 10B:
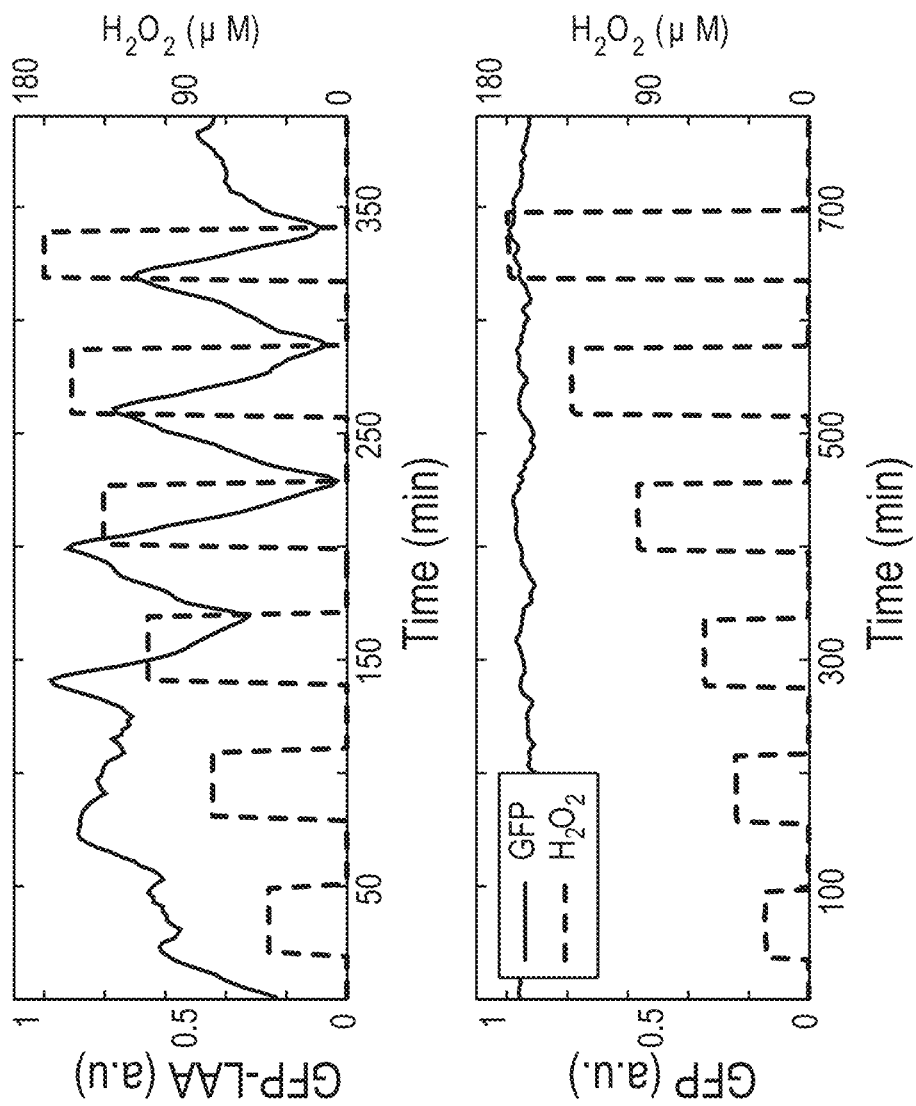

To engineer rapid coupling between synthetic genetic modules, we developed a post-translational coupling platform that operates via shared degradation by the ClpXP protease (FIG. 10A). In this scheme, all LAA-tagged components (Keiler, K. C., Waller, P. & Sauer, R. Role of a peptide tagging system in degradation of proteins synthesized from damaged messenger RNA. *Science* 271, 990-993 (1996)) are dynamically linked through competition for a limited number of proteases (Keiler, K. C., Waller, P. & Sauer, R. Role of a peptide tagging system in degradation of proteins synthesized from damaged messenger RNA. *Science* 271, 990-993 (1996); Goldbeter, A. & Koshland, D. E. An amplified sensitivity arising from covalent modification in biological systems. *Proc. Natl Acad. Sci. USA* 78, 6840-6844 (1981)), such that tagged modules remain tightly aligned (1±1 min (±s.e.m.), GFP-CFP (green fluorescent protein-cyan fluorescent protein) experimental trajectory pairs in FIG. 10A) despite significant induction delay (31±5 min, time elapsed from addition of inducer to GFP appearance in FIG. 10A). This coupling method produces delays that are more than an order of magnitude faster than standard transcription-factor-based coupling methods (~20-40 min) (Rosenfeld, N. & Alon, U. Response delays and the structure of transcription networks. *J. Mol. Biol.* 329, 645-654 (2003); Hooshangi, S., Thiberge, S. & Weiss, R. Ultrasensitivity and noise propagation in a synthetic transcriptional cascade. *Proc. Natl Acad. Sci. USA* 102, 3581-3586 (2005)). To illustrate directly the response time that can be achieved by coordinating module output via modulating ClpXP activity, we show that low levels (90 mM) of externally provided $H_2O_2$ 'inducer' rapidly (<2 min, our experimental time-step) and reversibly modulates the concentration of constitutively expressed GFP in a ClpXP-dependent manner (FIG. 10B). Here, $H_2O_2$ reduces the native substrate load on ClpXP by obstructing RssB, the adaptor protein that targets the alternative sigma factor RpoS for degradation by ClpXP (Fredriksson, A. et al. Decline in ribosomal fidelity contributes to the accumulation and stabilization of the master stress response regulator σS upon carbon starvation. *Genes Dev.* 21, 862-874 (2007); Merrikh, H., Ferrazzoli, A. E., Bougdour, A., Olivier-Mason, A. & Lovett, S. T. A DNA damage response in *Escherichia coli* involving the alternative sigma factor, RpoS. *Proc. Natl Acad. Sci. USA* 106, 611-616 (2009); Mika, F. & Hengge, R. A two-component phosphotransfer network involving ArcB, ArcA, and RssB coordinates synthesis and proteolysis of σS (RpoS) in *E. coli*. *Genes Dev.* 19, 2770-2781 (2005)). As RpoS is continuously produced and degraded by ClpXP, inactivating its rate-limiting adaptor protein results in an instantaneous increase in the effective ClpXP degradation rate for LAA-tagged proteins (Pruteanu, M. & Hengge-Aronis, R. The cellular level of the recognition factor RssB is transduction in σS turnover in *Escherichia coli*. *Mol. Microbiol.* 45, 1701-1713 (2002)).

Figure 10C:
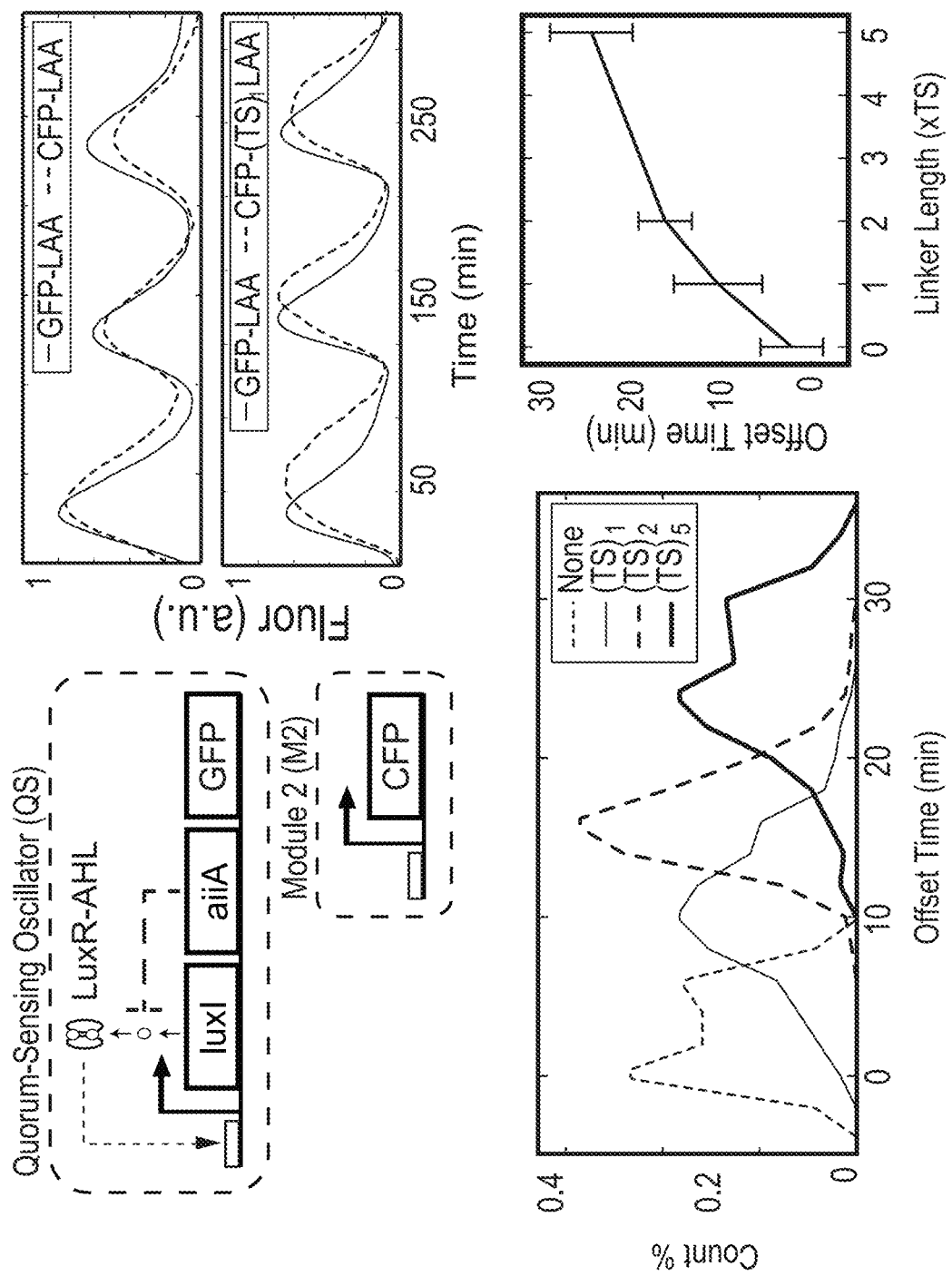

We systematically explored the coupling mechanism by driving a constitutive module with a quorum-sensing clock (FIG. 10C). As the pacemaker, the quorum clock generates density-dependent synchronous oscillations at the colony level via acyl-homoserine lactone (AHL), a small molecule capable of synchronizing cellular behaviour across distances up to 100 μm (Danino, T., Mondrago'n-Palomino, O., Tsimring, L. & Hasty, J. A synchronized quorum of genetic clocks. *Nature* 463, 326-330 (2010)). Using microfluidic devices (Unger, M. A., Chou, H.-P., Thorsen, T., Scherer, A. & Quake, S. R. Monolithic microfabricated valves and pumps by multilayer soft lithography. *Science*, 288, 113-116 (2000)) we observed the colony-level expression of the constitutive module, and found that oscillating expression was synchronized to the quorum clock (FIG. 10C, top right). We then constructed a library of degradation tags by adding a series of variable-length spacer regions between the downstream protein and its degradation tag. Spacer regions contained between one and five copies of the amino acid sequence 'Thr-Ser' (TS) and their effects on offset time compared to that of a previously published alternative degradation tag (FIG. 14B-F). Although all spacer sequences produced synchronous activation dynamics, the degradation dynamics of the downstream module were offset depending on the length of the linker sequence, where longer linkers produced greater GFP-CFP offset time (FIG. 10C, bottom). Thus, our ClpXP coupling platform rapidly links genetic modules through shared degradation and permits tuning the strength and timing of coupling by changing the degradation kinetics of individual modules.

To engineer coupling between genetic modules capable of generating their own dynamics, we designed a circuit containing the quorum clock and a variant of a previously described intracellular clock (FIG. 11A) (Stricker, J. et al. A fast, robust and tunable synthetic gene oscillator. *Nature* 456, 516-519 (2008)). This intracellular clock variant based on the $P_{lac/ara-1}$ promoter retains the fast dynamics and simple genetic architecture of the published version that uses the $P_{LlacO-1}$ promoter. The intracellular clock is based off of a negative feedback loop with delay that results in oscillations. The $P_{lac/ara-1}$ or $P_{LlacO-1}$ promoters drive the expression of their transcriptional repressor, the LacI protein. The delay caused in the folding and maturation of the LacI repressor results in oscillatory bursts of transcriptional activity. More generally, this negative feedback motif that results in oscillations may be constructed using other promoter/repressor combinations, such as tet repressible promoters driving TetR, or the lambda promoter driving the cI repressor. The period of the $P_{lac/ara-1}$ promoter based intracellular clock is tunable by both isopropyl-β-$_D$-1-thiogalactopyranoside (IPTG) and arabinose in the presence of chromosomal araC. We first used small microfluidic devices (100 cells) and observed fast and asynchronous intracellular clock oscillations without quorum clock contribution, as the quorum clock requires a critical colony size to function. In larger devices (5,000 cells), we observed a transition from asynchronous oscillations to identical intracellular and quorum clock oscillations as the population grew larger (FIG. 11B). In the case of the larger population, the substrate load on ClpXP during the quorum clock pulse is sufficient to shift the intracellular clock out of its oscillatory regime, enabling complete linkage between the two clocks despite their vastly different spatial and temporal scales. Thus, despite lacking a mode of cell-cell communication itself, the intracellular clock is effectively synchronized at the colony level through ClpXP-mediated coupling with the quorum clock.

Figure 11A:
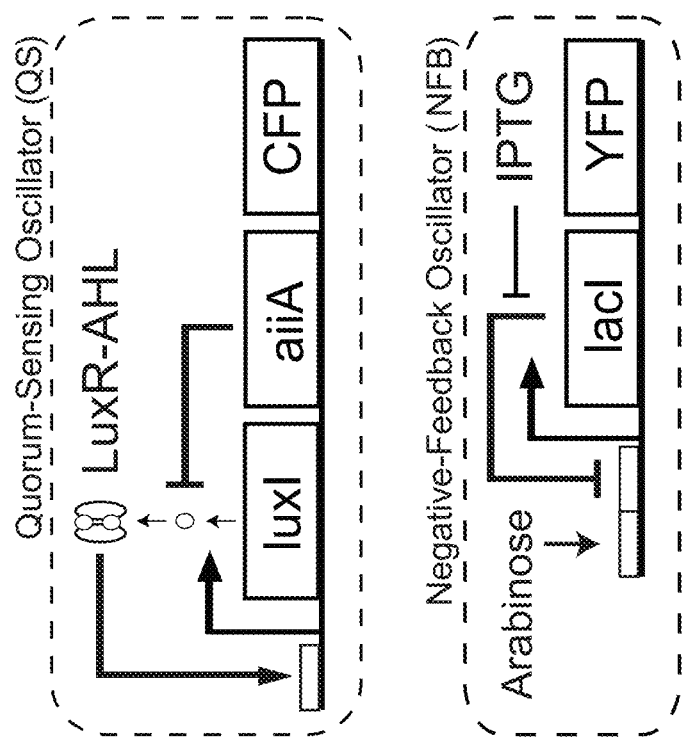
FIG. 11. Post-translationally linked genetic clocks at multiple scales. (A) The network is composed of coupled intracellular quorum clock. The intracellular clock oscillates as a result of delayed negative feedback on its own promoter and its period is tunable by IPTG and arabinose. Quorum clock oscillations are tunable by media flow rate and are synchronized via AHL at the colony level. (B) The coupled intracellular quorum clock system oscillates asynchronously in small populations and transitions to synchronized oscillations in larger populations once the quorum clock fires. Despite lacking a mode of cell-cell communication itself, the coefficient of variation (CV) of the intracellular clock drops markedly through host-linked coupling with the quorum clock (bottom, data from 28 single-cell traces). (C) IPTG reduces the intracellular clock period in small cell populations without the quorum clock (solid line) and increases the coupled period in larger populations with the quorum clock (dashed line). Each data point taken from 10-30 oscillatory peaks. Error bars indicate s.e.m. of the period, centred at the mean. (D) In our computational model, load-mediated coupling allows the intracellular clock to modulate the quorum clock period via degradation coupling at ClpXP, since the intracellular clock continues oscillating between coupled pulses and accelerates the pulse onset. (E) This adaptive form of pulse frequency modulation ensures that the pulse dynamics remain unchanged while the inter-pulse duration is adjusted (left, model; right, experimental; 6-9 oscillatory peaks). Inset shows the earlier onset of the coupled pulse due to the intracellular clock. Error bars indicate s.e.m. of relative quorum clock period. (F) This mechanism also makes the coupled system more robust by enabling oscillation at higher media flow rates. NFB, negative-feedback oscillator; QS, quorum-sensing oscillator.
Figure 11B:
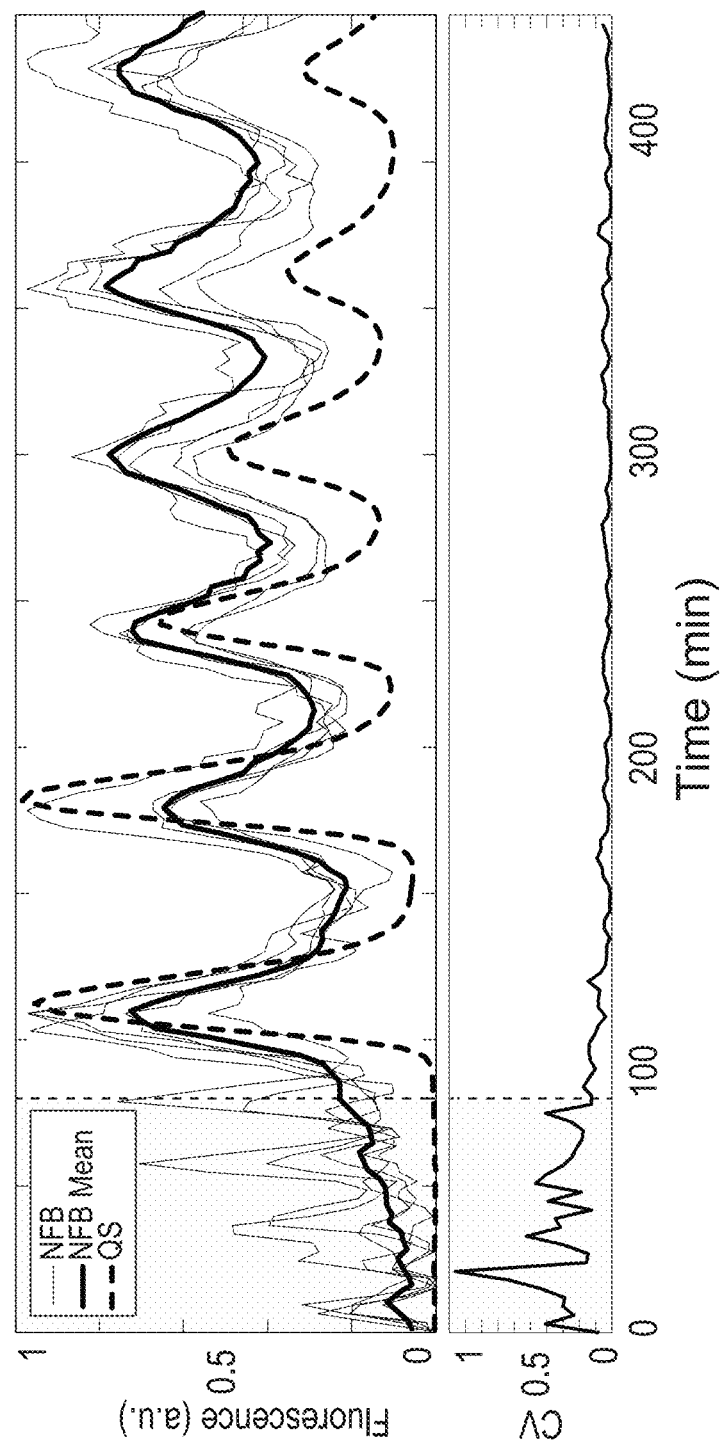

We found that changing the intracellular clock period of individual cells indirectly tuned the quorum clock period, as IPTG values associated with longer intracellular clock periods inversely produced shorter quorum clock periods (FIG. 11C). We developed a computational model of the oscillator network involving a form of load-mediated pulse frequency modulation to explain this effect (FIG. 11D-F). Between coupled pulses, the intracellular clock accelerates the quorum pulse onset through load mediated decreases in the degradation rate of LuxI, since larger intracellular clock load produces higher levels of the AHL-synthase (FIG. 11E, left, and FIG. 11A-E). During the coupled pulse, contributions of the intracellular clock leave the duration of the pulse itself unchanged (FIG. 11e, left (model) and right (experimental)). Linking the intracellular and quorum clocks through degradation also yielded an expansion in the oscillatory regime for the coupled system with respect to flow rate compared to the quorum clock alone (FIG. 11F). In this way, the intracellular clock continually excites the quorum clock to fire, enabling more robust function at higher external flow rates (FIG. 12A-C).

Figure 12A:
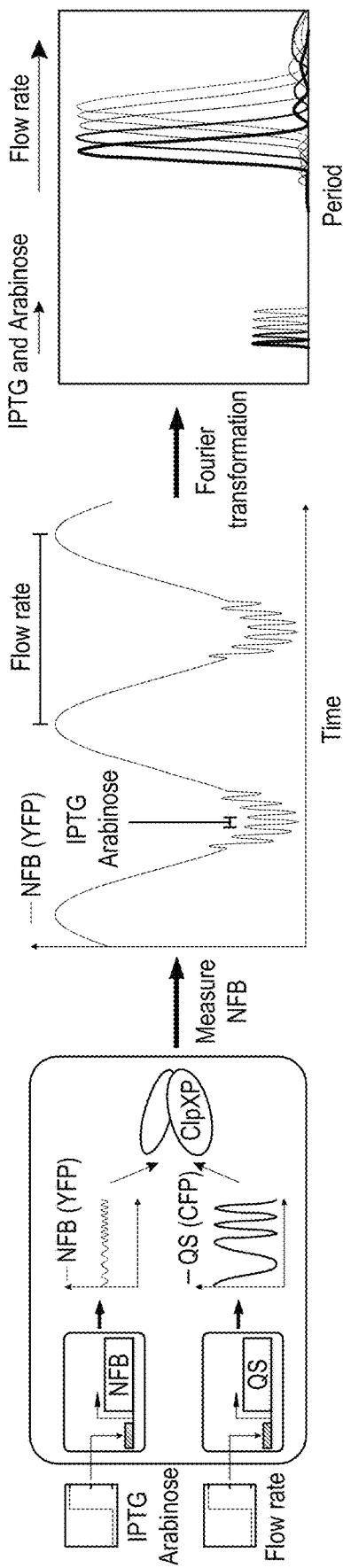
FIG. 12. Genetic multispectral encoding. (A) Separate IPTG and arabinose, and flow rate inputs are encoded into frequency-modulation oscillations that can be measured from the time series of the reporter for the intracellular clock. This engineered system is capable of encoding information from two underlying networks into a single multispectral time series. Thick solid line: QS (CFP); Thin solid line: NBF (YFP). (B) Frequency response curves generated from experimental data and computational models for the intracellular clock (top, data from 30 single-cell traces each) and quorum clock (bottom, model applied to data from the original study in isolation. Error bars indicate s.e.m. of the period, centred at the mean. (C) In the coupled system, frequency-modulated oscillations from both clocks can be observed in the output of the intracellular clock and extracted by inverse Fourier transformation (inset, methods in Supplementary Information. (D) Independent recovery of both IPTG and arabinose and flow rate inputs. The frequency response of the intracellular clock to IPTG and arabinose is equivalent to the isolated clock (top) and the frequency response of the quorum clock is shifted by the intracellular clock (bottom). Periods calculated from 5-10 single-cell traces for each condition. Error bars indicate s.e.m. of the period, centred at the mean.

With a platform for rapidly coupling genetic clocks at multiple scales, we sought to engineer a system capable of frequency-encoding information from both clocks into the multispectral time series of a single reporter (FIG. 12A). Here, the measured output of the intracellular clock reporter contains contributions from its own fast intracellular clock dynamics between slow quorum clock bursts. As the range of natural periods for the faster $P_{lac/ara-1}$ intracellular clock is fully separated from the slower quorum clock (Danino, T., Mondrago'n-Palomino, O., Tsimring, L. & Hasty, J. A synchronized quorum of genetic clocks. Nature 463, 326-330 (2010); Stricker, J. et al. A fast, robust and tunable synthetic gene oscillator. Nature 456, 516-519 (2008)), both IPTG and arabinose and flow rate inputs can be encoded into frequency-modulated oscillations in the time domain and independently extracted by Fourier transform. Thus, the measurement of a single clock history reveals the activities both underlying clock networks.

Figure 12B:
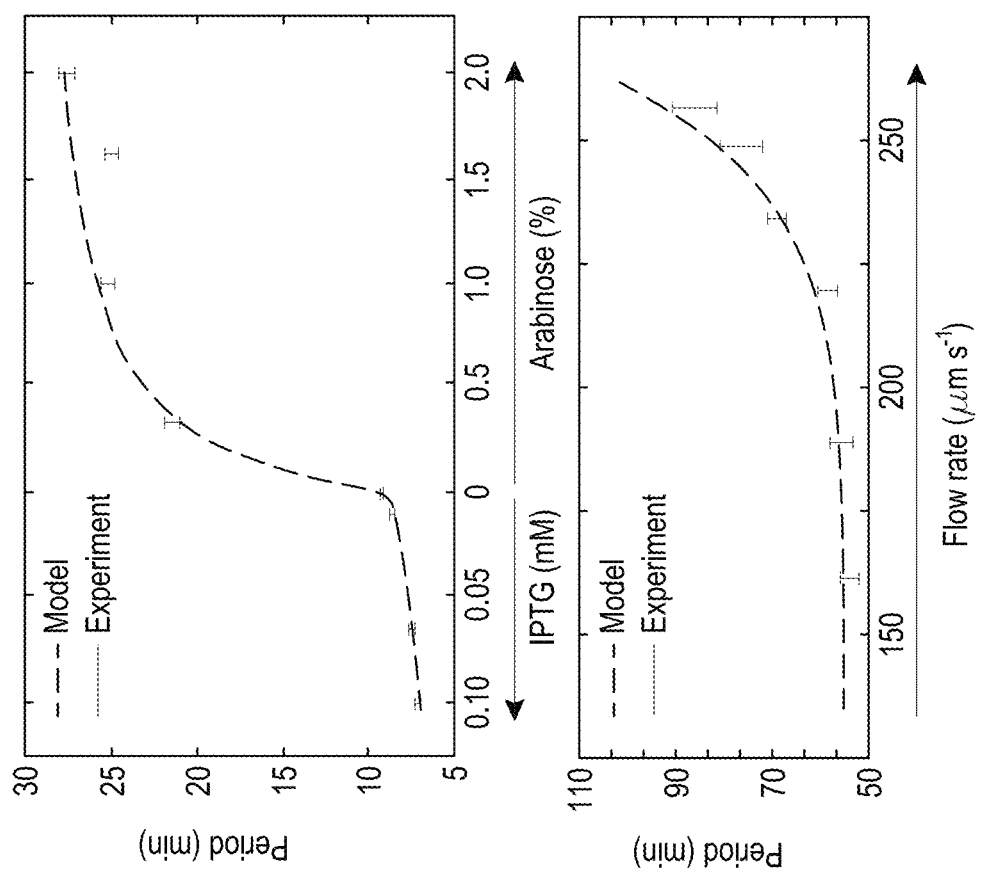
Figure 12C:
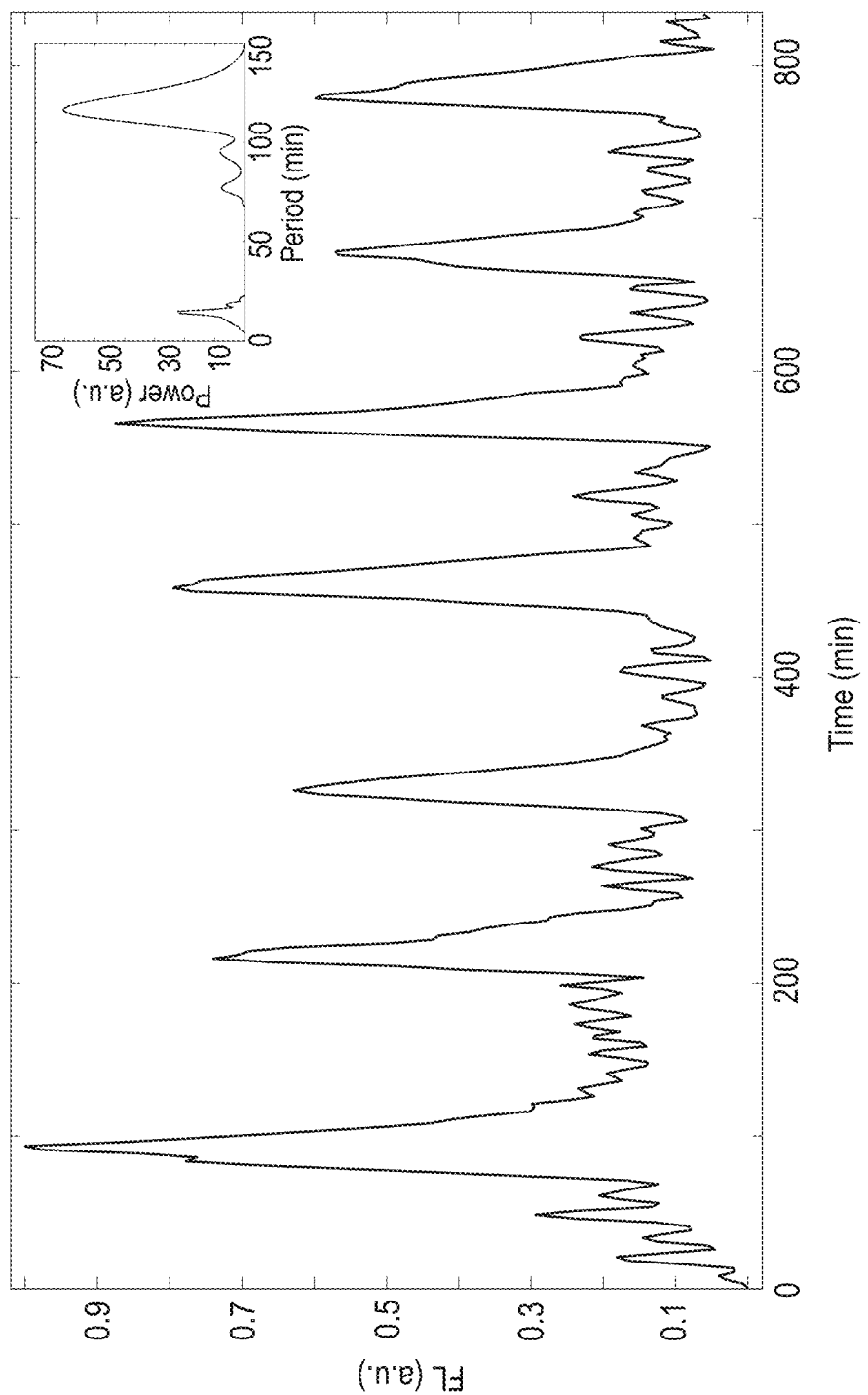
Figure 12D:
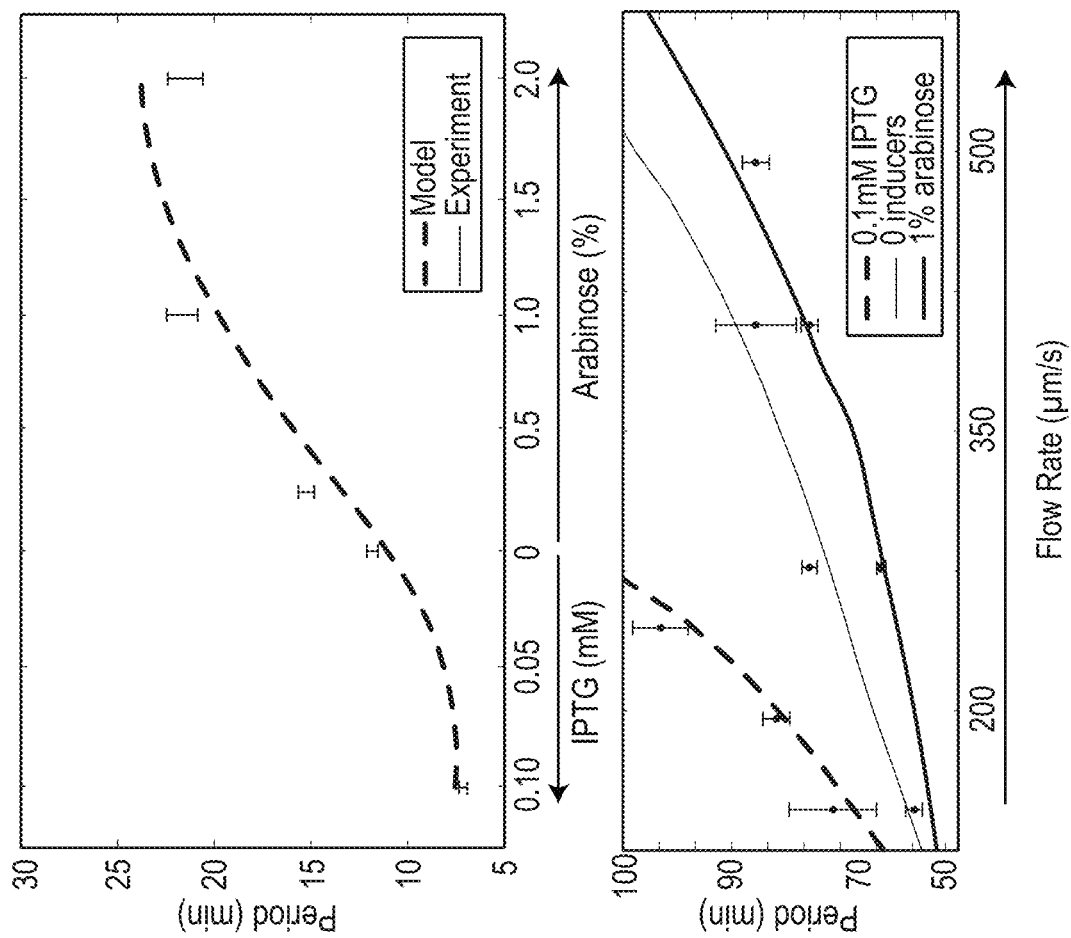

We began by characterizing the frequency response curves for both the intracellular and quorum clocks in isolation, finding ranges of 7-25 min and 55-95 min, respectively, when sweeping IPTG and arabinose, and flow rate inputs (FIG. 12B, top (intracellular clock in araC1 strain) and bottom (quorum clock, original study data) (Marguet, P., Tanouchi, Y., Spitz, E., Smith, C. & You, L. Oscillations by minimal bacterial suicide circuits reveal hidden facets of host-circuit physiology. PloS One 5, e11909 (2010)). We then measured trajectories taken from the coupled clock system and extracted the frequency components of both clocks by Fourier transform (Press, W. H. in Numerical Recipes: The Art of Scientific Computing 3rd ed. (Cambridge Univ. Press, 2007)) (FIG. 3C and Methods Summary). In sweeping IPTG and arabinose inducers, we found the frequency response of the intracellular clock contribution to the multispectral reporter to be unchanged by the inclusion of the quorum clock since the intracellular frequency response to IPTG and arabinose was equivalent to the isolated clock (FIG. 12D, top (coupled), and FIG. 12B, top (isolated)). We then swept flow rates at three fixed inducer levels, and found distinct response curves for the quorum clock contribution to the multispectral reporter shifted in accordance with our model for ClpXP-mediated frequency modulation by the intracellular clock (FIG. 12D, bottom). Thus, to decode a given pair of IPTG and arabinose, and flowrate inputs, we first recover the intracellular clock frequency as a measure of IPTG and arabinose and then use the corresponding quorum clock response curve to measure flow rate.

Figure 13A:
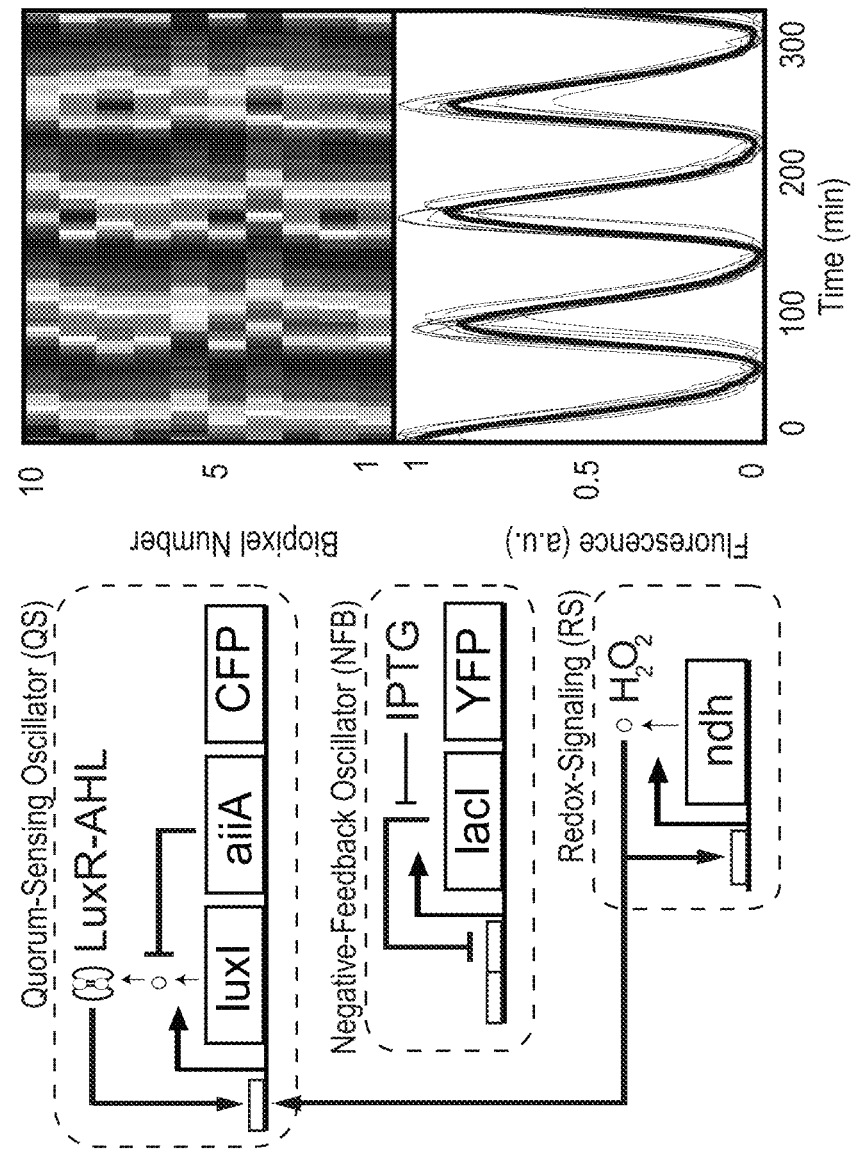
FIG. 13. Post-translational coupling at the multi-colony level. (A) At the multi-colony level, interaction of $H_2O_2$ generated by redox signalling with the cellular stress response network synchronizes quorum clock oscillations between colonies. Traces taken from 10 separate colonies across the array. (B) Host-linked oscillations change distinct aspects of the waveform in response to $H_2O_2$ produced by the enzymatic activity of NDH (NADH dehydrogenase II). With $H_2O_2$ (dashed line), oscillations have larger amplitudes and steeper downslopes, revealing increases in both transcription and degradation produced by the interaction of the synthetic clock network with the native stress response. Dark lines indicate the means of all trajectories. (C) $H_2O_2$ increases the oscillatory amplitude while decreasing the required degradation time, revealing an increase in ClpXP activity. Solid line: no $H_2O_2$; Dashed line: with $H_2O_2$. This increase in ClpXP capacity in response to $H_2O_2$ serves to mitigate the effects of transcriptional noise by minimizing the effects of amplitude variation on the period, resulting in a tightening of the period distribution with $H_2O_2$ (model, FIG. 17C, FIG. 17D).
Figure 13B:
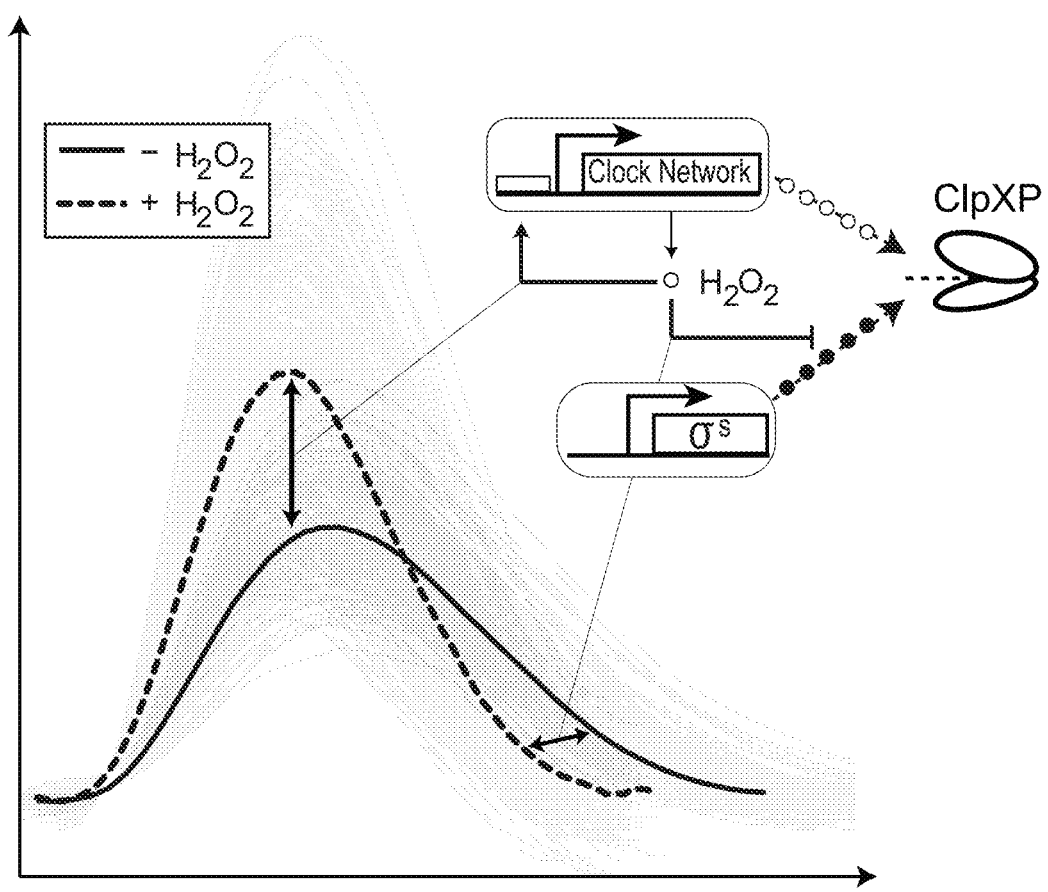
Figure 13C:
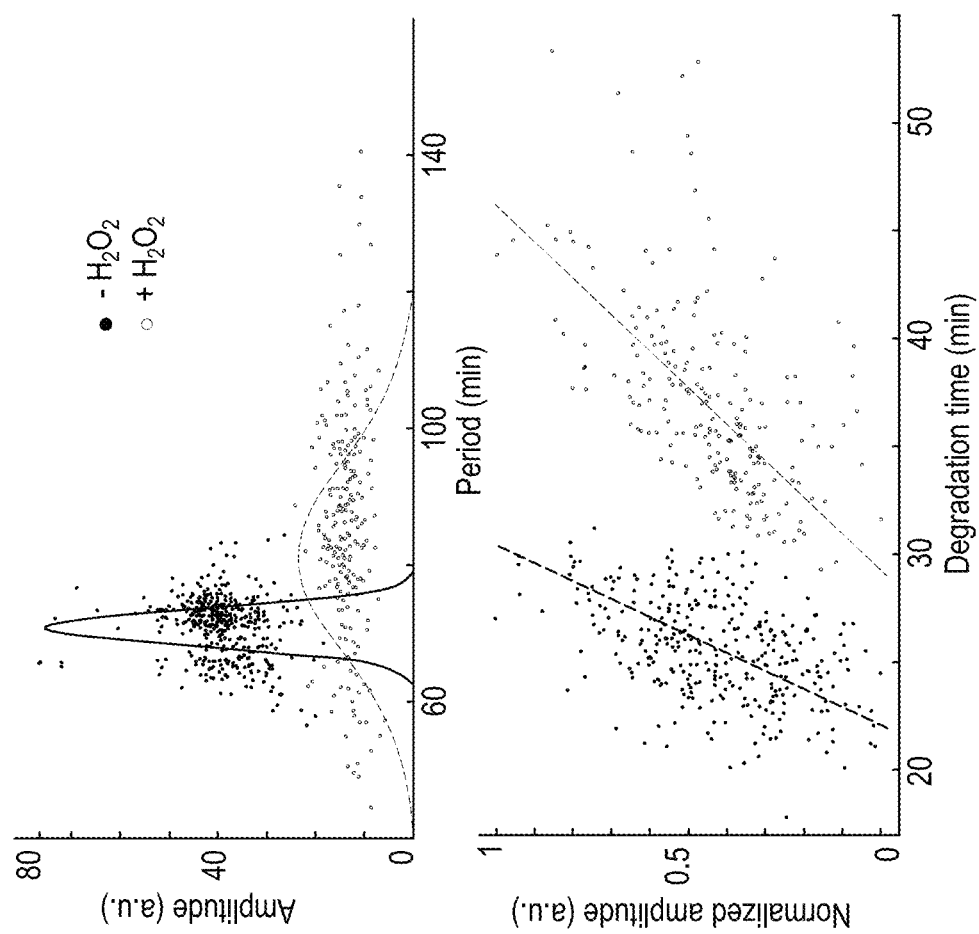
Figure 17B:
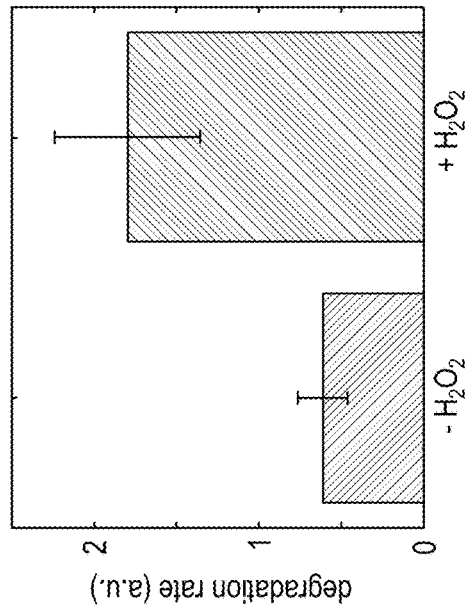
FIG. 17. $H_2O_2$ increases the degradation rate by ClpXP, and this in combination with transcriptional increase at the lux promoter decreases variability in the oscillator period. (A) There is a significant decrease in the degradation time due to $H_2O_2$ (experimental). (B) Decrease in the degradation time due to $H_2O_2$ is due to effective increase in ClpXP degradation rate (experimental). (C) $H_2O_2$ activation of lux promoter alone would only increase the amplitude of quorum clock oscillations. Similarly, $H_2O_2$-dependent increase in ClpXP activity results only in steeper degradation and longer inter-pulse duration. Combination of the two effects leads to increase in amplitude and decrease in inter-pulse duration, which matches experiments (model). (D) Individually, the two $H_2O_2$ effects do little to lower the quorum clock period CV, which is reduced when both are present (model).
Figure 17D:
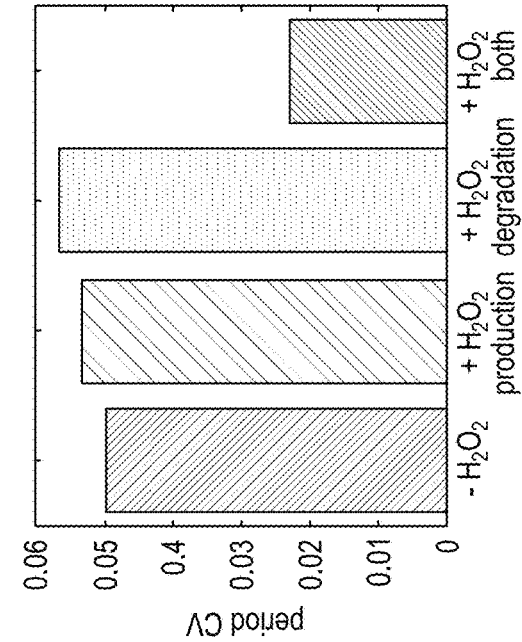
Figure 17A:
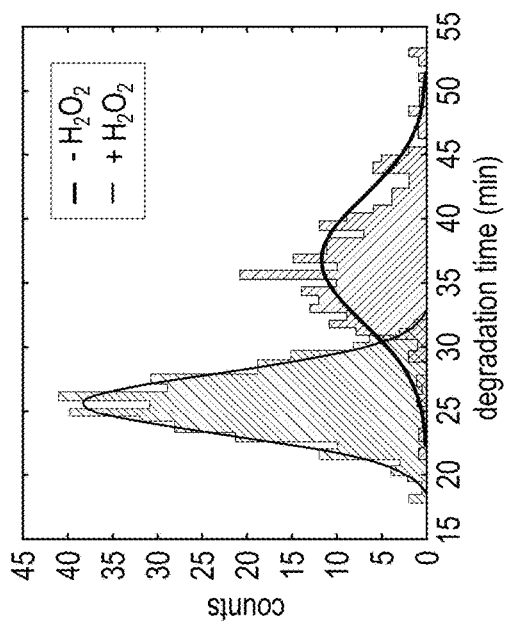
Figure 17C:
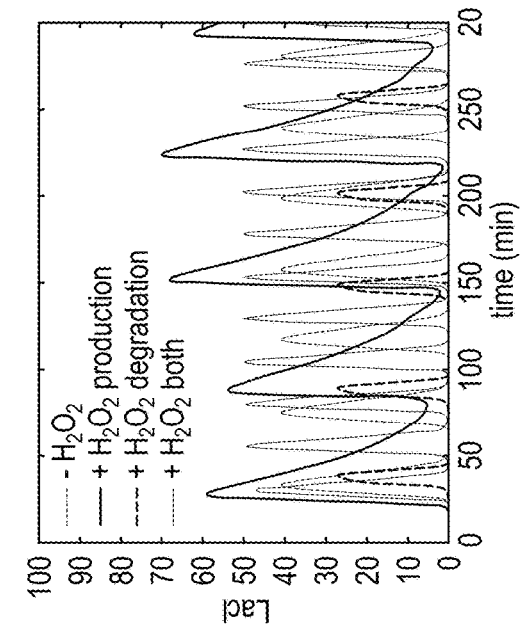

To extend rapid coupling to greater spatial scales, we added a genetic $H_2O_2$ signalling (Prindle, A. et al. A sensing array of radically coupled genetic 'biopixels'. Nature 481, 39-44 (2012)) cassette to the network and observed synchronization at the multi-colony level (FIG. 13A). In conducting these experiments, we also observed $H_2O_2$-mediated interaction between the native stress response network and our synthetic circuit at ClpXP (FIG. 13B). In the original design, $H_2O_2$ synchronized quorum clock oscillations by transcriptional upregulation of the lux promoter via the aerobic response control system ArcAB (Prindle, A. et al. A sensing array of radically coupled genetic 'biopixels'. Nature 481, 39-44 (2012)). In addition to transcriptional increase (FIG. 13C, top), we found an increase in the apparent degradation rate with $H_2O_2$ (FIG. 13C, bottom, and FIGS. 17A and 17B), consistent with increased ClpXP activity in response to externally provided $H_2O_2$. The coupled increases in transcriptional output and effective ClpXP degradation rate in response to $H_2O_2$ also tightens the period distribution at the multi-colony level by mitigating the effects of period variation in an individual colony (FIG. 13C, top, and FIG. 17C, 17D).

Engineering synthetic circuits composed of interacting modules is an ongoing effort (Gardner, T. S., Cantor, C. R. & Collins, J. J. Construction of a genetic toggle switch from Escherichia coli. Nature 403, 339-342; Siuti, P., Yazbek, J. & Lu, T. K. Synthetic circuits integrating logic and memory in living cells. Nature Biotechnol. 31, 448-452 (2013); Tigges, M., Marquez-Lago, T., Stelling, J. & Fussenegger, M. A tunable synthetic mammalian oscillator. Nature 457, 309-312 (2009); Xie, Z., Wroblewska, L., Prochazka, L., Weiss, R. & Benenson, Y. Multi-input RNAi-based logic circuit for identification of specific cancer cells. Science 333, 1307-1311 (2011); Moon, T. S., Tamsir, A., Stanton, B. C. & Voigt, C. A. Genetic programs constructed from layered logic gates in single cells. Nature 491, 249-253 (2012); Del Vecchio, D., Ninfa, A. J. & Sontag, E. D. Modular cell biology: retroactivity and insulation. Mol. Syst. Biol. 4, 161 (2008)) that has generally relied on transcription and translation, with less attention paid to post-translational coupling mechanisms (Grünberg, R. & Serrano, L. Strategies for protein synthetic biology. Nucleic Acids Res. 38, 2663-2675, 2010).

Protease competition offers the advantages of rapid response, modularity with distinct recognition sequences, and simultaneous control over multiple circuits with protease adapters (McGinness, K. E., Baker, T. A. & Sauer, R. T. Engineering controllable protein degradation. Mol. Cell 22, 701-707 (2006); Griffith, K. L. & Grossman, A. D. Inducible protein degradation in Bacillus subtilis using heterologous peptide tags and adaptor proteins to target substrates to the protease ClpXP. Mol. Microbiol. 70, 1012-1025 (2008)). More generally, in natural biological networks, competition for cellular resources (for example, metabolites, enzymes, transcription factors, binding sites) produces nonlinear coupling effects that serve to reduce noise, increase sensitivity to input concentrations, and discriminate between multiple inputs (Goldbeter, A. & Koshland, D. E. An amplified sensitivity arising from covalent modification in biological systems. *Proc. Natl Acad. Sci. USA* 78, 6840-6844 (1981); Burger, A., Walczak, A. M. & Wolynes, P. G. Abduction and asylum in the lives of transcription factors. *Proc. Natl Acad. Sci. USA* 107, 4016-4021 (2010); Mukherji, S. et al. MicroRNAs can generate thresholds in target gene expression. *Nature Genet.* 43, 854-859 (2011); Buchler, N. E. & Louis, M. Molecular titration and ultrasensitivity in regulatory networks. *J. Mol. Biol.* 384, 1106-1119 (2008); Strogatz, S. Nonlinear Dynamics and Chaos: with Applications to Physics, Biology, Chemistry and Engineering (Perseus Books, 2001)). We envision that coordinating engineered circuits via built-in cellular processes—what we term 'host-linked' coupling—has the potential to produce more sophisticated circuits by facilitating robust signalling between synthetic modules.

Recent advances in the forward engineering of genetic circuits have positioned synthetic biology as a novel approach for developing biological therapies (Fischbach, M. A., Bluestone, J. A. & Lim, W. A. Cell-based therapeutics: the next pillar of medicine. *Science Translational Medicine* 5, 179 ps7-179ps7, 2013; Ruder, W. C., Lu, T. & Collins, J. J. Synthetic biology moving into the clinic. *Science* 333, 1248-1252, 2011; Weber, W. & Fussenegger, M. Emerging biomedical applications of synthetic biology. *Nature Reviews Genetics* 13, 21-35, 2011; and Folcher, M. & Fussenegger, M. Synthetic biology advancing clinical applications. Current opinion in chemical biology, 2012). Given the widespread prevalence of beneficial microbes and their functional roles within the body, bacteria represent a natural platform for the development of biological therapies in the treatment of metabolic disorders, gastrointestinal disease, and cancer (Cho, I. & Blaser, M. J. The human microbiome: at the interface of health and disease. *Nature Reviews Genetics* 13, 260-270 (2012); Garrett, W. S. Cancer and the microbiota. *Science* 348, 80-86, 2015; Pawelek, J. M., Low, K. B. & Bermudes, D. Tumor-targeted *Salmonella* as a novel anticancer vector. *Cancer Research* 57, 4537-4544, 1997). With continued progress in the development of modules for therapeutic gene expression, an unexplored possibility is the construction of circuits which dynamically control colony growth and therapeutic expression (Jeong, J.-H. et al. Antitumoral effect of the mitochondrial target domain of noxa delivered by an engineered *Salmonella typhimurium*. *PloS One* 9, e80050, 2014; Loessner, H. et al. Remote control of tumour-targeted *Salmonella enterica serovar typhimurium* by the use of 1-arabinose as inducer of bacterial gene expression in vivo. *Cellular Microbiology* 9, 1529-1537, 2007; Swofford, C. A., Van Dessel, N. & Forbes, N. S. Quorum-sensing *Salmonella* selectively trigger protein expression within tumors. *Proceedings of the National Academy of Sciences* 112, 3457-3462, 2015). These engineered bacteria would ideally self-maintain their population density while continually producing and releasing therapeutic agents in situ. Among the embodiments described herein is the use of an engineered bacterium with clinically relevant characteristics to lyse synchronously at a threshold population density and to release genetically encoded therapeutics. Upon lysis, a small number of surviving bacteria reseed the growing population, thus leading to pulsatile lysis and release cycles. We use microfluidic devices to characterize the robustness and tunability of the genetic circuit, and we demonstrate its prospect as an anti-cancer agent in co-culture with human cancer cells in vitro. We then inject the 'synchronized lysis strain' into grafted syngeneic colorectal tumors in mice and use a luciferase reporter to observe pulsatile colony dynamics in vivo. Guided by previous findings that bacteria can provide a natural supplement to chemotherapies (Dang, L. H., Bettegowda, C., Huso, D. L., Kinzler, K. W. & Vogelstein, B. Combination bacteriolytic therapy for the treatment of experimental tumors. *Proceedings of the National Academy of Sciences* 98, 15155-15160, 2001), we tested our system an animal model, which remain the paradigm in preclinical testing despite their imperfect prediction of human outcomes (Begley, C. G. & Ellis, L. M. Drug development: Raise standards for preclinical cancer research. *Nature* 483, 531-533 2012; Sausville, E. A. & Burger, A. M. Contributions of human tumor xenografts to anticancer drug development. *Cancer Research* 66, 3351-3354, 2006). We use a combination of chemotherapy and engineered bacteria in an experimental syngeneic transplantation model of hepatic colorectal metastases to demonstrate therapeutic potential, and find that the combination therapy leads to a notable reduction of tumor burden along with a marked survival benefit. Our approach may enable novel delivery strategies using engineered bacteria in conjunction with traditional medicine, novel biological therapeutics, or nanoparticles (Cheong, I. et al. A bacterial protein enhances the release and efficacy of liposomal cancer drugs. *Science* 314, 1308-1311, 2006; O'Shea, C. C. Viruses—seeking and destroying the tumor program. Oncogene 24, 7640-7655, 2005; June, C. H. et al. Engineered t cells for cancer therapy. *Cancer Immunology, Immunotherapy,* 1-7, 2014).

In order to control population levels and facilitate drug delivery in a therapeutic strain of bacteria, we engineered a synchronized lysis circuit (SLC) using coupled positive and negative feedback loops that have previously been used to generate robust oscillatory dynamics (Danino, T., Mondragón-Palomino, O., Tsimring, L. & Hasty, J. A synchronized quorum of genetic clocks. *Nature* 463, 326-330, 2010; Prindle, A. et al. A sensing array of radically coupled genetic 'biopixels'. *Nature* 481, 39-44, 2012). The circuit (FIG. 1A) consists of a common promoter that drives expression of both its own activator (positive feedback) and a lysis gene (negative feedback). Specifically, the luxI promoter regulates production of autoinducer (AHL), which binds LuxR and enables it to transcriptionally activate the promoter.

Negative feedback arises from cell death that is triggered by a bacteriophage lysis gene (φ X174 E) that is also under control of the luxI promoter (Prindle, A. et al. A sensing array of radically coupled genetic 'biopixels'. *Nature* 481, 39-44, 2012; Young, K. D. & Young, R. Lytic action of cloned φ X174 gene E. Journal of virology 44, 993-1002, 1982; Marguet, P., Tanouchi, Y., Spitz, E., Smith, C. & You, L. Oscillations by minimal bacterial suicide circuits reveal hidden facets of host-circuit physiology. *PloS One* 5, e11909, 2010). Importantly, AHL can diffuse to neighboring cells and thus provides an intercellular synchronization mechanism.

Figure 21A:
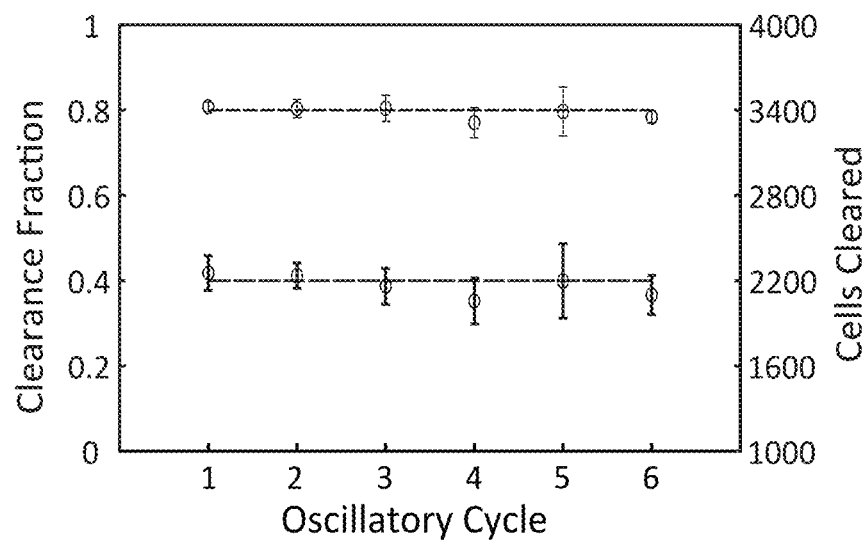
FIG. 21. Various properties of the SLC. (A) The fraction and number of bacterial cells cleared per consecutive oscillatory cycle in the growth chamber for a typical microfluidic experiment for *S. typhimurium*, including the effects of lysis and flow of cells outside of the trap (Strain 1). Top line: clearance fraction; Bottom line; Cells cleared. (B) Subset of time series images from the experiment in (A) showing a portion of the growth chamber where survivors of the initial lysis event (160 min frame, enclosed portion) produce progeny (250 min frame, enclosed portion) which are lysis sensitive. (C) Period as a function of the environmental temperature for *E. coli* (Strain 13). The circuit does not oscillate for temperatures above 37° C. in *E. coli*. Error bars indicate ±1 standard deviation for 12-19 peaks. (D) Colony amplitude at quorum firing for increasing degradation on the LuxI activator protein in the computational model. These results are confirmed by batch well-plate experiments of the LuxI ssrA (solid line, Strain 2) and non-ssrA (dashed line, Strain 1) tagged versions of the circuit in *S. typhimurium* (inset).
Figure 21B:
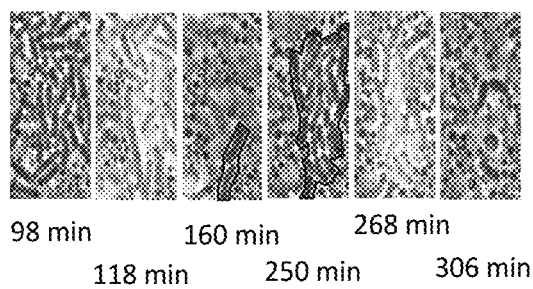

The bacterial population dynamics arising from the synchronized lysis circuit can be conceptualized as a slow buildup of the signaling molecule (AHL) to a threshold level, followed by a lysis event that rapidly prunes the population and enables the release of bacterial contents (FIG. 1B). After lysis, a small number of remaining bacteria begin to produce AHL anew, allowing the "integrate and fire" process to be repeated in a cyclical fashion. We used microfluidic devices to observe growth, lysis, and protein release with sfGFP as a proxy for circuit dynamics and therapeutic expression in attenuated *S. typhimurium*. We observed periodic lysis events characterized by peaks in the fluorescent reporter profile that correspond to population lysis (FIG. 1C). Surviving cells after each cycle produce lysis-sensitive progeny such that the fraction of lysed cells remains consistent throughout cycles, suggesting that lysis and survival occur in a stochastic manner (FIG. 21A-B). Given the ultimate goal of implementation in a fluctuating in vivo microenvironment, we tested a range of incubation temperatures (36° C. to 40° C.) and perfusion rates (100 µm/s to 200 µm/s), measuring an average period of 3 hours across all conditions in our microfluidic devices (FIG. 1D). The results of these experiments are further summarized in the discussion of Supplementary Videos 1, 2, and 3 provided herein. These findings suggest that the SLC has the capacity to generate robust cycles of lysis and release in the face of related environmental perturbations likely to be encountered in the in vivo context.

Figure 18A:
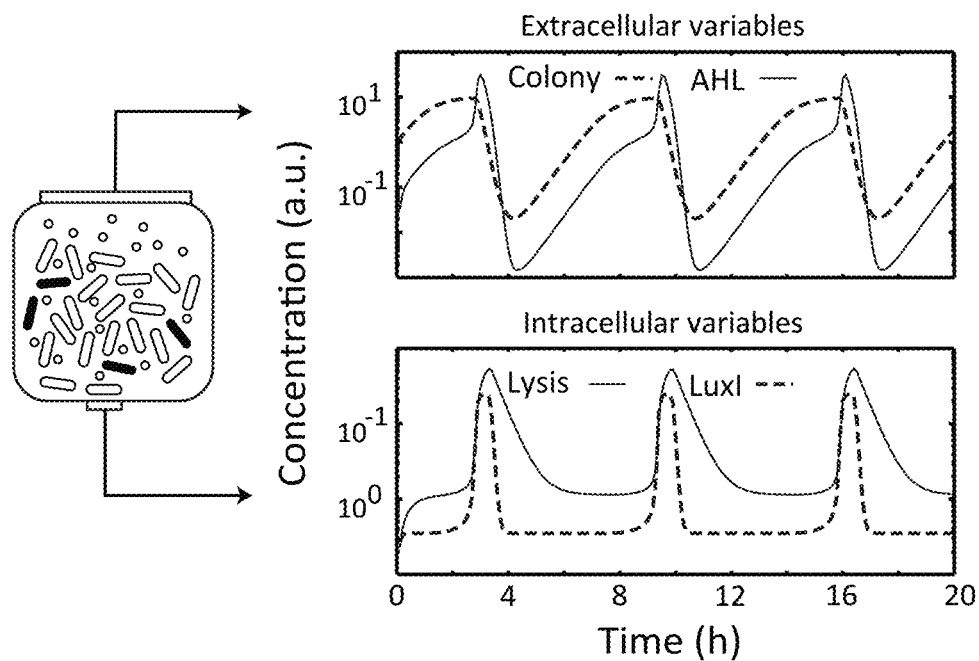
FIG. 18. Computational modeling and tunability. (A) The model consists of intracellular variables (lysis gene E and LuxI) and extracellular variables (colony size and AHL). A time series of colony size (top panel, dashed line), colony AHL (top panel, solid line), intracellular LuxI (bottom panel, dashed line) and lysis protein (bottom panel, solid line) are shown on the right. (B) The region in the model parameter space for clpXP mediated degradation, as a proxy for temperature (Purcell, O., Grierson, C. S., Bernardo, M. & Savery, N. J. Temperature dependence of ssrA-tag mediated protein degradation. *Journal of Biological Engineering* 6, 10, 2012) and flow where the model output is oscillatory increases with higher production and degradation terms. (C) Results from the computational model showing the ability to tune the oscillatory period by varying ClpXP mediated degradation of LuxI. (D) Fluorescence profiles showing lysis oscillations for LuxI ssrA (closed circles, Strain 2) and non-ssrA (open circles, Strain 1) tagged versions of the circuit. See Supplementary Information for complete model information.
Figure 18B:
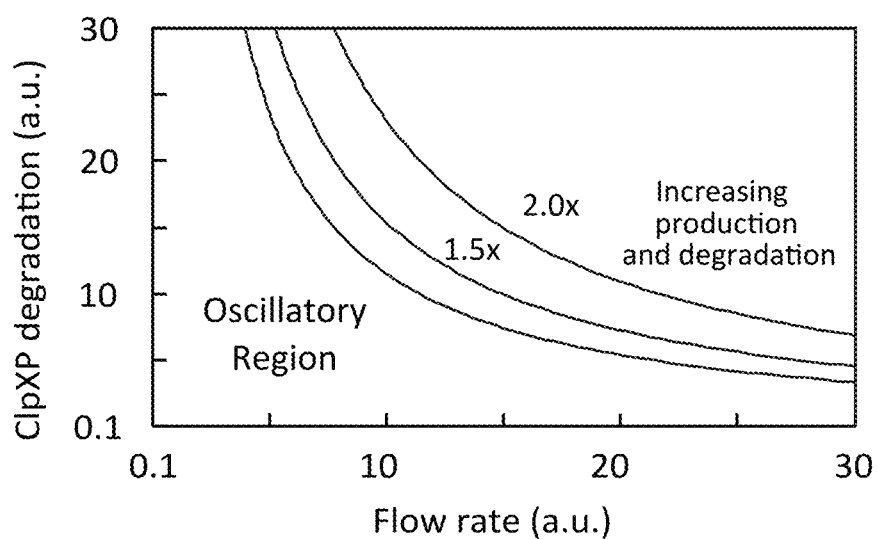
Figure 21C:
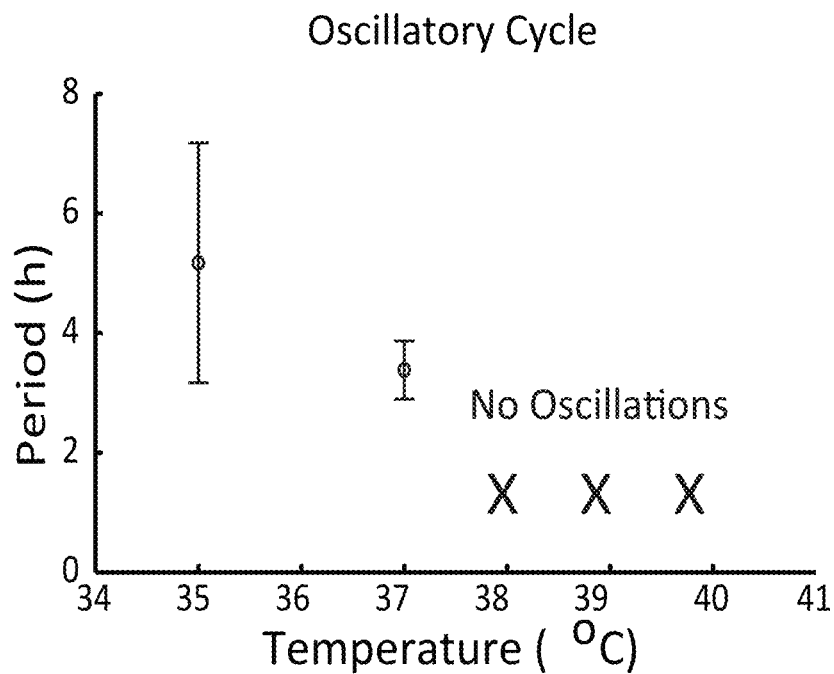

The emergence of bacterial therapies in synthetic biology has accentuated the need for predictive modeling. This need stems from a bottleneck created by a difference in the timescales for bacterial cloning versus animal experiments: therapies can be created much faster than they can be tested in vivo. Therefore, in order to quantitatively characterize the SLC circuit before testing in animal models, we first developed a computational model to explore the parameters affecting robustness and tunability (FIG. 18A). We observed that high production and degradation rates resulted in a wider domain of oscillatory dynamics in the parameter space (FIG. 18B). This model is consistent with our observations that oscillations in *S. typhimurium* were more robust than in *E. coli*, where rates of protein production and degradation were previously found to be lower (Prindle, A. et al. Genetic circuits in *Salmonella typhimurium*. *ACS Synthetic Biology* 1, 458-464, 2012), (FIG. 21C).

Figure 18C:
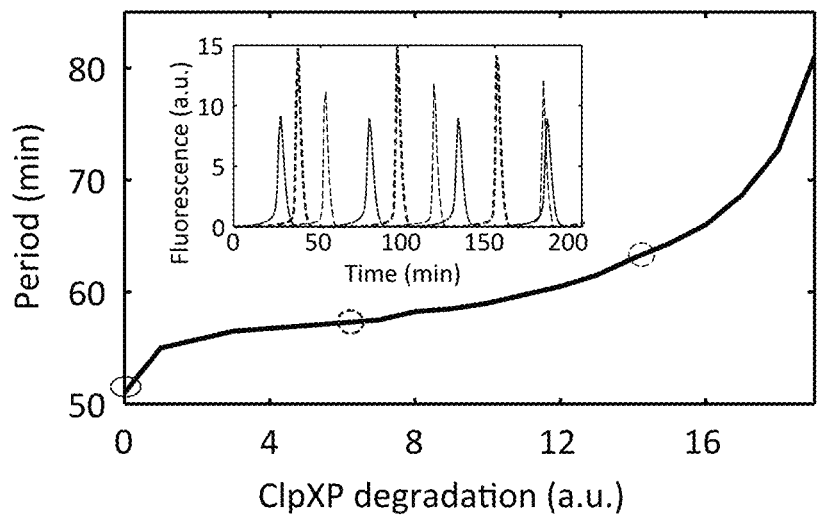
Figure 18D:
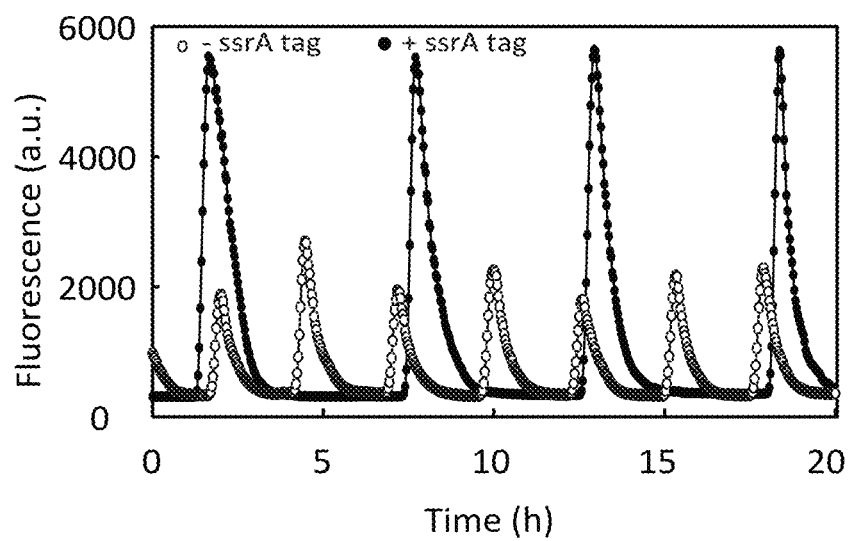
Figure 19A:
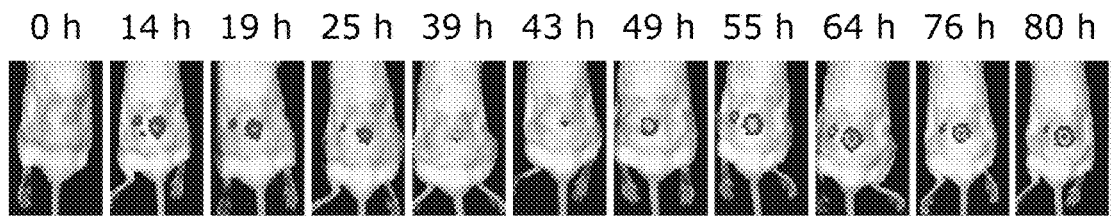
FIG. 19. In vivo bacterial dynamics. (A) IVIS imaging over time of a mouse bearing two hind flank tumors injected once with a stabilized SLC-hly strain (Strain 8, synchronized lysis and therapy). (B) The relative luminescence profiles (relative to luminescence at 0 h) of the left (solid line) and right (dashed line) tumors from the images in (A). (C) Single tumor density map trajectories of bacterial luminescence for the SLC-hly strain. (D) A relative luminescence profile from a genomically integrated constitutively luminescent strain (Strain 9). Intratumoral injection resulted in over 35-fold higher post-injection luminescence compared to intravenous injection (FIG. 23D). Respective values of the line trajectory in (B) and (D) are shown as density maps above the plots. (E) Single tumor density map trajectories of bacterial luminescence for the constitutive strain. Data for each axis represents separate experiments. (F) Average relative body weight over time for subcutaneous tumor-bearing mice with a single intravenous injection of the with the SLC+constitutive hlyE (solid line, n=9 mice, Strain 11), a non-SLC strain with constitutive hlyE (dotted line line, n=5 mice, Strain 12), or the no-plasmid control strain (dashed line, n=9 mice, Strain 7) (***P<0.001, two-way ANOVA with Bonferroni post test, s.e.). (G) Average relative body weight over time for mice with subcutaneous tumors injected with the SLC-3 strains (solid line, Strain 10, 14, and 15) and the no-plasmid control (dashed line, Strain 7). Bacteria were injected intratumorally on days 0, 2, 6, and 10 (black arrows) (n=10 mice for both cases, s.e.).
Figure 19B:
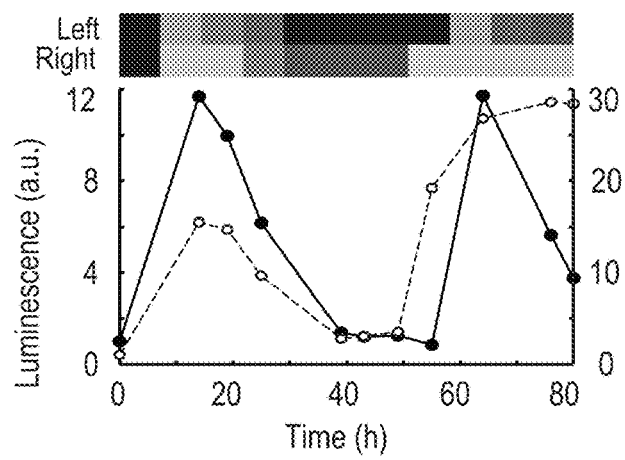
Figure 19C:
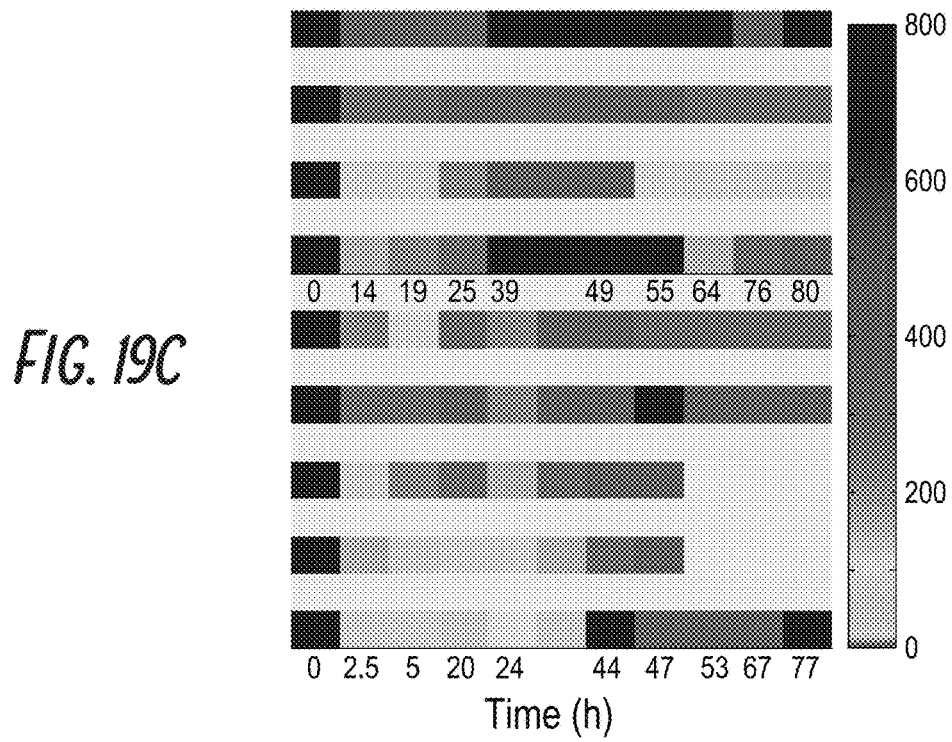
Figure 19D:
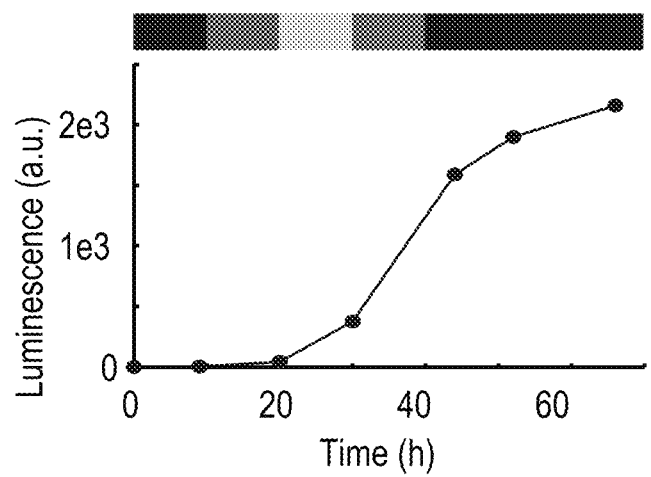
Figure 19E:
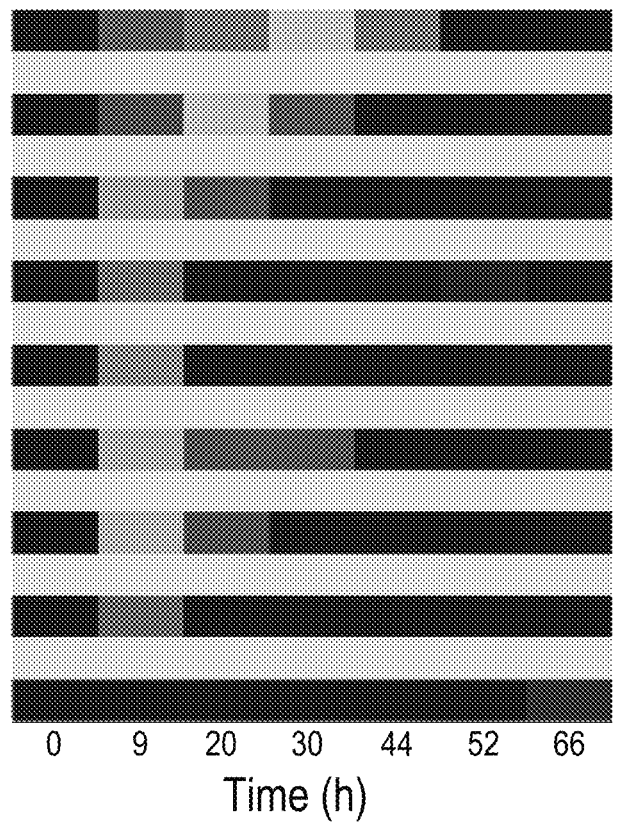
Figure 19F:
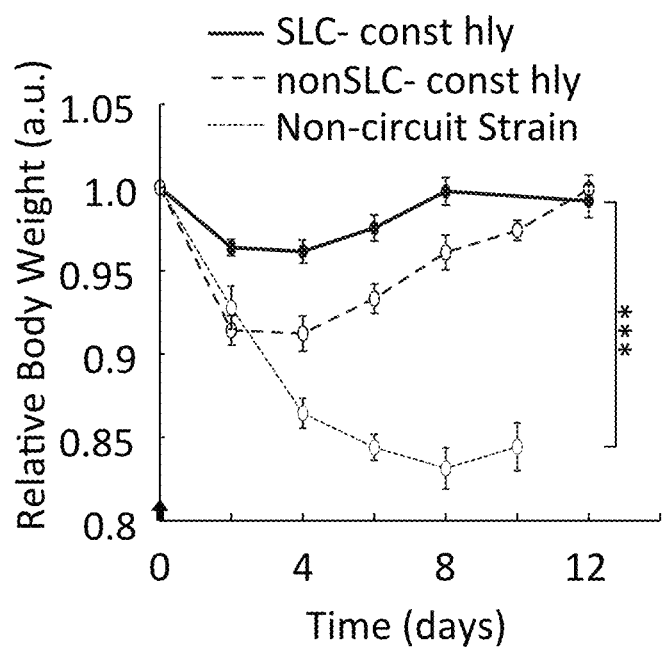
Figure 19G:
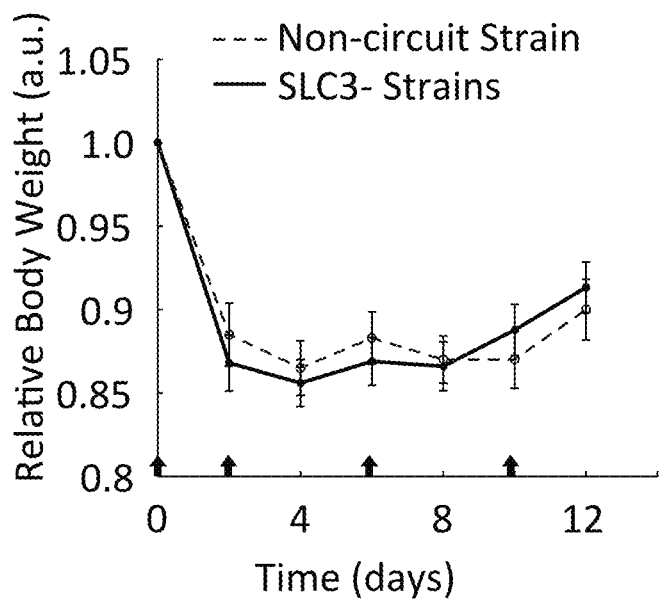
Figure 21D:
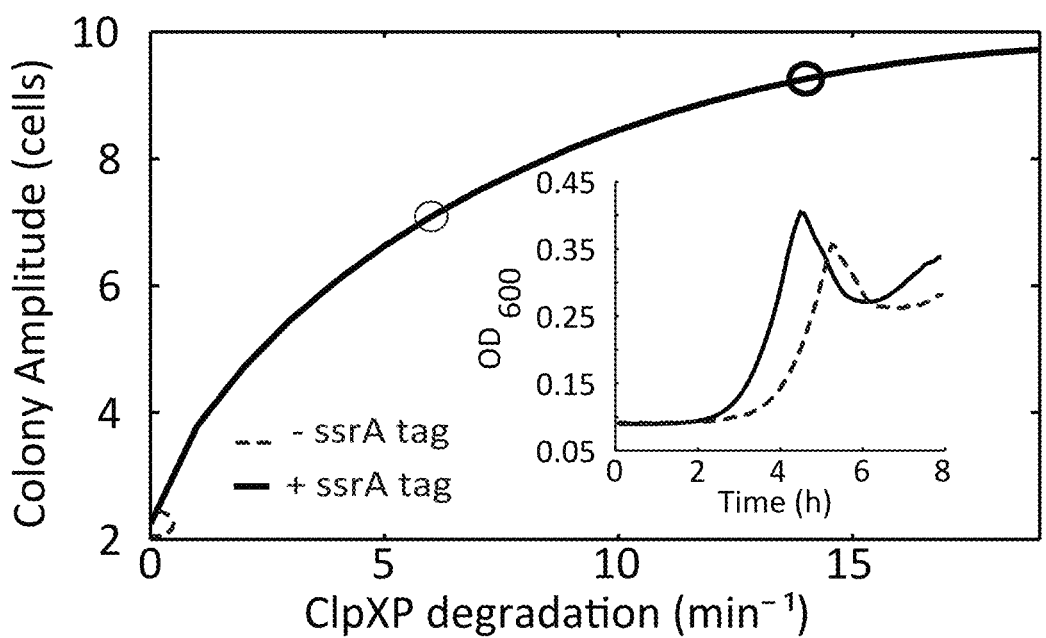

Since the ability to manipulate circuit behavior greatly enhances the versatility to apply our system in different contexts, we explored the tunability of the lysis period by adding an ssrA degradation tagging sequence on the LuxI protein. Consistent with model predictions, we observed an increased period and colony firing amplitude experimentally (FIGS. 18C-D and FIG. 21D). The SLC thus enables tuning of the drug delivery period and magnitude.

Figure 22D:
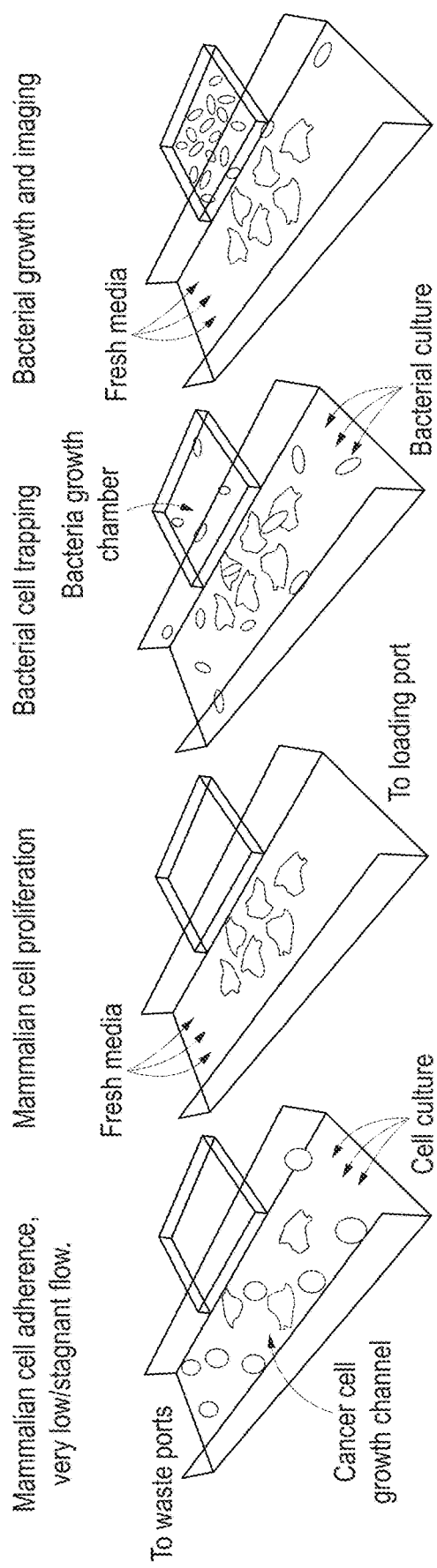

To incorporate therapeutic functionality into the SLC, we added expression of Hemolysin E, or hlyE of *E. coli*, which has been tested as a pore-forming anti-tumor toxin (Ryan, R. et al. Bacterial delivery of a novel cytolysin to hypoxic areas of solid tumors. *Gene Therapy* 16, 329-339, 2009; Nguyen, V. H. et al. Genetically engineered *Salmonella typhimurium* as an imageable therapeutic probe for cancer. *Cancer Research* 70, 18-23, 2010). In order to visualize bacterial lysis and killing of cancer cells in vitro, we engineered a microfluidic device so that cancer cells adhere inside a growth channel flanked by smaller bacterial growth chambers, which permits single-cell visualization of bacterial lysis and cancer cell death (FIG. 22D). After co-culturing human cervical cancer HeLa cells with *S. typhimurium* harboring the SLC circuit, we observed HeLa cell death upon the onset of bacterial lysis, indicating efficient toxin release (FIG. 3A-B). The results of these experiments are further summarized in the discussion of Supplementary Videos 5 and 6 provided herein. Complete cell death outside the trap occurred within ~111 min of initial sfGFP fluorescence (FIG. 3C). Thus, the SLC was capable of releasing HlyE at levels necessary to kill cancer cells in vitro.

To verify the mechanism of therapeutic activity, we assessed the toxicity of released bacterial contents in batch culture. As anticipated, we found that HeLa cells exposed to supernatant from a culture of the SLC with the hlyE module exhibited almost complete loss of viability (FIG. 3D), while HeLa cells exposed to supernatants of the SLC without the hlyE module exhibited only a slight loss (~15%) of viability. We concluded that bacterial lysis allowed for efficient HlyE release in vitro and that natural intracellular bacterial contents do not significantly affect HeLa cell viability. We further investigated the drug delivery characteristics of the SLC with hlyE by seeding variable amounts of circuit-harboring bacteria with HeLa cultures in well plates. We observed that the timing to HeLa cell death from initial seeding increased with lower bacterial seeding volumes, presumably resulting from the extended time needed for bacteria to reach the quorum threshold (FIG. 3E). The results of these experiments are further pictorially summarized in Supplementary Video 6, which depicts bacteria and cancer cell co-culture on a microfluidic device at 60× magnification. This video shows that Strain 3 (non-motile *S. typhimurium*, SDC with HlyE) was loaded in the growth chambers while HeLa cells grew in the main channel of the device. Bacteria could be seen growing in their chamber until they reached a quorum threshold and lysed. Upon lysis, the HeLa cells in the channel could be seen undergoing cell death. Timelapse fluorescence microscopy images were taken every 3 min. Increased firing rates corresponded to shorter exposure times to HlyE until cell death, indicating increased lysis and therapeutic release, although the exposure magnitude needed in all cases appears to be similar (FIG. 3F). In this way, the initial population level of seeded bacteria determines the initial timing and release characteristics of the circuit.

We subsequently used a luciferase reporter to monitor bacterial population dynamics in grafted syngeneic colorectal tumors in mice. To minimize the extent of plasmid loss in the absence of antibiotic selection in vivo, we incorporated previously described stabilizing elements for plasmid retention and segregation into the SLC (Gerdes, K. The parB (hok/sok) locus of plasmid R1: a general purpose plasmid stabilization system. *Nature Biotechnology* 6, 1402-1405, 1988; Wood, T., Kuhn, R. & Peretti, S. Enhanced plasmid stability through post-segregational killing of plasmid-free cells. *Biotechnology Techniques* 4, 39-44, 1990; Derman, A. I. et al. Phylogenetic analysis identifies many uncharacterized actin-like proteins (alps) in bacteria: regulated polymerization, dynamic instability and treadmilling in alp7a. *Molecular Microbiology* 73, 534-552, 2009; Danino, T., Lo, J., Prindle, A., Hasty, J. & Bhatia, S. N. In vivo gene expression dynamics of tumor-targeted bacteria. *ACS Synthetic Biology* 1, 465-470, 2012; Danino, T. et al. Programmable probiotics for detection of cancer in urine. *Science translational medicine* 7, 289ra84-289ra84; 2015). Additionally, we placed both the therapeutic and luxCDABE genes (the in vivo reporter module) under the luxI promoter as an indicator of hlyE production and quorum firing via bacterial luminescence (FIG. 1A). Using a subcutaneous model of colorectal cancer (MC26 cell line) in immunocompetent mice, we intratumorally injected a strain of SLC bacteria (SLC-hly). Using In-Vivo Imaging (IVIS) technology (Danino, T., Prindle, A., Hasty, J. & Bhatia, S. Measuring growth and gene expression dynamics of tumor-targeted *S. typhimurium* bacteria. JoVE, *Journal of Visualized Experiments*, e50540-e50540, 2013), we observed pulsatile bacterial population dynamics within the tumor (FIG. 19A-C, FIG. 23A), consistent with the design and in vitro characterization. The magnitude of luminescence intensity was on average ~300-fold lower than the constitutive control strain, indicating a significant decrease in bacterial population levels within the tumor (FIG. 23C). These results demonstrate the successful engineering of bacterial population dynamics for in vivo applications.

Figure 20A:
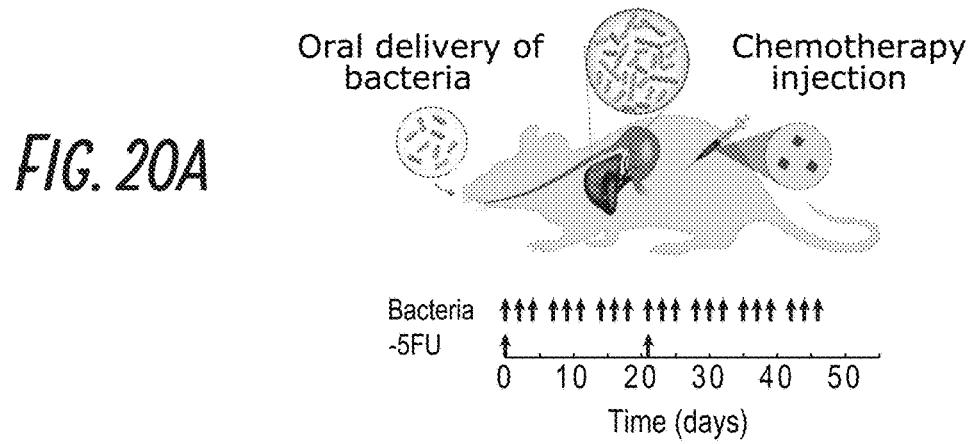
FIG. 20. In vivo therapy. (A) Schematic of the experimental syngeneic transplantation model of hepatic colorectal metastases in a mouse, with the dosing schedule of either bacteria or chemotherapy (5-FU). The bacteria were delivered orally while 5-FU was delivered via intraperitoneal injection. (B) Relative body weight over time for the mice with hepatic colorectal metastases fed with the SLC-3 strains (thick solid line), injected with 5-FU chemotherapy (thin solid line), or in combination (dashed line). Error bars indicate ±1 standard error for 5-7 mice. (C) Median relative tumor activity measured via tumor cell luminescence using IVIS imaging, for the chemotherapy and engineered bacterial therapy cases from (B). (D) Median relative tumor activity for the combination therapy case from (B). Error bars for (C) and (D) indicate the interquartile ranges for 5-7 mice. The dashed line marks relative tumor activity of 0.70. (E) Fraction of mice from the cases in (B) which respond with 30% reduction of tumor activity over time. (F) Fraction survival over time for the mice in (B) (**P<0.01, log rank test; n=5-7 mice).
Figure 20B:
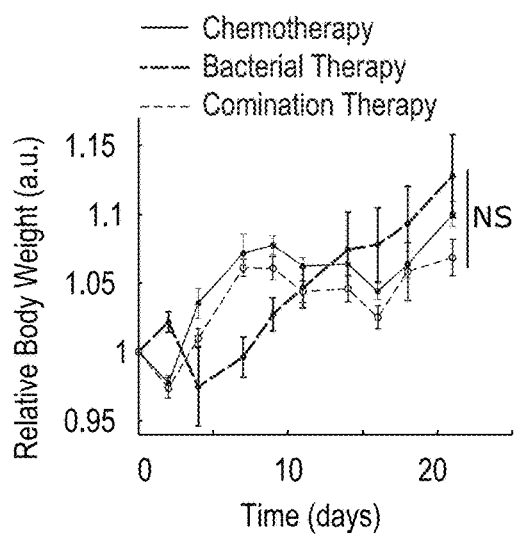
Figure 20C:
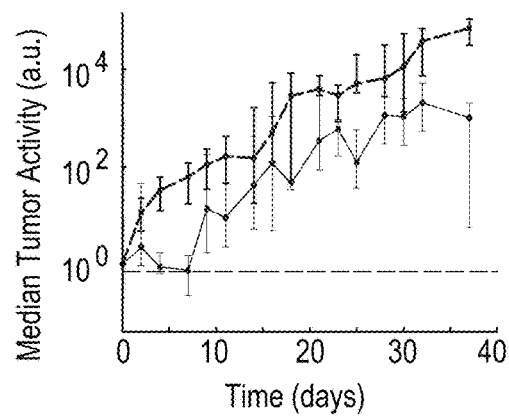
Figure 20D:
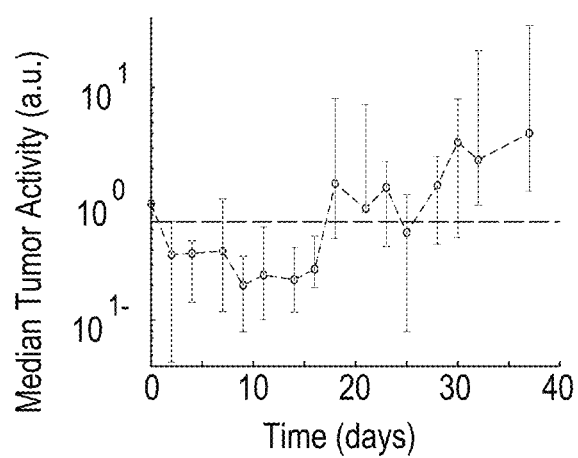
Figure 20E:
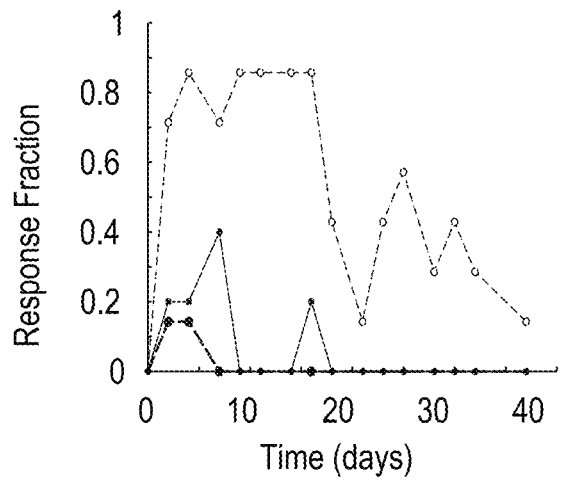
Figure 20F:
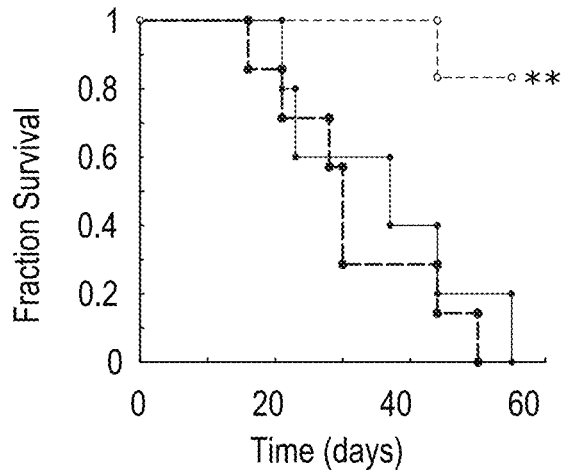
Figure 23E:
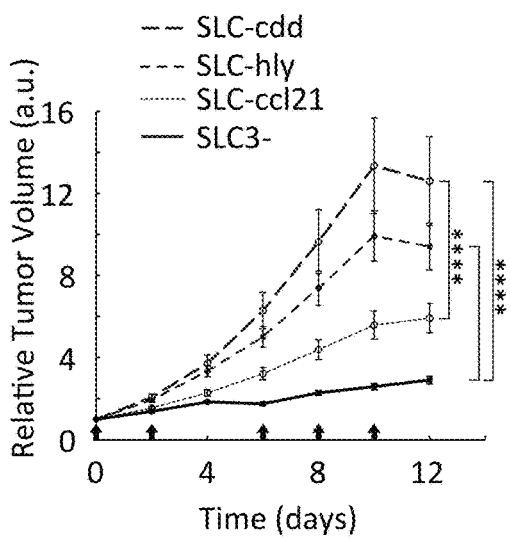
FIG. 23. In vivo expression and therapy testing. (A) End-point in vitro luminescence intensity for attenuated SLC strains after ~20 h of growth. Host strains A and B are the host bacteria for Strains 8 and 10. They are ELH1301 and ELH 430, respectively (Hohmann, E. L., Oletta, C. A. & Miller, S. I. Evaluation of a phop/phoq-deleted, aroa-deleted live oral *Salmonella typhi* vaccine strain in human volunteers. *Vaccine* 14, 19-24, 1996). Host A exhibits ~2-fold higher luminescence with the same circuit than Host B. (B) IVIS imaging over time of a mouse bearing subcutaneous tumors injected with a genomically integrated constitutively luminescent strain (Strain 9). (C) End-point in vivo bacterial luminescence of the SLC strain (lysis +) and the constitutive strain (lysis −) from the experiments presented in FIG. 19. Error bars represent the standard error of the mean bacterial luminescence from 9 tumors. (D) Post-injection in vivo bacterial luminescence for the constitutive strain administered intravenously (vein) or intratumorally (tumor). Luminescence was measured ~20 h post-injection. Error bars represent the standard error of the mean bacterial luminescence from 6 and 9 tumors for the intravenous and intratumoral cases, respectively. (E) Average relative tumor volume over time for subcutaneous tumor bearing mice injected with SLC-hly (thin dashed line, Strain 10), SLC-cdd (thick dashed line, Strain 14), SLC-ccl21 (dotted line, Strain 15), and all together (SLC-3) (solid line). Bacteria were injected intratumorally on days 0, 2, 6, 8, and 10 (black arrows) (**P<0.0001, two-way ANOVA with Bonferroni post test, n=14-17 tumors, s.e.). (F) Average relative tumor volume over time for mice with subcutaneous tumors injected with the SLC-3 strains (solid line, Strain 10, 14, and 15) and the no-plasmid control (dashed line, Strain 7). Bacteria were injected intratumorally on days 0, 2, 6, and 10 (black arrows) (**$P<0.0001$, two-way ANOVA with Bonferroni post test, n=18-19 tumors, s.e.). (G) Average relative tumor volume over time for subcutaneous tumor bearing mice injected with the no-plasmid bacterium (Strain 7), 5-FU chemotherapy, the SLC-3 strains, and the combination of SLC-3 with chemotherapy. Bacteria were injected intratumorally on days 0, 4, and 7 (black arrows), and chemotherapy was administered on days 2 and 9 (white arrows) (*$P<0.05$, ****$P<0.0001$, two-way ANOVA with Bonferroni post test, n=12-16 tumors, s.e.). (H) Fraction of mice from the cases in (G) which respond with 30\% reduction of tumor volume over time. (I) Average relative tumor volume over time and (inset) fraction of subcutaneous tumor bearing mice with a single intravenous injection of SLC-hly which respond with 30\% reduction in tumor volume over time (n=17-22 tumors, s.e.). (J) Fraction survival over time for mice with hepatic colorectal metastases fed with either the SLC-3 strains (dotted line) or the no-plasmid control (solid line) (*$P<0.05$, log rank test; n=11-12 mice).
Figure 23F:
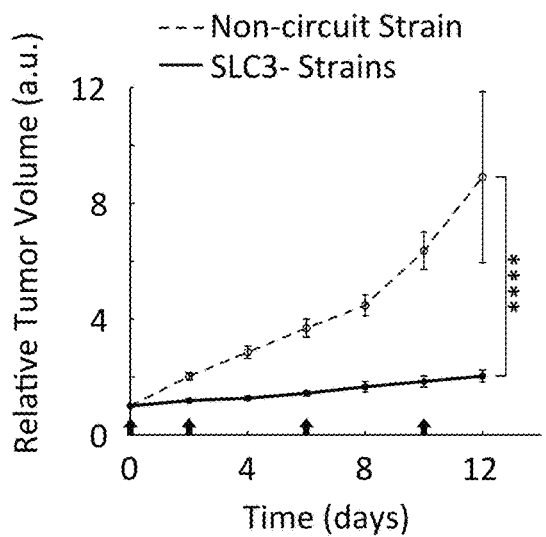
Figure 23G:
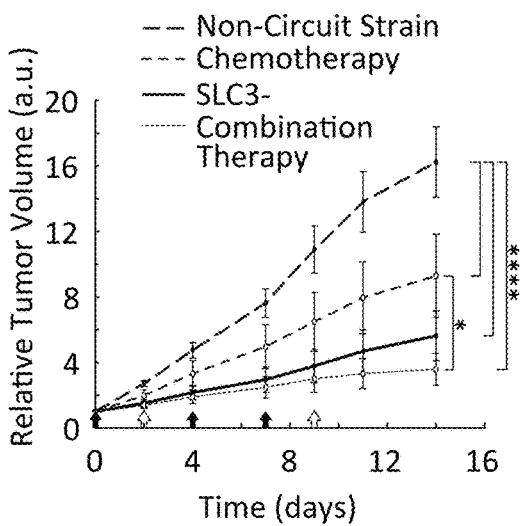
Figure 23H:
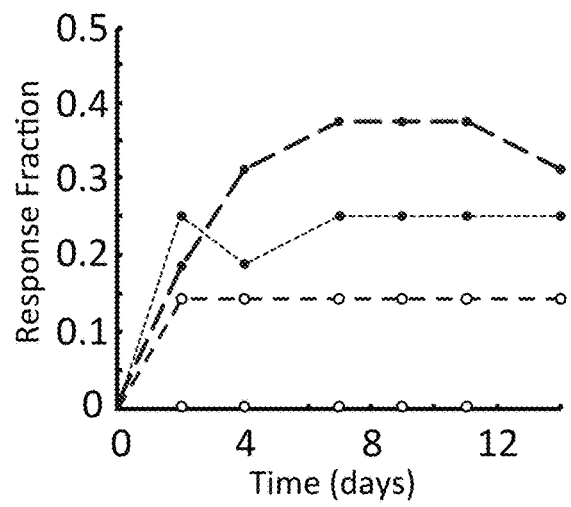
Figure 23I:
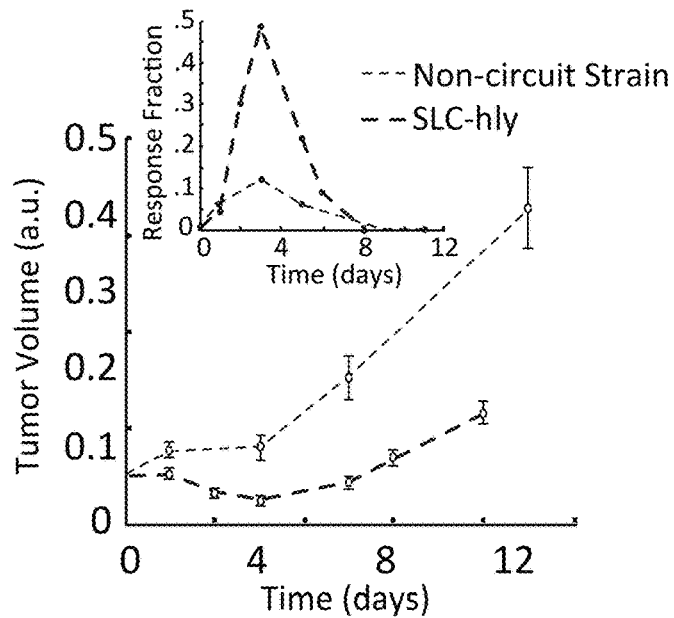
Figure 23J:
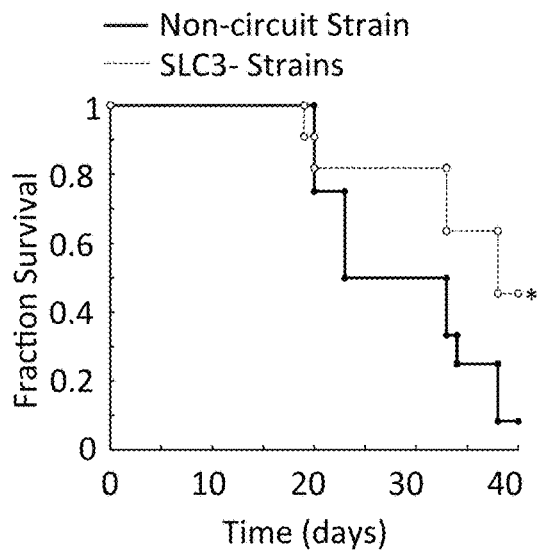
Figure 24:
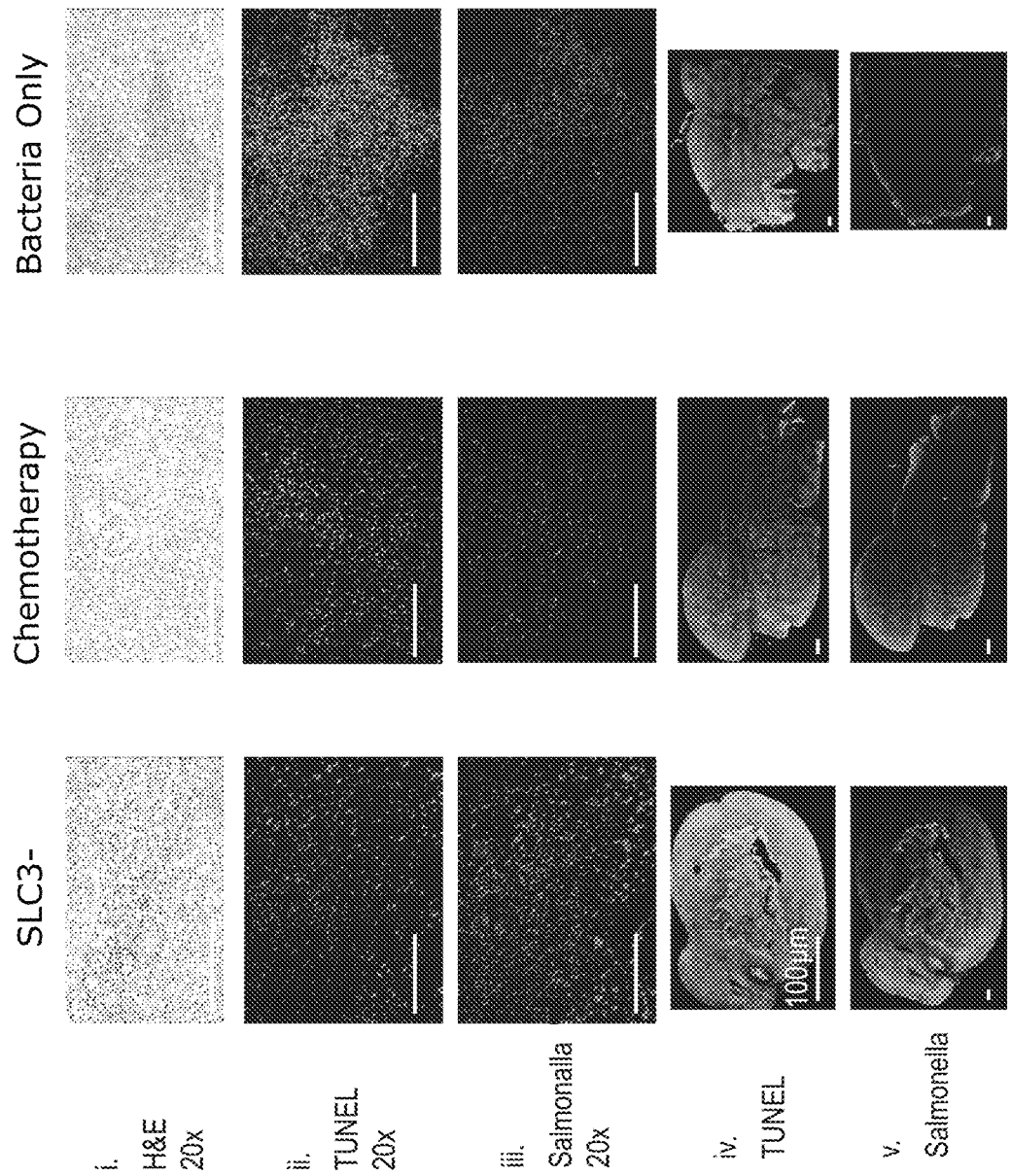
FIG. 24. (A) Histology of tumor sections taken from mice with different treatments 3 days post administration: (i) H and E staining for tissue sections intravenously injected with a combination of therapeutic bacteria (SLC-3), chemotherapy (5-FU), or a bacteria control with no therapeutic (Strain 7). (ii) TUNEL staining in the same sections indicating cell apoptosis. (iii) *Salmonella* immunohistochemistry in the same sections confirming presence of bacteria in tumors. Scale bars for (i), (ii), and (iii) denote 50 μm. (iv) and (v) TUNEL and *Salmonella* staining in the entire tumor sections. Scale bars for (iv) and (v) denote 100μ m. DAPI staining was used to obtain a measure of live and dead cells in (ii)-(iv). Histology slices (n=6) from 20× images were compared across the groups and mean intensity of TUNEL staining, normalized by sample area, was demonstrated to be significantly higher for SLC-3 compared to the other two groups ($P<0.0001$, one-way ANOVA), and not significantly different between the chemotherapy and bacteria only cases. Additionally, we observed bacterial colonization of the tumors as well as significantly higher cell death in the tissue for the SLC-3 sample.
Figure 25A:
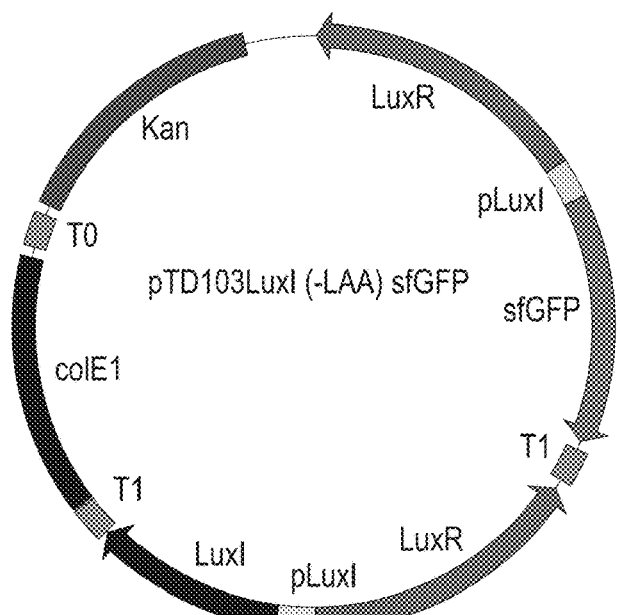
FIG. 25A-I. Graphical representations of some of the plasmids used in this study (see additional information described herein for more details).
Figure 25B:
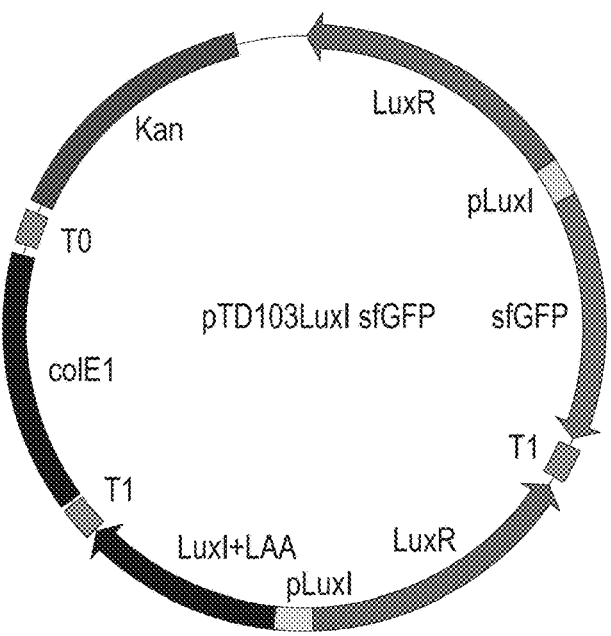
Figure 25C:
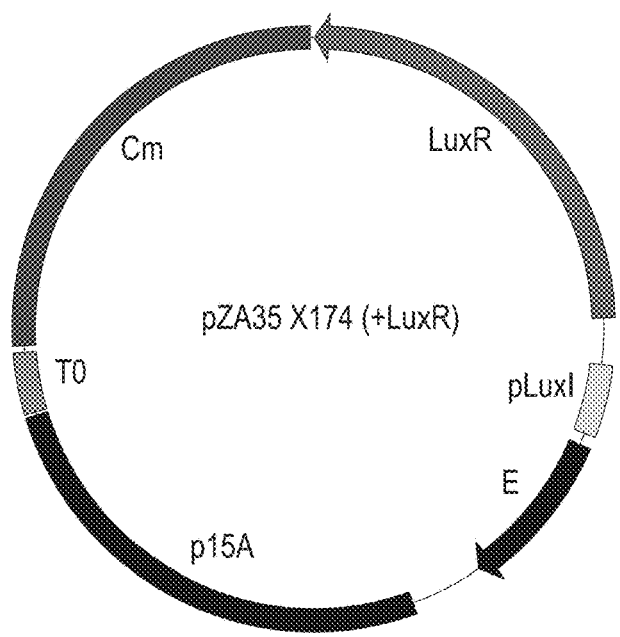
Figure 25D:
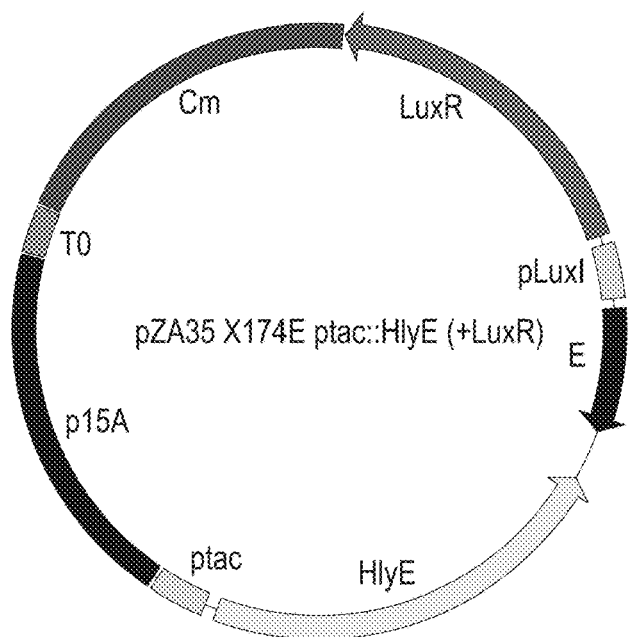
Figure 25E:
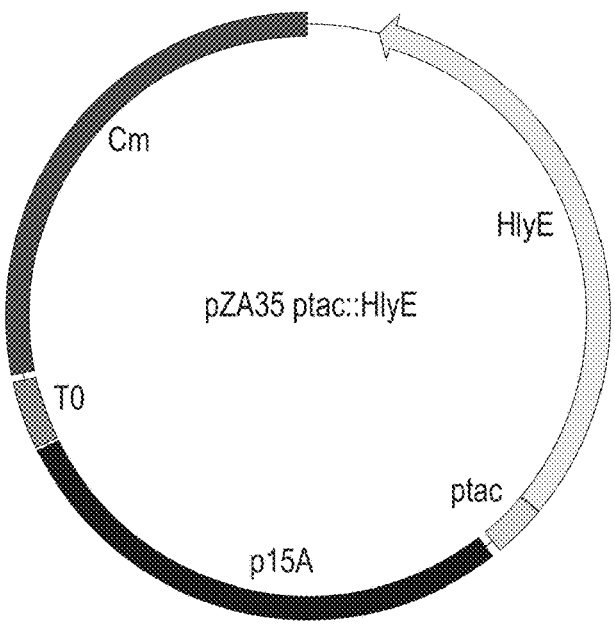
Figure 25F:
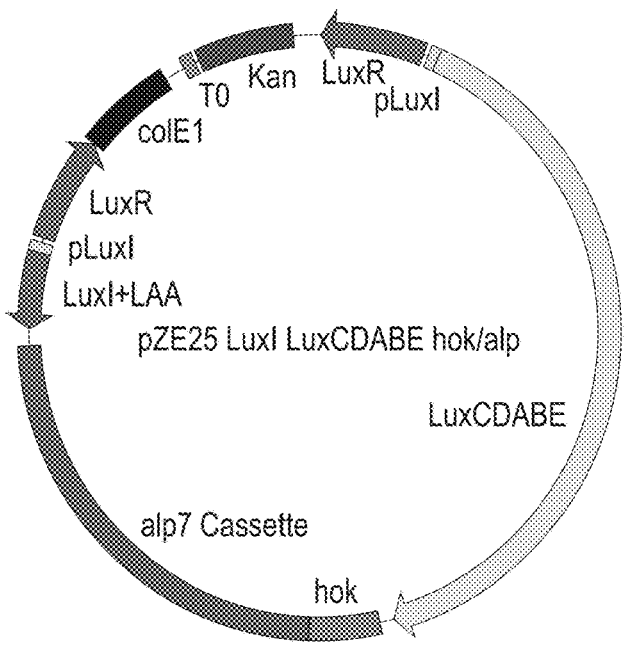
Figure 25G:
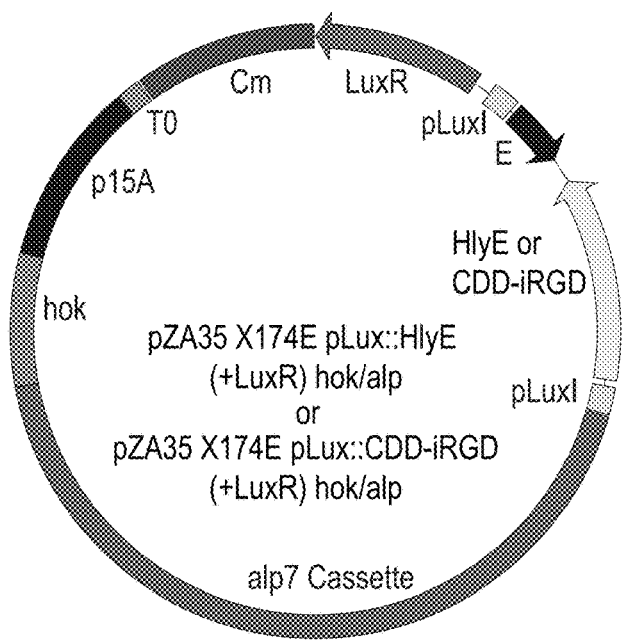
Figure 25H:
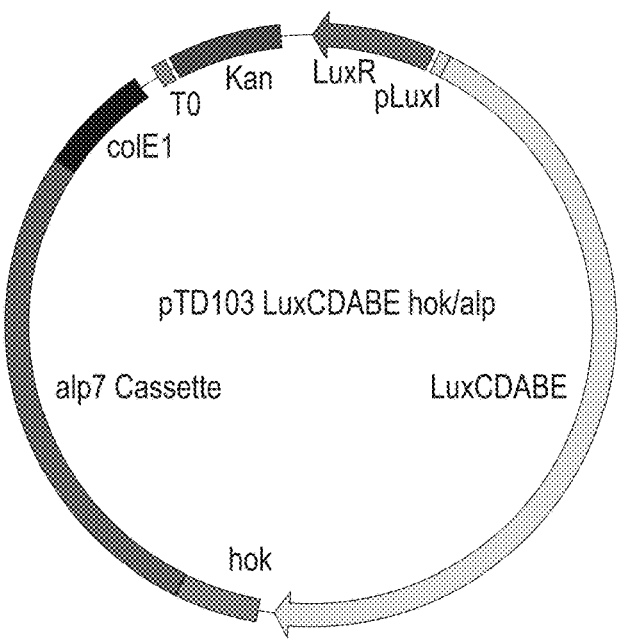
Figure 25I:
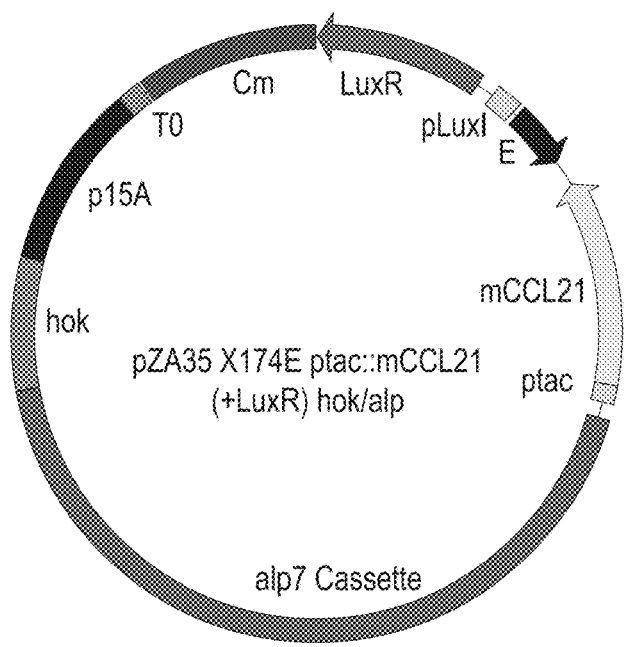

As a preliminary step towards understanding the health effects of the circuit on mice, we compared the in vivo effects of two strains constitutively producing HlyE with a single injection directly into the bloodstream of mice with established subcutaneous tumors. One strain contained the full synchronized lysis circuit (SLC-const hly), and the other did not contain LuxI mediated positive feedback for synchronized lysis (nonSLC-const hly). We observed a significant decrease in mouse health for the non-SLC therapeutic producing strain compared to the SLC and non-circuit control strain (FIG. 23E). We then leveraged the versatility of the SLC system to create two additional therapeutic strains that activate a host immune response (via T-cell and dendritic cell recruitment, using CCL-21) and trigger tumor cell apoptosis (using CDD-iRGD), respectively (Chen, R. et al. Application of a pro-apoptotic peptide to intratumorally spreading cancer therapy. *Cancer Research* 73, 1352-1361, 2013; Loeffler, M., Le'Negrate, G., Krajewska, M. & Reed, J. C. *Salmonella typhimurium* engineered to produce CCL21 inhibit tumor growth. *Cancer Immunology, Immunotherapy* 58, 769-775, 2009) (FIG. 23). We found that repeated injections delivered directly to the tumor do not result in significant weight differences between the multiple SLC-3 strains and the control, where mice treated with the SLC-3 strains exhibited a significant therapeutic effect (FIG. 23F-G). Additionally, we examined histology of tumor sections taken from mice treated with the SLC-3 strains, chemotherapy, or non-circuit bacteria. We observed bacterial colonization of the tumors as well as significantly higher cell death in the tissue for the SLC-3 case (FIG. 24). Taken together, these results indicate that the circuit confers enhanced safety for mice injected intravenously, as well as increased cell death within the tumor. To establish a proof-of-principle for the application of our circuit in the context of cancer therapy, we took inspiration from previous studies which have shown that anaerobic bacteria can occupy avascular tumor compartments where chemotherapy is thought to be ineffective due to a lack of oxygen (Dang, L. H., Bettegowda, C., Huso, D. L., Kinzler, K. W. & Vogelstein, B. Combination bacteriolytic therapy for the treatment of experimental tumors. *Proceedings of the National Academy of Sciences* 98, 15155-15160, 2001). It has been proposed that an optimal therapeutic approach may involve a synergistic combination, whereby bacteria deliver drugs in the necrotic core of a tumor while standard chemotherapy is used for the vascularized regions (Dang, L. H., Bettegowda, C., Huso, D. L., Kinzler, K. W. & Vogelstein, B. Combination bacteriolytic therapy for the treatment of experimental tumors. *Proceedings of the National Academy of Sciences* 98, 15155-15160, 2001; Forbes, N. S. Engineering the perfect (bacterial) cancer therapy. *Nature Reviews Cancer* 10, 785-794, 2010). Guided by this paradigm, we tested a combination of SLC bacteria and a common chemotherapy (5-fluorouracil, or simply 5-FU) in an experimental syngeneic transplantation model of hepatic colorectal metastases. We observed that oral delivery of the bacterial strains led to safe and efficient colonization of established liver tumors, delivered 5-7 days post-transplantation, thus permitting repeated dosing without adverse effect on the mice (FIG. 20A-B). In response to repeated oral delivery of the bacterial therapy alone or administration of chemotherapy alone on Days 0 and 21, tumors exhibited similar activity trajectories (FIG. 20C). However, a combination of the two therapies led to a marked decrease in tumor activity over a period of 18 days (FIG. 20D). During this initial 18-day period, a large fraction of the tumors qualified as eliciting at least a 30% reduction in tumor size (FIG. 20E). The overall response led to roughly a 50% increase in the survival time for animals harboring incurable colorectal metastases (FIG. 20F).

Improvements may arise from strategies for long term circuit stability or the utilization of additional therapeutic cargo.

The synchronized lysis circuit directly addresses the problem of systemic inflammatory response with programmed population control; since the bacterial colony is pruned after each oscillatory lysis event, the design has the potential to mitigate an undesirable host response. In contrast to most nanotech strategies, the approach does not require pre-loading of a drug or the repeated introduction of the delivery vehicle, and cellular lysis eliminates the need for additional secretion machinery. Cyclic drug release may have broader implications, given recent insights into the effects of circadian rhythms on host-microbial interactions and metabolic disorders (Leone, V. et al. Effects of diurnal variation of gut microbes and high-fat feeding on host circadian clock function and metabolism. *Cell Host & Microbe* 17, 681-689, 2015; Thaiss, C. A., Levy, M. & Elinav, E. Chronobiomics: The biological clock as a new principle in host-microbial interactions. *PLoS Pathog* 11, e1005113, 2015). More generally, the synchronized lysis circuit exemplifies a methodology for leveraging the tools of synthetic biology to fully exploit the natural propensity for certain bacteria to colonize solid tumors. Such engineering strategies may allow for the development of therapeutic communities in the tumor environment, where population dynamics are driven by interacting viruses, bacteria, and host cells (such as T-cells) (Cheong, I. et al. A bacterial protein enhances the release and efficacy of liposomal cancer drugs. *Science* 314, 1308-1311, 2006).

Methods Summary

Strains and Plasmids

Some circuit strains described in the present disclosure were cultured in LB media with 50 µg ml$^{-1}$ and 34 µg ml$^{-1}$ of Kanamycin and Chloramphenicol respectively, along with 0.2% glucose, in a 37° C. incubator. Mammalian cells were cultured in DMEM media supplemented with 10% fetal bovine serum and 1% penicillin/streptomycin (CellGro 30-002-CI), placed inside a tissue culture incubator at 37° C. maintained at 5% $CO_2$. Plasmids were constructed using the CPEC method of cloning or using standard restriction digest/ligation cloning (Quan, J. & Tian, J. Circular polymerase extension cloning of complex gene libraries and pathways. *PloS One* 4, e6441 (2009). The activator plasmid (Kan, ColE1) was used in previous work from our group, while the lysis plasmid was constructed by taking the lysis gene, E, from the ePop plasmid via PCR and cloning it into a vector (Chlor, p15A) under the control of the LuxI promoter (Prindle, A. et al. A sensing array of radically coupled genetic 'biopixels'. *Nature* 481, 39-44, 2012; Marguet, P., Tanouchi, Y., Spitz, E., Smith, C. & You, L. Oscillations by minimal bacterial suicide circuits reveal hidden facets of host-circuit physiology. *PloS One* 5, e11909, 2010). The hlyE gene was taken via PCR from the genomic DNA of MG1655, while mCCL21 (mouse CCL21) and CDD-iRGD were synthesized. These genes were cloned into the lysis plasmid, under the control of either the ptac or pLuxI promoters (De Boer, H. A., Comstock, L. J. & Vasser, M. The tac promoter: a functional hybrid derived from the trp and lac promoters. *Proceedings of the National Academy of Sciences* 80, 21-25, 1983). Co-culturing was performed with HeLa cells and either motile or non-motile *S. typhimurium*, SL1344. For full strain and plasmid information, also see Supplementary Information.

The oscillator plasmids were constructed by modifying and combining published constructs (Danino, T., Mondrago'n-Palomino, O., Tsimring, L. & Hasty, J. A synchronized quorum of genetic clocks. *Nature* 463, 326-330 (2010); Stricker, J. et al. A fast, robust and tunable synthetic gene oscillator. *Nature* 456, 516-519 (2008); Prindle, A. et al. A sensing array of radically coupled genetic 'biopixels'. *Nature* 481, 39-44 (2012)) by PCR reactions and all circuit components except luxR were tagged by PCR with a carboxy-terminal ssrA tag (AANDENYALAA) (Keiler, K. C., Waller, P. & Sauer, R. Role of a peptide tagging system in degradation of proteins synthesized from damaged messenger RNA. *Science* 271, 990-993 (1996)) for fast degradation. We placed the activator and reporting elements (LuxI, CFP, and YFP) on one vector (IRAP2, Kan and ColE1) and the repressing elements (AiiA and LacI) on a second vector (IRAP3, Amp and p15A). The Thr-Ser (TS) constructs were constructed by adding various TS repeat inserts between the CFP and the LAA tag. For example, for two TS, the amino acid sequence 'TSTS' was inserted immediately before the degradation tag 'AANDENYA-LAA'. The AAV construct was constructed by replacing the IAA' portion of the degradation tag with 'AAV'.

Microfluidics and Microscopy

The microfluidic devices and experiment preparation protocols used in this study are similar to those previously reported from our group (Prindle, A. et al. A sensing array of radically coupled genetic 'biopixels'. *Nature* 481, 39-44, 2012). The bacteria growth chambers were 100×100 µm in area and approximately 1.4 µm in height. For co-culture experiments on the chip, we first loaded a suspended culture of HeLa cells in the device media channels at very low flow rates, to allow for adherence, and then incubated the device in a tissue culture incubator for 0.5-2 days to allow for proliferation (Kolnik, M., Tsimring, L. S. & Hasty, J. Vacuum-assisted cell loading enables shear-free mammalian microfluidic culture. *Lab On a Chip* 12, 4732-4737, 2012). On the day of the experiment, the device was transferred to the microscope and circuit-containing bacteria were loaded in the growth chambers before imaging. Acquisition of images was performed with a Nikon TI2 using a Photometrics CoolSnap cooled CCD camera. The scope and accessories were programmed using the Nikon Elements software. Additional details on microfluidics and microscopy can be found in the Supplementary Information.

Image acquisition was performed on a Nikon TI and images were acquired using a Photometrics CoolSnap cooled CCD camera or Photometrics QuantEM EMCCD camera, both controlled by Nikon Elements software. The cells were imaged inside a microfluidic device with the ability to mix or switch between two different media sources. On the day of the experiment, 50 ml of an overnight culture was diluted in 50 of Lysogeny Broth (Difco) and antibiotics. When cells reached a $D_{600\ nm}$ of 0.1, cells were spun down and resuspended in 5 ml of fresh media and loaded into the device. Three devices were used to study populations of varying sizes: small colony (100 cells) (Ferry, M. S., Razinkov, I. & Hasty, J. Microfluidics for synthetic biology from design to execution. Method s Enzymol. 497, 295-372), large colony (5,000 cells) (Danino, T., Mondrago'n-Palomino, O., Tsimring, L. & Hasty, J. A synchronized quorum of genetic clocks. *Nature* 463, 326-330 (2010)), and multiple large colonies (500 colonies of 5,000 cells) (Prindle, A. et al. A sensing array of radically coupled genetic 'biopixels'. *Nature* 481, 39-44 (2012)).

Data Analysis

Single cell and individual trap fluorescent trajectories were obtained from time-lapse images using our previously developed algorithms (Prindle, A. et al. A sensing array of radically coupled genetic 'biopixels'. *Nature* 481, 39-44 (2012); Ferry, M. S., Razinkov, I. & Hasty, J. Microfluidics for synthetic biology from design to execution. *Methods Enzymol.* 497, 295-372) and built-in MATLAB functions. We identified peaks and troughs from these trajectories and used these values to calculate periods and amplitudes. To calculate the coupling delay in FIG. 10A and offset time in FIG. 10A, we measured the difference between the 10% amplitude points of trajectory pairs. The induction time was measured from induction start time to 10% amplitude of the induced module. To extract both frequencies from time series data, we performed Fourier transformations using the Lomb-Scargle algorithm. We used two sequential transformations to isolate each component separately. First, we used a band-pass filter (5-25 min) to extract the fast intracellular clock component. Then, we filtered out these fast frequencies using a second band-pass filter (75-150 min) to extract the slower quorum clock component. Finally, we overlay the two power spectra, preserving the relative amplitude of the peaks.

Online Content

Any additional Methods, Extended Data display items and Source Data are available in the online version of the paper; references unique to these sections appear only in the online paper.

Additional Experimental Results

Degradation Tag Experiments

Figure 14C:
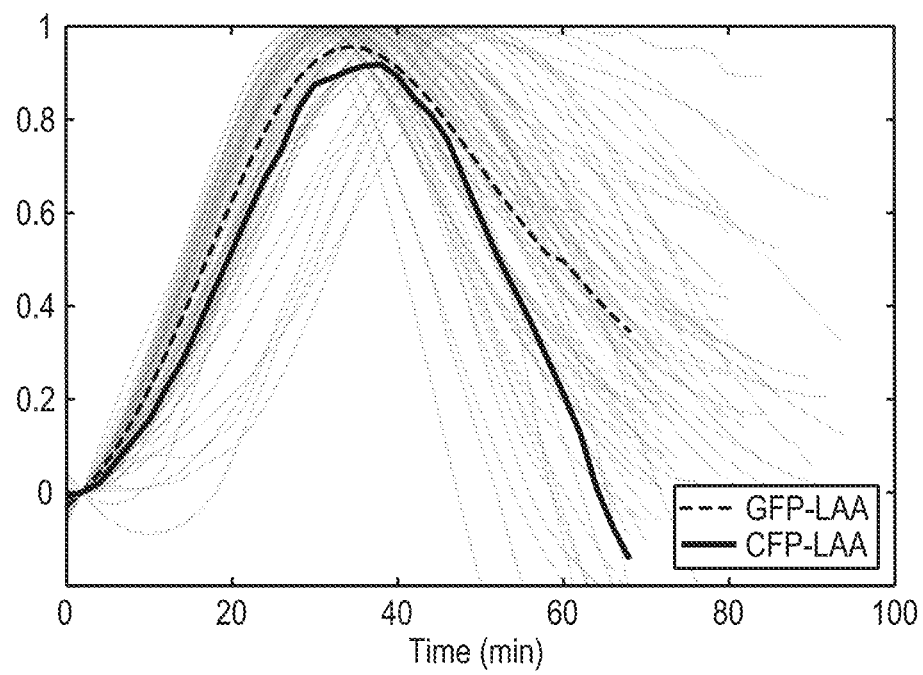
In FIGS. 14C-14F, dark lines indicate the means of all trajectories.
Figure 14D:
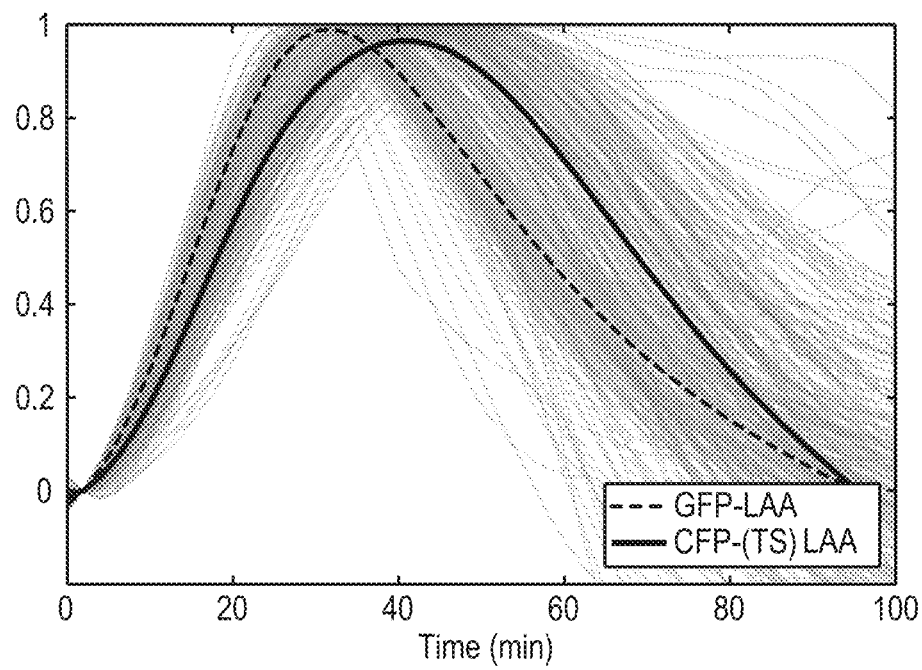
Figure 14E:
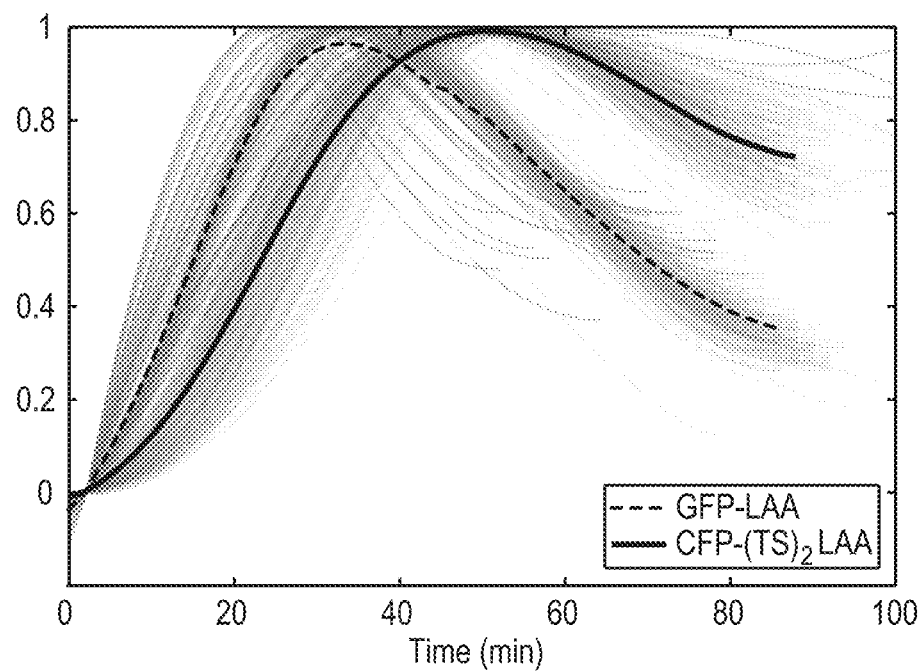
Figure 14F:
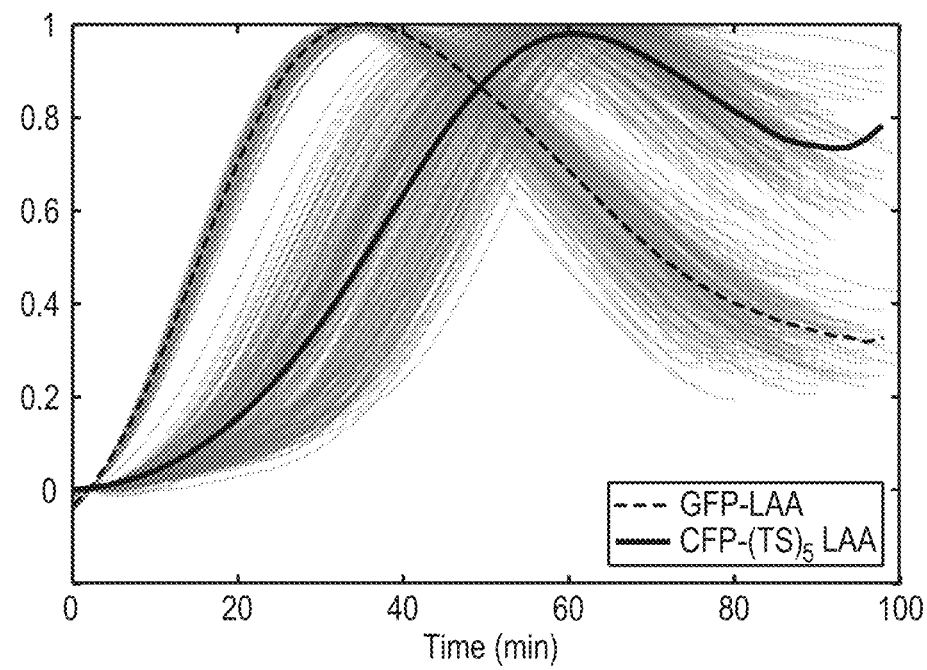

In addition to exploring the effect of variable-length linker (TS repeats) on the phase-shift in module degradation (FIG. 14A-F), we tested a well characterized AAV degradation tag (Andersen, J. B. et al. New unstable variants of green fluorescent protein for studies of transient gene expression in bacteria. *Applied and Environmental Microbiology* 64, 2240-2246, 1998). In Andersen et al, GFP-AAV was shown to have 50% higher half-life than GFP-LAA. In this study, downstream module (CFP-AAV) showed a delay in degradation relative to the driver module (GFP-LAA) that was similar to that of the 2 TS-linker sequence (FIG. 14B bottom). Further characterization is required to determine the differences in the mechanism of action between variable-length TS linker sequence before the SspB binding region and the AAV degradation tag. While CFP to GFP bleed-over is more significant than GFP to CFP bleed-over, the CFP to GFP bleed-over is not relevant to our experiment in FIG. 10A, where the induced protein (GFP) drives the protein level of the coupled protein (CFP). Thus, we performed an experiment to test the potential for bleeding from sfGFP into CFP fluorescence channel by activation sfGFP with 10 nM AHL in a strain that lacked CFP fluorophore. We saw no change in CFP fluorescence while sfGFP increased as expected (FIG. 14B top panel).

NFB Helps $H_2O_2$ Synchronize Oscillations Between Colonies

Figures 16A, 16B:
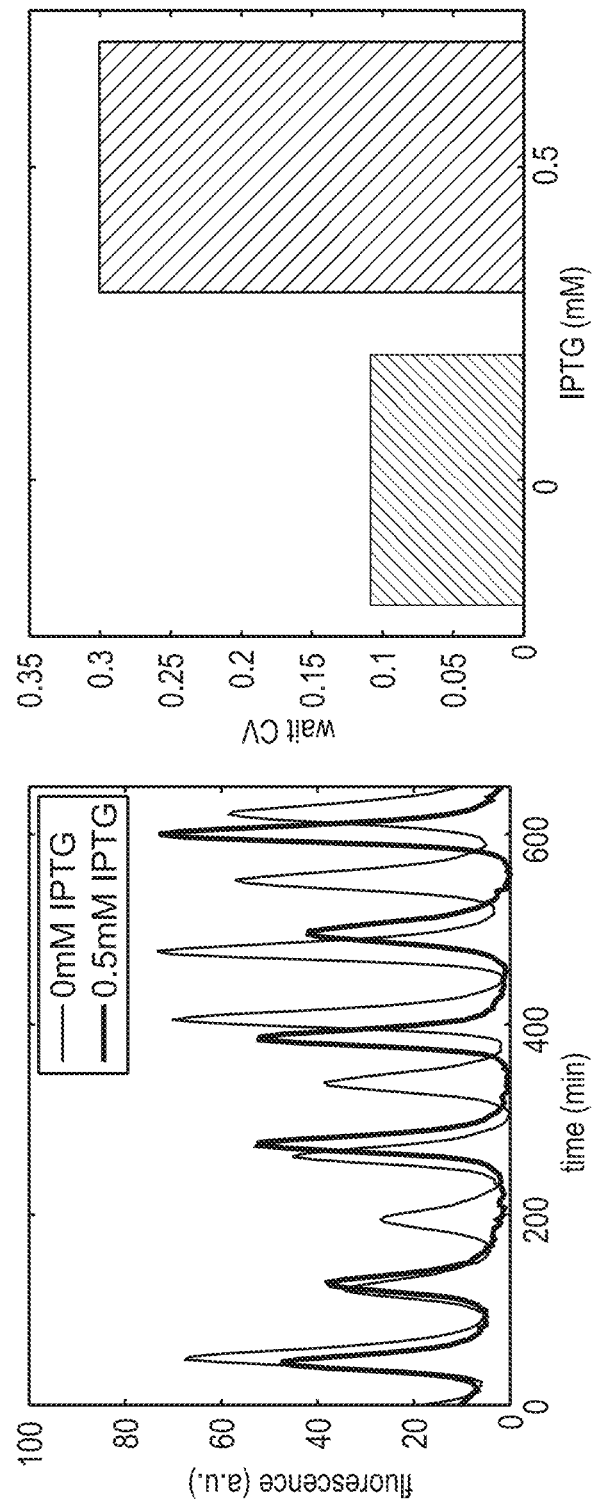
FIG. 16. The intracellular clock increases robustness in the coupled oscillator system by reducing the period of the quorum clock. (A) Removal of IPTG, which increases intracellular clock strength, leads to more regular oscillations (experimental). (B) The decrease in variability of the inter-pulse time of the coupled oscillator without IPTG suggests that the intracellular clock plays an important role in the inter-pulse dynamics (experimental). (C) At very high flow rates, the quorum clock oscillates irregularly. Tuning up the intracellular clock reduces the quorum clock period, restoring regular oscillations and allowing for global level synchronization between colonies due to $H_2O_2$ biopixel coupling. Genetic addition of the intracellular clock (0.1 mM IPTG) helps synchronize the quorum clock at high flows (430 μm s$^{-1}$). Increasing the strength of the intracellular clock with removal of IPTG further enhances $H_2O_2$ inter-colony synchronization (experimental, thick black lines indicate the mean of experimental races).
Figure 16C:
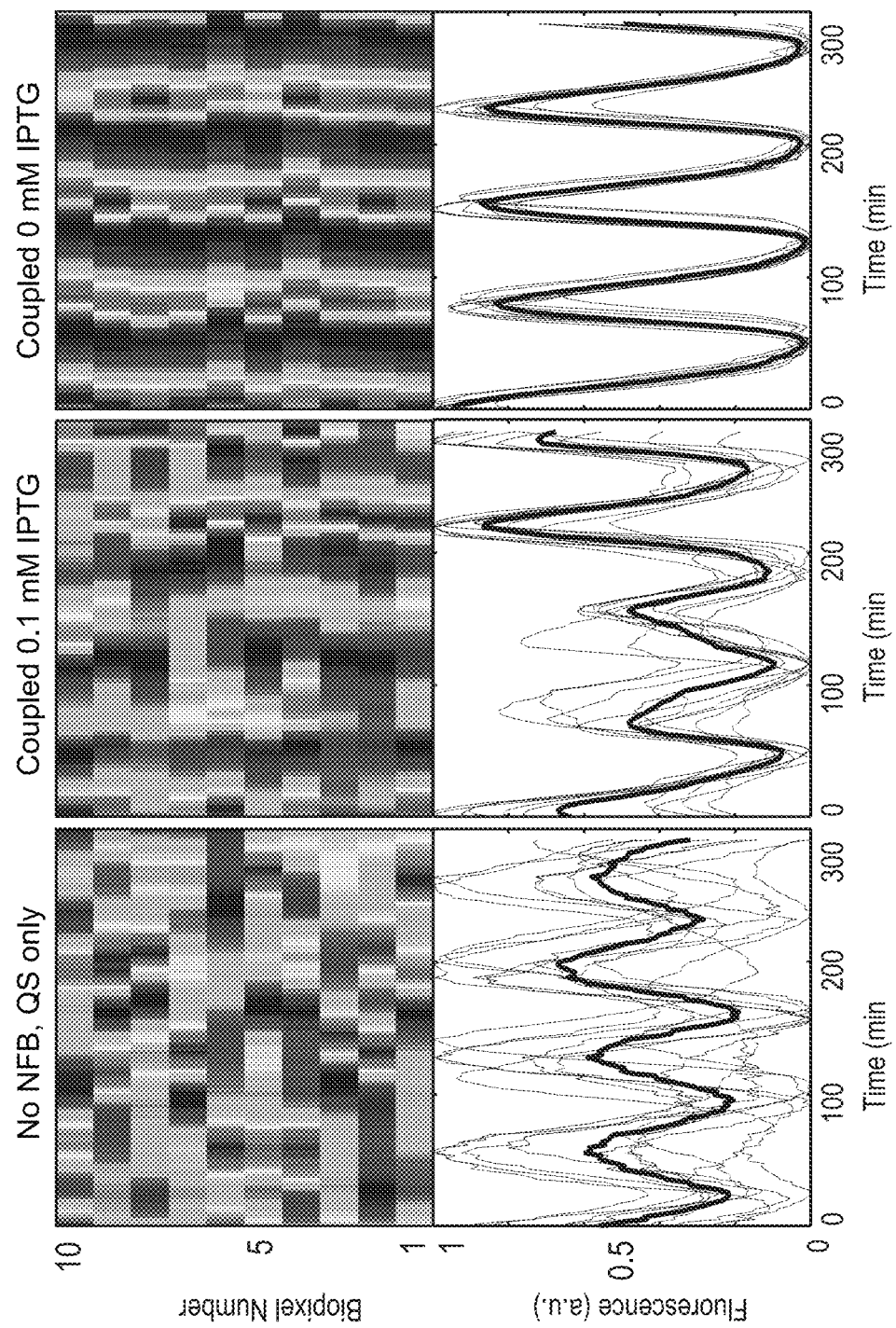

We defined the inter-pulse (wait) time as the time between the 10% downslope point of one peak and 10% upslope point of the following peak (FIG. 14A). The mean QS interpulse time decreased with addition of IPTG (0.5 mM) to the coupled system, while the time of each pulse stayed constant. In addition, we find that QS trajectories from the coupled oscillator system showed significantly lower variability without IPTG as compared to 0.5 mM IPTG (FIG. 16A-B). These results suggest that stronger NFB (0 mM IPTG) associated with higher NFB protein production (Stricker, J. et al. A fast, robust and tunable synthetic gene oscillator. *Nature* 456, 516-519 (2008)) leads to shorter and more robust inter-pulse behavior in the coupled system. In large biopixel devices, less robust colony-level oscillations prevent $H_2O_2$ from effectively coupling neighboring pixels, resulting in unsynchronized QS oscillations (No NFB in FIG. 16C). NFB reduces inter-pulse duration noise, which allows $H_2O_2$ to synchronize QS oscillations in neighboring colonies in biopixel devices (0.1 mM IPTG in FIG. 16C). Increasing NFB strength, further.

$H_2O_2$ Increases Protein Degradation Rate

Our analysis of $H_2O_2$ synchronized quorum clock trajectories showed decrease in the period and increase in the amplitude of oscillations (FIG. 13B Top). $H_2O_2$ synchronization leads to clear reduction of the degradation time in these trajectories (FIG. 17A). One of the significant contributors to the decrease in the period is the increase in the activity of ClpXP targeted proteins, which we quantified as the rate of CFP fluorescence decrease from the peak time to the 10% downslope time. FIG. 17B shows a significant increase in the ClpXP degradation rate (3 x) due to $H_2O_2$ coupling.

Model Formulation

QS Oscillator

To describe dynamic behavior of uncoupled QS oscillator, we expanded on the delay-differential equation model presented in (Danino, T., Mondragón-Palomino, O., Tsimring, L. & Hasty, J. A synchronized quorum of genetic clocks. *Nature* 463, 326-330 (2010)). In addition to the equations for LuxI (I), AiiA (A), internal AHL (Hi), external AHL (He), we included AHL substrate (S), consisting of acyl-ACPs and S-Adenosylmethionine (SAM) (Parsek, M. R. & Greenberg, E. P. Acyl-homoserine lactone quorum sensing in gram-negative bacteria: a signaling mechanism involved in associations with higher organisms. *Proceedings of the National Academy of Sciences* 97, 8789-8793 (2000)), to account for the slowing down of Hi production while the number of LuxI molecules is still on the rise. Transcription, translation, and maturation rate of proteins are combined into a single time-delay parameter $\tau_H$. Transcriptional activation by the LuxR and AHL complex (2 of each LuxR and AHL molecules) give delayed production term $P(\tau_H)$, which depends on the past concentration of internal AHL, $Hi(t-\tau_H)$. We assumed a constant level of LuxR since it is not tagged for fast degradation and has a large amount of genetic copies on the plasmid (it is on colE1 twice and p15A once). We used hill coefficient of 4 in accordance with (Müller, J., Kuttler, C., Hense, B. A., Rothballer, M. & Hartmann, A. Cell-cell communication by quorum sensing and dimension-reduction. *Journal of Mathematical Biology* 53, 672-702 (2006)) to account for high AHL cooperativity possibly due to AHL-LuxR polymerization. Diffusion of AHL through cell membrane is described by terms proportional to D, while dilution of external AHL is described by the term proportional to μ. Cell density parameter d was incorporated into the system to account for the difference in the total cell volume and media volume. Enzymatic degradation terms proportional to $\gamma_I$ and $\gamma_A$ describe enzymatic degradation of LuxI and AiiA respectively through Michaelis-Mentent kinetics. Different values of $k_I$ and $k_A$ represent different preferential binding dynamics of LuxI and AiiA to ClpXP.

$$\frac{\partial A}{\partial t} = C_A P(\tau_H) - \frac{\gamma_A (A/k_A)}{1 + A/k_A + I/k_I} \quad (1)$$

$$\frac{\partial I}{\partial t} = C_I P(\tau_H) - \frac{\gamma_I (I/k_I)}{1 + A/k_A + I/k_I} \quad (2)$$

$$\frac{\partial H_i}{\partial t} = \frac{bI(S/k_S)}{1 + S/k_S} - \frac{\gamma_H A(H_i/k_H)}{1 + H_i/k_H} + D(H_e - H_i) \quad (3)$$

$$\frac{\partial H_e}{\partial t} = -\frac{d}{1-d} D(H_e - H_i) - \mu H_e \quad (4)$$

$$\frac{\partial S}{\partial t} = S_0 - S - \frac{bI(S/k_S)}{1 + (S/k_S)} \quad (5)$$

$$P(\tau_H) = \alpha_0 + \frac{\alpha_H (H(t-\tau_H)/h0)^4}{1 + (H(t-\tau_H)/h0)^4}$$

More information in this regard can be found at, for example, section "Model Parameters Values" of the present application.

NFB Oscillator

To describe dynamic behavior of NFB oscillator, we used a single delay-differential equation for LacI (L) based on (Mather, W., Bennett, M. R., Hasty, J. & Tsimring, L. S. Delay-induced degrade-and-fire oscillations in small genetic circuits. *Physical Review Letters* 102, 068105 (2009)). Transcription, translation, and maturation of proteins are lumped together into time-delay parameter $\tau_L$. Transcriptional inactivation of LacI gives the delayed production term $Q(\tau_L)$, which depends on the past concentration of LacI, $L(t-\tau_L)$. Enzymatic degradation of LacI is described by the term proportional to $\gamma_L$ through Michaelis-Mentent kinetics. Parameter C in production expression Q represents the effect of IPTG on the strength of LacI repression.

$$\frac{\partial L}{\partial t} = Q(\tau_L) - \frac{\gamma_L (L/k_L)}{1 + L/k_L} \quad (6)$$

$$Q(\tau_L) = \frac{\alpha_L}{1 + (L(t-\tau_L)/C)^2}$$

The dynamics of the above model accounted for most of the experimental results. To resolve the amplitude increase in the NFB oscillator when coupled to the QS oscillator during the QS pulse we had to include reporter dynamics with equations for YFP precursor ($\gamma_p$) and mature YFP ($\gamma_m$). These additional equations are not required to explain the QS dynamics in the coupled system. More information in this regard can be found at, for example, section "Model Parameters Values" of the present application.

$$\frac{\partial L}{\partial t} = Q(\tau_L) - \frac{\gamma_L (L/k_L)}{1 + L/k_L + Y_p/k_L + Y_p/k_L} \quad (7)$$

$$\frac{\partial Y_p}{\partial t} = Q(\tau_L) - \frac{\gamma_L (Y_p/k_L)}{1 + L/k_L + Y_p/k_L + Y_m/k_L} - Y_p \quad (8)$$

$$\frac{\partial Y_m}{\partial t} = Y_p - \frac{\gamma_L (Y_m/k_L)}{1 + L/k_L + Y_p/k_L + Y_m/k_L} \quad (9)$$

$$Q(\tau_L) = \frac{\alpha_L}{1 + (L(t-\tau_L)/C)^2}$$

Coupled NFB and QS Oscillators

Coupling of the two oscillators was accomplished by increasing the effective "queueing" effect through CplXP degradation (Cookson, N. A. et al. Queueing up for enzymatic processing: correlated signaling through coupled degradation. *Mol. Syst. Biol.* 7, 561 (2011)). In the uncoupled case, the degradation of the two oscillator components would be independent, $$\frac{ClpXP}{1+QS} + \frac{ClpXP}{1+NFB},$$

while in the coupled scenario, $$\frac{ClpXP}{1+QS+NFB},$$

the degraded components end up in the same degradation term. To couple NFB and QS oscillators through ClpXP degradation, we added LuxI and AiiA from QS system to the degradation expressions in NFB system and LacI (L) from NFB system to the degradation expression in QS system.

$$\frac{\partial A}{\partial t} = C_A P(\tau_H) - \frac{\gamma_A(A/k_A)}{1+A/k_A+I/k_I+L} \quad (10)$$

$$\frac{\partial I}{\partial t} = C_I P(\tau_H) - \frac{\gamma_I(I/k_I)}{1+A/k_A+I/k_I+L} \quad (11)$$

$$\frac{\partial H_i}{\partial t} = \frac{bI(S/k_S)}{1+S/k_S} - \frac{\gamma_H A(H_i/k_H)}{1+H_i/k_H} + D(H_e - H_i) \quad (12)$$

$$\frac{\partial H_e}{\partial t} = -\frac{d}{1-d}D(H_e - H_i) - \mu H_e \quad (13)$$

$$\frac{\partial S}{\partial t} = S_0 - S - \frac{bI(S/k_S)}{1+(S/k_S)} \quad (14)$$

$$\frac{\partial L}{\partial t} = Q(\tau_L) - \frac{\gamma_L(L/k_L)}{1+L/k_L+A+I} \quad (15)$$

$$P(\tau_H) = \alpha_0 + \frac{\alpha_H(H(t-\tau_H)/h0)^4}{1+(H(t-\tau_H)/h0)^4}$$

$$Q(\tau_L) = \frac{\alpha_L}{1+(L(t-\tau_L)/C)^2}$$

More information in this regard can be found at, for example, section "Model Parameter Values" of the present application. We varied the flow p, IPTG concentration C, and arabinose concentration $\alpha_L$ to recapture many of the experimental findings.

Leader Cell Wait Time Shortening

Figure 15B:
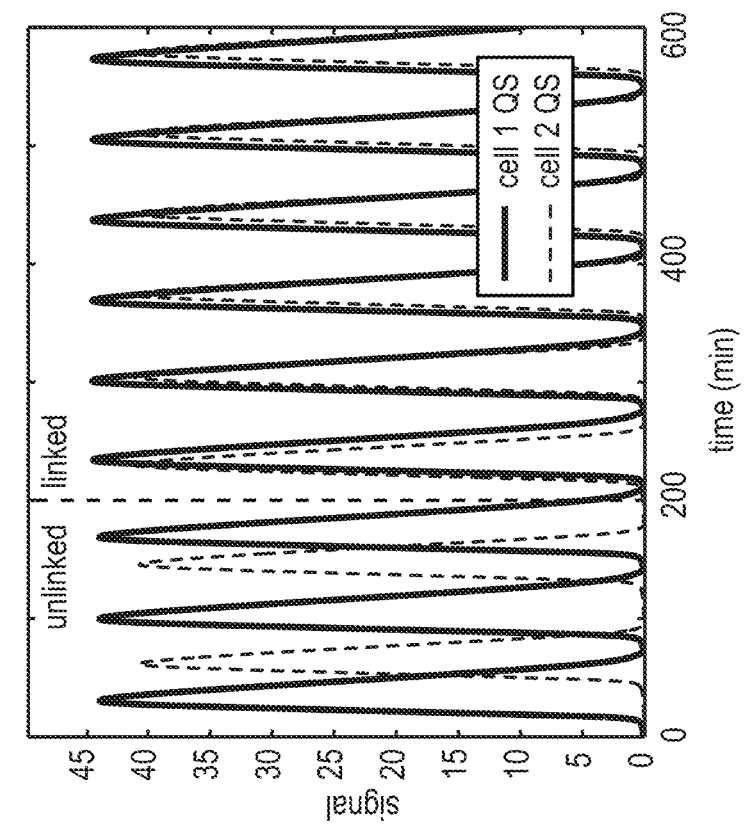
FIG. 15. Cell-cell communication by AHL reduces variability in the quorum clock. (A) Individual 'leader' cells show early activation of quorum clock proteins relative to the mean population response. (B) In a two-cell simulation, cells 1 and 2 start out unlinked with slightly different constitutive production of AiiA and LuxI. At t=100 min the two cells are linked through external AHL in the media, showing the cell with slower dynamics (cell 2) linking up to cell 1 with shorter periods. (C) Cells 1 and 2 start out unlinked with cell 1 including intracellular clock dynamics (green) that result in higher frequency oscillations in cell 1. When the cells are linked (t=100), the slower cell 2, without the intracellular clock, links on to the faster cell through external AHL communication between the cells. (D) Trajectories of 20 cells (different line traces) with noisy constitutive production at lux promoter synchronize when their external AHL pool is mixed at t=400 min. Mean trajectory is shown in thick solid line. (E) Period variability after cell synching (diagonal right) is lower than in individual cells (diagonal left). QS: quorum-sensing oscillator.
Figure 15A:
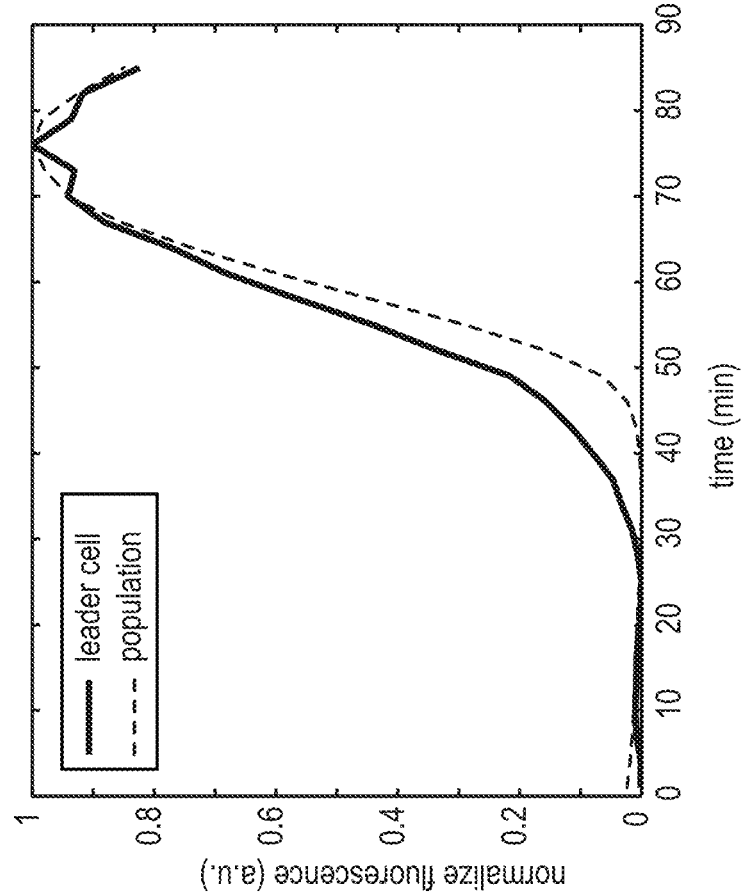
Figure 15D:
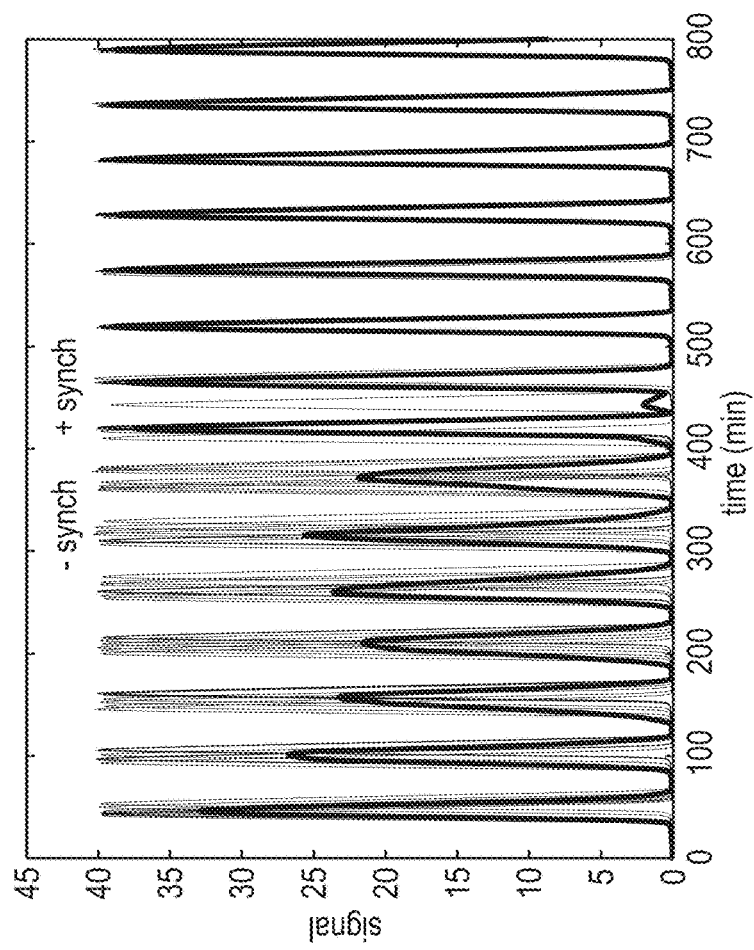
Figure 15C:
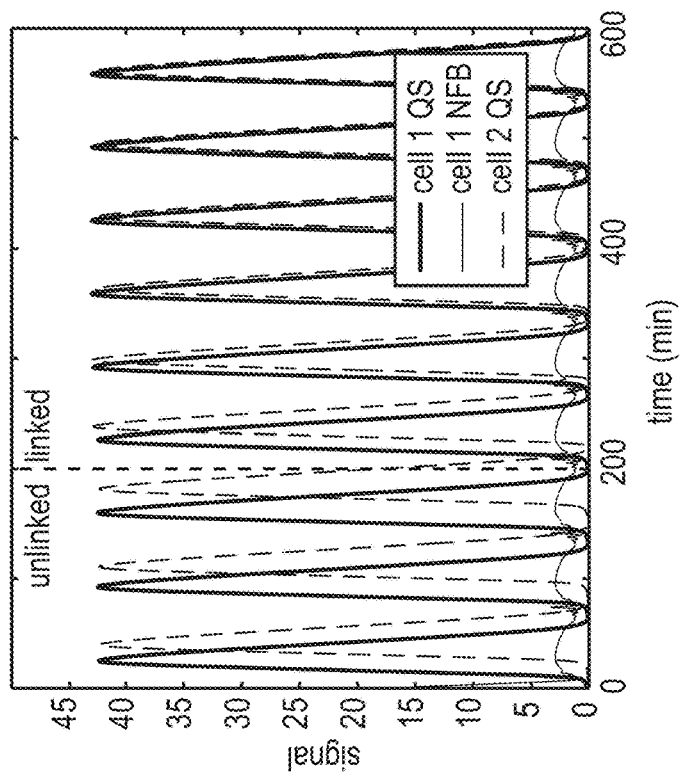
Figure 15E:
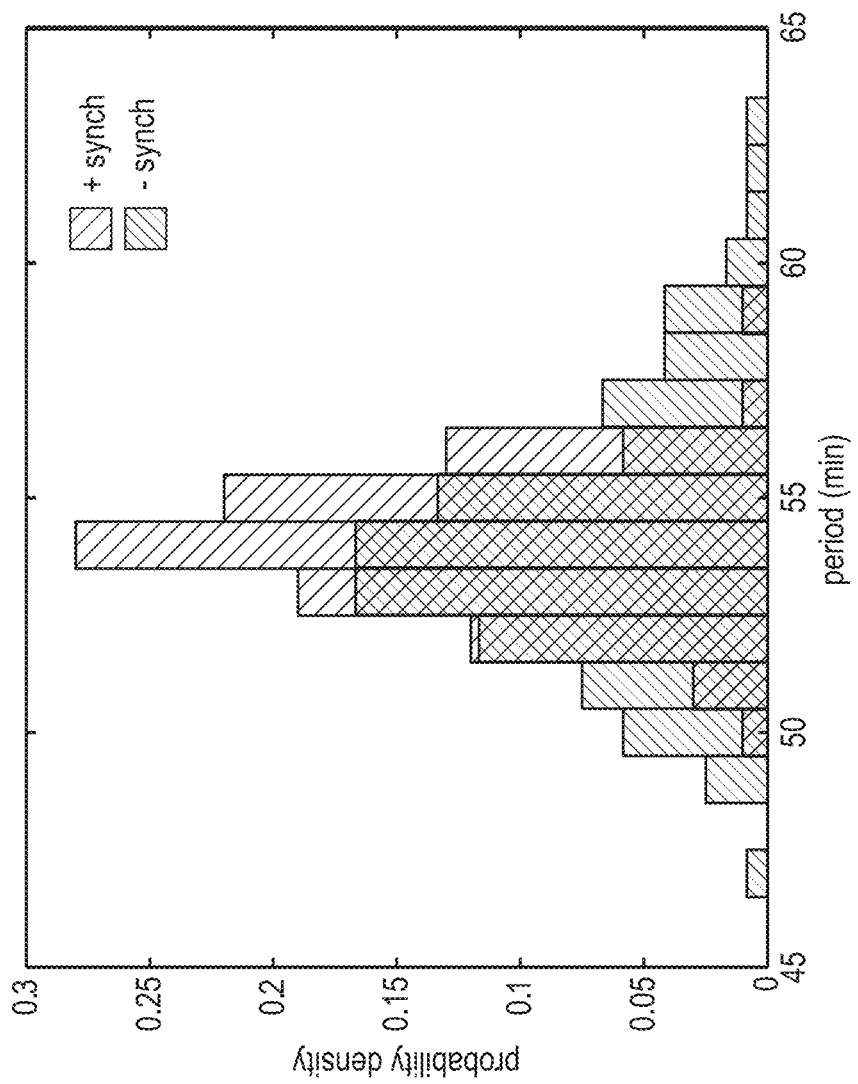

To understand the multicellular dynamics of QS pulse activation we constructed a model with two identical cells that share external AHL ($H_e$). We first considered a QS only system consisting of two cells with slightly different constitutive production of AiiA and LuxI. In this system, the slower cell couples to the faster one, suggesting that cells whose QS pulse fires first cause QS pulse activation in the nearby cells through AHL cell-to-cell communication (FIG. 15A). Next we added NFB to cell 1 in a two-cell system, resulting in period shortening of that cell. As the result, when the two cells were linked through external AHL, the slower cell 2 (without NFB), coupled to the faster cell 1 (FIG. 15B). Consequently, even though NFB might be out of phase in different cells, the onset of QS pulse in the faster cells can initiate the propagation of the QS pulse through the rest of the cells in the nearby region. This effect further reduces cell-cell QS variability, which we see from period variability reduction in a 20-cell model (FIG. 15D). We added noise to constitutive production of AiiA and LuxI proteins ($\alpha_0=0.6\pm0.1$) of each of the 20 cells and showed period variability reduction in synched vs unsynched cells (FIG. 15E).

QS and $H_2O_2$ Coupled Through Queueing

To describe dynamic behavior of QS oscillator in response to $H_2O_2$ produced during LuxI fluorescent reporter expression, we added a differential equation describing production and degradation of $H_2O_2$ ($V_i$ and $V_e$) to the QS oscillator delay-differential equation model. We assumed that the production of $H_2O_2$ is dependent on the concentration of LuxI, which is under the same promoter as the CFP fluorescent protein. Degradation of $H_2O_2$ by catalase is proportional to its concentration. $H_2O_2$ affects the QS oscillator in two characteristic ways. First, ArcA, which is under normal conditions partially represses Lux promoter, is inactivated under oxidizing conditions triggered by $H_2O_2$, relieving Lux repression and increasing LuxI and AiiA production. We model this phenomenon by adding a multiplier to the production term that is dependent on $H_2O_2$ concentration. Second, $H_2O_2$ has been shown to reduce ClpXP load, leading to increased rate of AiiA and LuxI degradation. Again, we model this behavior by adding a multiplier in front of the degradation term, dependent on $H_2O_2$ concentration. Finally, $H_2O_2$ can freely diffuse across cell membrane, which we describe a diffusion term characterized by diffusion parameter $D_V$. Extracellular $H_2O_2$ ($V_e$) can further leave the system with the rate proportional to its concentration.

$$\frac{\partial A}{\partial t} = C_A P(\alpha_H, \tau) - (1+V_i)\frac{\gamma_A(A/k_A)}{1+A/k_A+I/k_I} \quad (16)$$

$$\frac{\partial I}{\partial t} = C_I P(\alpha_H, \tau) - (1+V_i)\frac{\gamma_I(I/k_I)}{1+A/k_A+I/k_I} \quad (17)$$

$$\frac{\partial H_i}{\partial t} = \frac{bI(S/k_S)}{1+S/k_S} - \frac{\gamma_H A(H_i/k_H)}{1+H_i/k_H} + D(H_e - H_i) \quad (18)$$

$$\frac{\partial H_e}{\partial t} = -\frac{d}{1-d}D(H_e - H_i) - \mu H_e \quad (19)$$

$$\frac{\partial S}{\partial t} = S_0 - S - \frac{bI(S/k_S)}{1+(S/k_S)} \quad (20)$$

$$\frac{\partial V}{\partial t} = \frac{\delta(I/C_I)}{1+I/C_I} - V_i + D_V(V_e - V_i) \quad (21)$$

$$\frac{\partial V_e}{\partial t} = \frac{d}{1-d}D_V(V_e - V_i) - \mu_V * V_e \quad (22)$$

$$P(\tau_H) = (1+f_p V)\left(\alpha_0 + \frac{\alpha_H(H(t-\tau_H)/h0)^4}{1+(H(t-\tau_H)/h0)^4}\right)$$

$H_2O_2$ Increases QS Period Robustness

As we have mentioned before, reduction in inter-pulse duration leads to reduction in period variability arising from noise. Incorporating $H_2O_2$ effects on QS oscillator into our model (see above) results in several major changes in QS trajectory. First, as expected the amplitude of QS and the downslope time of QS decrease with addition of $H_2O_2$ (FIG. 17C). The result of these two effects also results in shortening of inter-pulse duration, which leads to more robust QS oscillations (FIG. 17D). We simulated the model to obtain at least 50 period measurements for period CV calculation. The noise was introduced into the model through addition of a noisy production term ($\alpha_0=\pm0.1$) to the delayed production term $$P(\tau_H) = \alpha_v + (1+f_p V)\left(\alpha_0 + \frac{\alpha_H(H(t-\tau_H)/h0)^4}{1+(H(t-\tau_H)/h0)^4}\right).$$

Interestingly, our model shows that individual effects of $H_2O_2$ activation of lux promoter and increase in ClpXP activity result in the increase the CV of the QS period (FIG. 17D). With respect to increased ClpXP activity, higher CV is mainly due to the resulting longer inter-pulse duration (FIG. 17C green). Increased lux promoter activity, however, leads to more variable degradation due to higher pulse amplitude variability. The two countering $H_2O_2$ effects seem to cancel each other's variability generating more robust QS oscillations.

Fitting Model Parameters to Experimental Results

To fit the NFB period data from experiments we used the following parameter scaling functions for the LacI production term $$\left(Q(\tau_L) = \frac{\alpha_L}{1 + (L(t - \tau_L)/C)^2}\right)$$

to fit IPTG and arabinose (ARA) concentrations:

$$alpha_L \propto A_A + D_A \frac{\left(\frac{ARA}{C_A}\right)^{H_A}}{\left(1 + \frac{ARA}{C_A}\right)^{H_A}}$$

$A_A = 0.2758, D_A = 1.6291, C_A = 0.5638, H_A = 0.9029$ $$C \propto A_C + D_C \frac{\left(\frac{IPTG}{C_C}\right)^{H_C}}{\left(1 + \frac{IPTG}{C_C}\right)^{H_C}}$$

$A_C = 0.0968, D_C = 60.8510, C_C = 8.2451, H_C = 0.4334$

Similarly we fit the model flow term p to the experimental flow values using the following function $$\mu = A_\mu \mu^2 + B_\mu \mu + C$$

$A_\mu = 1.2e-7, B_\mu = 0.0033, C_\mu = -0.11$

Model Parameter Values $C_A=1$ (AiiA copy number); $C_I=4$ (LuxI copy number); $\gamma_A=8$ (ClpXP degradation of AiiA); $\gamma_I=8$ (ClpXP degradation of LuxI); $K_A=1$ (AiiA binding affinity to ClpXP); $K_I=0.2$ (LuxI binding affinity to ClpXP); $\alpha_0=0.6$ (Lux promoter basal production); $\alpha_H=3$ (Lux promoter AHL induced production); $h_0=0.1$ (AHL promoter binding affinity); $\tau_H=1$ (delay in LuxI and AiiA production); b=1 (AHL synthesis rate by LuxI); $k_S=25$ (AHL substrate binding affinity to LuxI); $S_0=50$ (basal AHL substrate production); $\gamma_H=1$ (AHL degradation rate by AiiA); $k_H=0.1$ (AHL binding affinity to AiiA); D=0.8 (AHL diffusion across the membrane); d=0.1 (cell density); $\mu=0.5$ (flow rate); $\alpha_L=1$ (LacI/YFP production rate); C=0.0025 (LacI promoter binding affinity); $\tau_L=0.7$ (delay in LacI/YFP production); $k_L=0.001$ (LacI/YFP binding affinity to ClpXP); $\gamma_L=0.05$ (ClpXP degradation of LacI/YFP); $\delta=1$ (H2 O2 production due to QS fluorophores); $C_f=2$ (Michaelis constant); $f_p=1.3$ (strength of $H_2O_2$ activation of LuxI promoter); $D_F=8$ ($H_2O_2$ diffusion across membrane); $\mu_v=0$ (extracellular $H_2O_2$ dilution).

In Vivo Experiments

All animal work was approved by the committee on animal care (MIT, protocol 0414-022-17). Subcutaneous Tumor Model: Animal experiments were performed on 6 week old female BALB/c mice (Taconic Biosciences, Inc.) with bilateral subcutaneous hind flank tumors from an implanted mouse colon cancer cell line (MC26, Tanabe lab, Massachusetts General Hospital). Tumor cells were prepared for implantation at a concentration of 1e8 cell ml$^{-1}$ in DMEM (no phenol red). Cells were then implanted subcutaneously at a volume of 100 µL per flank, with each implant consisting of 1e7 cells. Tumors grew for approximately 2 weeks until reaching 4-10 mm in diameter.

Experimental Liver Metastasis Model

The experimental metastasis model was generated by injecting luciferase-producing mouse cancer cells into surgically externalized spleens of immuno-competent mice. Tumor cells seeded the liver during 90 seconds after which the spleen was re-moved to prevent ectopic tumor growth. The MC26-LucF cell line was used (Tanabe Lab, MGH) and injected at $5 \times 10^4$ cells/100 µL PBS into the spleens of female Balb/c mice 6 weeks of age (Taconic Biosciences, Inc.)

Bacterial Growth and Administration

Bacterial strains were grown overnight in LB media containing appropriate antibiotics and 0.2% glucose as for the in vitro experiments. A 1/100× dilution in fresh media with antibiotics was started the day of injection and grown until an OD<0.1 to prevent bacteria from reaching the quorum threshold (for SLC specifically). Bacteria were spun down and washed 2-3× with sterile PBS before injection into mice. Intratumoral injections of bacteria were performed at a concentration of 5e7 cells ml in PBS with a total volume of 10-20 µL injected per tumor, while intravenous injections were given at a total volume of 10 µL. For the SLC-3 strains injection, this final volume was equally divided between the three strains at the indicated density. For liver metastasis experiments, bacteria were grown in LB media containing appropriate antibiotics and 0.2% glucose until they reached an OD of 0.05, after which they were concentrated to 1-5e9 bacteria/mL and delivered via oral gavage.

Post-Administration Monitoring for Subcutaneous Liver Metastasis Models

Luminescent signal was measured with the IVIS Spectrum in vivo imaging system following bacterial injection. Measurements were compared relative to pre-injection values to follow dynamics. Subcutaneous tumor volume was quantified using calipers to measure the length, width, and height of each tumor throughout the imaging course (V=L× W×H). Volumes were compared to pre-injection values to follow physical tumor growth. Tumors were typically grown to an average of 300 mm$^3$ for sub-cutaneous experiments, and were grown for 5-7 days before experiments for the liver metastasis model. Survival of mice was tracked based on approved characteristics that necessitated euthanasia.

Statistical Analysis

Statistical tests were calculated either in Microsoft Excel (Student's t-test) or GraphPad Prism 5.0 (ANOVA with Bonferroni post-test, Log-rank test). The details of the statistical tests carried out are indicated in respective figure legends. Where data were approximately normally distributed, values were compared using either a Student's t-test or one-way ANOVA for single variable, or a two-way ANOVA for two variables. Mice were randomized in different groups before experiments.

All publications and patent applications mentioned in this specification are herein incorporated by reference to the same extent as if each individual publication or patent application was specifically and individually indicated to be incorporated by reference.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

REFERENCES

Andersen, J. B. et al. New unstable variants of green fluorescent protein for studies of transient gene expression in bacteria. *Applied and environmental microbiology* 64, 2240-2246 (1998).

Baban, C. K., Cronin, M., OŠHanlon, D., OŠSullivan, G. C. & Tangney, M. Bacteria as vectors for gene therapy of cancer. *Bioeng Bugs* 1, 385-394 (2010).

Begley, C. G. & Ellis, L. M. Drug development: Raise standards for preclinical cancer re-search. *Nature* 483, 531-533 (2012).

Buchler, N. E. & Louis, M. Molecular titration and ultra-sensitivity in regulatory networks. *J. Mol. Biol.* 384, 1106-1119 (2008).

Burger, A., Walczak, A. M. & Wolynes, P. G. Abduction and asylum in the lives of transcription factors. *Proc. Natl Acad. Sci. USA* 107, 4016-4021 (2010).

Cann, S. H., Van Netten, J. & Van Netten, C. Dr. William Coley and tumour regression: a place in history or in the future. *Postgraduate medical journal* 79, 672-680 (2003).

Chen, R. et al. Application of a pro-apoptotic peptide to intratumorally spreading cancer therapy. *Cancer Research* 73, 1352-1361 (2013).

Cheong, I. et al. A bacterial protein enhances the release and efficacy of liposomal cancer drugs. *Science* 314, 1308-1311 (2006).

Cho, I. & Blaser, M. J. The human microbiome: at the interface of health and disease. *Nature Reviews Genetics* 13, 260-270 (2012).

Coley, W. B. The treatment of inoperable sarcoma by bacterial toxins (the mixed toxins of the *streptococcus erysipelas* and the *bacillus prodigiosus*). *Proceedings of the Royal Society of Medicine* 3, 1 (1910).

Cookson, N. A. et al. Queueing up for enzymatic processing: correlated signaling through coupled degradation. *Molecular systems biology* 7 (2011).

Dang, L. H., Bettegowda, C., Huso, D. L., Kinzler, K. W. & Vogelstein, B. Combination bacteriolytic therapy for the treatment of experimental tumors. *Proceedings of the National Academy of Sciences* 98, 15155-15160 (2001).

Danino, T., Mondragón-Palomino, O., Tsimring, L. & Hasty, J. A synchronized quorum of genetic clocks. *Nature* 463, 326-330 (2010).

Danino, T., Lo, J., Prindle, A., Hasty, J. & Bhatia, S. N. In vivo gene expression dynamics of tumor-targeted bacteria. *ACS Synthetic Biology* 1.10, 465-470 (2012).

Danino, T., Prindle, A., Hasty, J. & Bhatia, S. Measuring growth and gene expression dynamics of tumor-targeted s. typhimurium bacteria. *JoVE (Journal of Visualized Experiments)* e50540-e50540 (2013).

Davila, M. L. et al. Efficacy and toxicity management of 19-28z car t cell therapy in b cell acute lymphoblastic leukemia. *Science Translational Medicine* 6, 224ra25-224ra25 (2014).

De Boer, H. A., Comstock, L. J. & Vasser, M. The tac promoter: a functional hybrid derived from the trp and lac promoters. *Proceedings of the National Academy of Sciences* 80, 21-25 (1983).

Del Vecchio, D., Ninfa, A. J. & Sontag, E. D. Modular cell biology: retroactivity and insulation. *Mol. Syst. Biol.* 4, 161 (2008).

Derman, A. I. et al. Phylogenetic analysis identifies many uncharacterized actin-like proteins (alps) in bacteria: regulated polymerization, dynamic instability and tread-milling in alp7a. *Molecular microbiology* 73, 534-552 (2009).

Ferry, M. S., Razinkov, I. & Hasty, J. Microfluidics for synthetic biology from design to execution. *Methods Enzymol.* 497, 295-372 (2011).

Fischbach, M. A., Bluestone, J. A. & Lim, W. A. Cell-based therapeutics: the next pillar of medicine. *Science translational medicine* 5, 179ps7-179ps7 (2013).

Folcher, M. & Fussenegger, M. Synthetic biology advancing clinical applications. *Current Opinion in Chemical Biology* (2012).

Forbes, N. S. Engineering the perfect (bacterial) cancer therapy. *Nature Reviews Cancer* 10, 785-794 (2010).

Fredriksson, A. et al. Decline in ribosomal fidelity contributes to the accumulation and stabilization of the master stress response regulator $\sigma S$ upon carbon starvation. *Genes Dev.* 21, 862-874 (2007).

Gardner, T. S., Cantor, C. R. & Collins, J. J. Construction of a genetic toggle switch from *Escherichia coli*. *Nature* 403, 339-342.

Garrett, W. S. Cancer and the microbiota. *Science* 348, 80-86 (2015)

Gerdes, K. The parB (hok/sok) locus of plasmid R1: a general purpose plasmid stabilization system. *Nature Biotechnology* 6, 1402-1405 (1988).

Goldbeter, A. & Koshland, D. E. An amplified sensitivity arising from covalent modification in biological systems. *Proc. Natl Acad. Sci. USA* 78, 6840-6844 (1981).

Griffith, K. L. & Grossman, A. D. Inducible protein degradation in *Bacillus subtilis* using heterologous peptide tags and adaptor proteins to target substrates to the protease ClpXP. *Mol. Microbiol.* 70, 1012-1025 (2008).

Grünberg, R. & Serrano, L. Strategies for protein synthetic biology. *Nucleic Acids Res.* 38, 2663-2675 (2010).

Hohmann, E. L., Oletta, C. A. & Miller, S. I. Evaluation of a phop/phoq-deleted, aroa-deleted live oral *Salmonella typhi* vaccine strain in human volunteers. *Vaccine* 14, 19-24 (1996).

Hooshangi, S., Thiberge, S. & Weiss, R. Ultrasensitivity and noise propagation in a synthetic transcriptional cascade. *Proc. Natl Acad. Sci. USA* 102, 3581-3586 (2005).

June, C. H. et al. Engineered t cells for cancer therapy. *Cancer Immunology, Immunotherapy* 1-7 (2014).

Jeong, J.-H. et al. Anti-tumoral effect of the mitochondrial target domain of noxa delivered by an engineered *Salmonella typhimurium*. *PloS One* 9, e80050 (2014).

Keiler, K., Waller, P. & Sauer, R. Role of a peptide tagging system in degradation of proteins synthesized from damaged messenger RNA. *Science* 271, 990-993 (1996).

Kolnik, M., Tsimring, L. S. & Hasty, J. Vacuum-assisted cell loading enables shear-free mammalian microfluidic culture. *Lab On a Chip* 12, 4732-4737 (2012).

Leone, V. et al. Effects of diurnal variation of gut microbes and high-fat feeding on host circadian clock function and metabolism. *Cell Host & Microbe* 17, 681-689 (2015).

Lien, K., Georgsdottir, S., Sivanathan, L., Chan, K. & Emmenegger, U. Low-dose metronomic chemotherapy: A systematic literature analysis. *European Journal of Cancer* (2013).

Loeffler, M., Le'Negrate, G., Krajewska, M. & Reed, J. C. *Salmonella typhimurium* engineered to produce CCL21 inhibit tumor growth. *Cancer Immunology, Immunotherapy* 58, 769-775 (2009)

Lutz, R. & Bujard, H. Independent and tight regulation of transcriptional units in *Escherichia coli* via the lacr/o, the tetr/o and arac/i1-i2 regulatory elements. Nucleic acids research 25, 1203-1210 (1997).

Loessner, H. et al. Remote control of tumour-targeted *Salmonella enterica serovar typhimurium* by the use of 1-arabinose as inducer of bacterial gene expression in vivo. Cellular microbiology 9, 1529-1537 (2007).

Marguet, P., Tanouchi, Y., Spitz, E., Smith, C. & You, L. Oscillations by minimal bacterial suicide circuits reveal hidden facets of host-circuit physiology. *PloS One* 5, e11909 (2010).

Mather, W., Bennett, M. R., Hasty, J. & Tsimring, L. S. Delay-induced degrade-and-fire oscillations in small genetic circuits. *Physical review letters* 102, 068105 (2009).

McGinness, K. E., Baker, T. A. & Sauer, R. T. Engineering controllable protein degradation. Mol. Cell 22, 701-707 (2006).

Meighen, E. A. Genetics of bacterial bioluminescence. Annual review of genetics 28, 117-139 (1994).

Merrikh, H., Ferrazzoli, A. E., Bougdour, A., Olivier-Mason, A. & Lovett, S. T. A DNA damage response in *Escherichia coli* involving the alternative sigma factor, RpoS. Proc. Natl Acad. Sci. USA 106, 611-616 (2009).

Miest, T. S. & Cattaneo, R. New viruses for cancer therapy: meeting clinical needs. *Nature Reviews Microbiology* 12, 23-34 (2014).

Mika, F. & Hengge, R. A two-component phosphotransfer network involving ArcB, ArcA, and RssB coordinates synthesis and proteolysis of σS (RpoS) in *E. coli*. Genes Dev. 19, 2770-2781 (2005).

Mondragón-Palomino, O., Danino, T., Selimkhanov, J., Tsimring, L. & Hasty, J. Entrainment of a population of synthetic genetic oscillators. *Science Signaling* 333, 1315 (2011).

Moon, T. S., Tamsir, A., Stanton, B. C. & Voigt, C. A. Genetic programs constructed from layered logic gates in single cells. Nature 491, 249-253 (2012).

Mukherji, S. et al. MicroRNAs can generate thresholds in target gene expression. Nature Genet. 43, 854-859 (2011).

Müller, J., Kuttler, C., Hense, B. A., Rothballer, M. & Hartmann, A. Cell-cell communication by quorum sensing and dimension-reduction. *Journal of mathematical biology* 53, 672-702 (2006).

Nandagopal, N. & Elowitz, M. B. Synthetic biology: integrated gene circuits. Science 333, 1244-1248 (2011).

Nguyen, Vu H., et al. "Genetically engineered *Salmonella typhimurium* as an imageable therapeutic probe for cancer," *Cancer Research* 70, 18-23 (2010).

O'Shea, C. C. Viruses-seeking and destroying the tumor program. *Oncogene* 24, 7640-7655 (2005).

Parsek, M. R. & Greenberg, E. P. Acyl-homoserine lactone quorum sensing in gram-negative bacteria: a signaling mechanism involved in associations with higher organisms. *Proceedings of the National Academy of Sciences* 97, 8789-8793 (2000).

Paton, Adrienne W, Renato Morona, and James C. Paton. "Bioengineered microbes in disease therapy." *Trends in molecular medicine* 18.7 (2012): 417-425.

Pawelek, John M., K. Brooks Low, and David Bermudes. "Tumor-targeted *Salmonella* as a novel anticancer vector," *Cancer Research* 57.20 (1997): 4537-4544.

Pédelacq, J.-D., Cabantous, S., Tran, T., Terwilliger, T. C. & Waldo, G. S. Engineering and characterization of a superfolder green fluorescent protein. Nature biotechnology 24, 79-88 (2005).

Press, W. H. in Numerical Recipes: The Art of Scientific Computing 3rd ed. (Cambridge Univ. Press, 2007).

Prindle, A. et al. A sensing array of radically coupled genetic 'biopixels'. Nature 481, 39-44 (2012).

Prindle, A. et al. Genetic circuits in *Salmonella typhimurium*. *ACS Synthetic Biology* 1, 458-464 (2012).

Prindle, Arthur, Jangir Selimkhanov, Howard Li, Ivan Razinkov, Lev S. Tsimring & Jeff Hasty. "Rapid and tunable post-translational coupling of genetic circuits," *Nature* 508, 387-391 (17 Apr. 2014) doi:10.1038/nature13238; Published online 9 Apr. 2014

Pruteanu, M.& Hengge-Aronis, R. The cellular level of the recognition factor RssB is transduction in σS turnover in *Escherichia coli*. Mol. Microbiol. 45, 1701-1713 (2002).

Purcell, O., Grierson, C. S., Bernardo, M. & Savery, N. J. Temperature dependence of ssra-tag mediated protein degradation. *Journal of Biological Engineering* 6, 10 (2012).

Quan, J. & Tian, J. Circular polymerase extension cloning of complex gene libraries and pathways. *PloS One* 4, e6441 (2009).

Riedel, C. U. et al. Construction of p16slux, a novel vector for improved bioluminescent labeling of gram-negative bacteria. *Applied and environmental microbiology* 73, 7092-7095 (2007).

Roberts, Nicholas J., et al. "Intratumoral injection of Clostridium novyi-NT spores induces antitumor responses." *Science translational medicine* 6.249 (2014): 249ra111-249ra111

Rosenfeld, N. & Alon, U. Response delays and the structure of transcription networks. *J. Mol. Biol.* 329, 645-654 (2003).

Ruder, Warren C., Ting Lu, and James J. Collins. "Synthetic biology moving into the clinic." *Science* 333.6047 (2011): 1248-1252.

Ryan, R. M., et al. "Bacterial delivery of a novel cytolysin to hypoxic areas of solid tumors." *Gene Therapy* 16, 329-339, (2009).

Schaefer, Amy L., et al. "A new class of homoserine lactone quorum-sensing signals." *Nature* 454: 595-599, 2008.

Shaked, Y. et al. Low-dose metronomic combined with intermittent bolus-dose cyclophosphamide is an effective long-term chemotherapy treatment strategy. *Cancer Research* 65, 7045-7051 (2005).

Sausville, E. A. & Burger, A. M. Contributions of human tumor xenografts to anticancer drug development. *Cancer Research* 66, 3351-3354 (2006).

Siuti, P., Yazbek, J. & Lu, T. K. Synthetic circuits integrating logic and memory in living cells. *Nature Biotechnol.* 31, 448-452 (2013).

Stecher, B. et al. Flagella and chemotaxis are required for efficient induction of *Salmonella enterica* serovar typhimurium colitis in streptomycin-pretreated mice. *Infection and Immunity* 72, 4138-4150 (2004).

Stricker, J. et al. A fast, robust and tunable synthetic gene oscillator. *Nature* 456, 516-519 (2008).

Strogatz, S. Nonlinear Dynamics and Chaos: with Applications to Physics, Biology, *Chemistry and Engineering* (Perseus Books, 2001).

Waters, Christopher M., and Bonnie L. Bassler. "Quorum sensing: cell-to-cell communication in bacteria." *Annu. Rev. Cell Dev. Biol.* 21: 319-346 (2005).

Wood, T., Kuhn, R. & Peretti, S. Enhanced plasmid stability through post-segregational killing of plasmid-free cells. *Biotechnology Techniques* 4, 39-44 (1990).

Supplementary Video 1. A video showing timelapse fluorescence microscopy of the Stealth Delivery Circuit (SDC) in Strain 1 (*S. typhimurium*, no ssrA tag on LuxI) at 60× magnification was taken. This video shows that bacterial colony grew in a microfluidic chamber until it reached a quorum threshold at which the cells fluoresced (indicating the quorum activation of the circuit genes) and a fraction of the population lysed. The survivors re-populated and grew until the threshold was reached again, repeating the process. The video tracked the colony for 8 lysis cycles and the lysis period of this strain was ~3 hours. Images were taken every 2 min at the bottom portion of a 100×100 μm chamber.

Supplementary Video 2. A video showing timelapse fluorescence microscopy of the SDC in Strain 2 (*S. typhimurium*, ssrA tag on LuxI) at 60× magnification was taken. This video shows that a longer lysis period with a higher degradation efficiency on LuxI. The bacterial colony grew in a microfluidic chamber until it reached a quorum threshold at which the cells fluoresced (indicating the quorum activation of the circuit genes) and a fraction of the population lysed. The survivors re-populated and grew until the threshold was reached again, repeating the process. The video tracked the colony for 6 lysis cycles and the lysis period of this strain was ~6 hours. The chamber size was 100×100 μm and images were taken every 2 min.

Supplementary Video 3. A video showing timelapse fluorescence microscopy of the SDC in Strain 13 (*E. coli*) at 60× magnification was taken. This video shows that the circuit was not as robust in *E. coli*, although regular lysis oscillations were still observed at 37° C. The bacterial colony grew in a microfluidic chamber until it reached a quorum threshold at which the cells fluoresced (indicating the quorum activation of the circuit genes) and a fraction of the population lysed. The survivors re-populated and grew until the threshold was reached again, repeating the process. The video tracked the colony for 6 lysis cycles and the lysis period of this strain was ~3 hours. The chamber size is 100×100 μm and images were taken every 2 min.

Supplementary Video 4. A video showing timelapse fluorescence microscopy of the SDC in Strain 1 (*S. typhimurium*) at 60× magnification was taken. This video shows that, in the first part of the experiment, media with 200 nM AHL was used and the bacteria could be seen entering a constant lysis state. In the device, indicated by fluorescent dye (red channel). The media was then switched to another source without AHL, in which the fluorescent dye was absent, and the bacteria reverted back to an oscillatory state, where the colony continued for 4 lysis cycles before the end of imaging. The chamber size was 100×100 μm and images were taken every 2 min.

Supplementary Video 5. A video showing bacteria and cancer cell co-culture on a microfluidic device at 60× magnification was taken. This video shows that Strain 3 (non-motile *S. typhimurium*, SDC with HlyE) was loaded in the growth chambers while HeLa cells grew in the main channel of the device. Bacteria could be seen growing in their chamber until they reached a quorum threshold and lyse. Upon lysis, the HeLa cells in the channel could be seen undergoing cell death. Timelapse fluorescence microscopy images were taken every 3 min.

Supplementary Video 6. A second video of bacteria and cancer cell co-culture on a microfluidic device at 60× magnification. This video shows that Strain 3 (non-motile *S. typhimurium*, SDC with HlyE) was loaded in the growth chambers while HeLa cells grew in the main channel of the device. Bacteria could be seen growing in their chamber until they reached a quorum threshold and lysed. Upon lysis, the HeLa cells in the channel could be seen undergoing cell death. Timelapse fluorescence microscopy images were taken every 3 min.

Supplementary Video 7. A video of bacteria and cancer cell co-culture in a tissue culture well-plate at 20× magnification was taken. This video shows that Strain 4 (motile *S. typhimurium*, SDC with HlyE) was loaded in the well with a monolayer HeLa cells. After the bacteria grew, the quorum event was visualized by the expression of green fluorescence protein (GFP). Shortly thereafter, HeLa cells could be seen exhibiting cell death. Timelapse fluorescence microscopy images were taken every 1 min.

Swofford, C. A., Van Dessel, N. & Forbes, N. S. Quorum-sensing *Salmonella* selectively trigger protein expression within tumors. *Proceedings of the National Academy of Sciences* 112, 3457-3462 (2015).

Thaiss, C. A., Levy, M. & Elinav, E. Chronobiomics: The biological clock as a new principle in host-microbial interactions. *PLoS Pathog* 11, e1005113 (2015).

Thakur, M. D. et al. Modelling vemurafenib resistance in melanoma reveals a strategy to forestall drug resistance. *Nature* 494, 251-255 (2013).

Tigges, M., Marquez-Lago, T., Stelling, J. & Fussenegger, M. A tunable synthetic mammalian oscillator. *Nature* 457, 309-312 (2009).

Unger, M. A., Chou, H.-P., Thorsen, T., Scherer, A. & Quake, S. R. Monolithic microfabricated valves and pumps by multilayer soft lithography. *Science*, 288, 113-116 (2000).

Weber, W. & Fussenegger, M. Emerging biomedical applications of synthetic biology. *Nature Reviews Genetics* 13, 21-35 (2011).

Wood, T., Kuhn, R. & Peretti, S. Enhanced plasmid stability through post-segregational killing of plasmid-free cells. *Biotechnology Techniques* 4, 39-44 (1990).

Xie, Z., Wroblewska, L., Prochazka, L., Weiss, R. & Benenson, Y. Multi-input RNAi-based logic circuit for identification of specific cancer cells. *Science* 333, 1307-1311 (2011).

Xuan, C. et al. Microbial dysbiosis is associated with human breast cancer. *PloS One* 9, e83744 (2014).

Young, K. D. & Young, R. Lytic action of cloned phi x174 gene e. *Journal of Virology* 44, 993-1002 (1982).

PCT Application No. PCT/US2012/069914, filed Dec. 14, 2012 and entitled MULTISCALE PLATFORM FOR COORDINATING CELLULAR ACTIVITY USING SYNTHETIC BIOLOGY.

U.S. Provisional Patent Application Ser. No. 61/576,976, filed Dec. 16, 2011.

No admission is made that any reference cited herein constitutes prior art. The discussion of the references states what their authors assert, and the applicants reserve the right to challenge the accuracy and pertinence of the cited documents. It will be clearly understood that, although a number of information sources, including scientific journal articles, patent documents, and textbooks, are referred to herein, this reference does not constitute an admission that any of these documents forms part of the common general knowledge in the art.

The discussion of the general methods given herein is intended for illustrative purposes only. It is not intended to be exhaustive or to limit the disclosure. Individual aspects or features of a particular embodiment are generally not limited to that particular embodiment, but, where applicable, are interchangeable and can be used in a selected embodiment, even if not specifically shown or described. It is expressly contemplated that any aspect or feature of the present disclosure can be combined with any other aspect, features, or combination of aspects and features disclosed herein. Other alternative methods and embodiments will be apparent to those of skill in the art upon review of this disclosure, and are to be included within the spirit and purview of this application.

What is claimed is:

1. A cell which has been genetically engineered to release a polypeptide from said cell when a population of said cells reaches a desired density and wherein said cell lyses when said population reaches said desired density, wherein said cell comprises an engineered Synchronized Lysis Circuit (SLC), said SLC comprising a positive and a negative feedback loop, wherein said positive feedback loop comprises (i) a promoter operably linked to a positive feedback genetic element and (ii) a degradation tagging sequence that encodes a degradation tag, wherein the positive feedback genetic element directly or indirectly activates the promoter, the degradation tag promotes the degradation of a protein encoded by the positive feedback genetic element, and the negative feedback loop promotes lysis of the cell.

2. The cell of claim 1, wherein said polypeptide is a therapeutic polypeptide.

3. The cell of claim 2, wherein said therapeutic polypeptide is selected from the group consisting of
   (i) a polypeptide which kills tumor cells or which inhibits the growth of tumor cells,
   (ii) a polypeptide which elicits immune responses against tumor cells,
   (iii) a polypeptide which recruits T-cell or dendritic cells,
   (iv) a polypeptide which causes or enhances apoptosis,
   (v) a polypeptide which enhances the release and/or efficacy of an anti-cancer drug, and
   (vi) a polypeptide which enhances the release and/or efficacy of a liposomal anti-cancer drug.

4. The cell of claim 1, wherein said cell is capable of proliferating within a tumor.

5. The cell of claim 1, wherein said cell has been genetically engineered to produce a polypeptide which lyses said cell when said population of said cells reaches said desired density.

6. The cell of claim 5, wherein said polypeptide which lyses said cell is under the control of the negative feedback loop.

7. The cell of claim 2, wherein not all of the cells in said population are lysed when said population of cells is at said desired density, thereby allowing regrowth of said cells after lysis and facilitating pulsatile release of said therapeutic polypeptide.

8. The cell of claim 1, wherein the timing of the release of said polypeptide is directly or indirectly coupled to the activity of the SLC.

9. The cell of claim 1, wherein the timing of the lysis of said cell is directly or indirectly coupled to the activity of the SLC.

10. A collection comprising a plurality of strains of the cells of claim 1, wherein each strain releases a different polypeptide when said strain reaches said desired density.

11. The collection of claim 10, wherein each strain in said plurality of strains is resistant to a different antibiotic.

12. The collection of claim 10, wherein each strain in said plurality of strains produces a bacteriocin which acts on some or all of the other strains in said collection.

13. The collection of claim 10, wherein at least one strain of said plurality of strains releases a polypeptide at a frequency different than the release frequency of at least one of the other strains in said collection.

14. A method of providing a polypeptide to a mammal comprising administering a cell of claim 1 to said mammal under conditions which facilitate the release of said polypeptide by said cell in said mammal.

15. A method of providing a plurality of polypeptides to a mammal comprising administering a collection comprising a plurality of strains of cells of claim 10 to said individual under conditions which facilitate the release of each of said different polypeptides by said plurality of strains in said individual.

16. The method of claim 15, wherein a first strain in said plurality of strains is administered to said individual and allowed to proliferate for a desired period of time and a second strain in said plurality of strains is subsequently administered to said individual and allowed to proliferate for a desired period of time, wherein the proliferation of said first strain is prevented or inhibited as a result of the administration of said second strain.

17. The method of claim 16, wherein said first strain is resistant to a first antibiotic and sensitive to a second antibiotic and said second strain is resistant to said second antibiotic and sensitive to said first antibiotic and wherein said first antibiotic is administered to said individual when proliferation of said first strain is desired and said second antibiotic is administered to said individual when proliferation of said second strain is desired.

18. The method of claim 15, wherein each of said strains in said plurality of strains is administered to said individual in a cyclic manner.

19. The method of claim 15, wherein the proliferation of only one of said plurality of strains in said individual is facilitated at a time while the proliferation of the other strains in said plurality of strains is prevented or inhibited.

20. The method of claim 1, wherein said negative feedback loop comprises the promoter.

21. The cell of claim 1, wherein the polypeptide is not part of the negative feedback loop.

22. The cell of claim 1, wherein the polypeptide does not promote lysis of the cell.

23. The cell of claim 1, wherein the positive feedback loop promotes production of the polypeptide.

24. The cell of claim 1, wherein the degradation tagging sequence is adjacent to the positive feedback genetic element.

25. The cell of claim 1, wherein the degradation tagging sequence is separated from the positive feedback genetic element by a linking sequence that encodes a linker.

26. The cell of claim 25, wherein the lysis of the cell is tunable by adjustment of the length of the linker.

27. The cell of claim 26, wherein the linker comprises one or more threonine-serine repeats.

28. The cell of claim 27, wherein the linker consists of between one and five threonine-serine repeats.

* * * * *